(12) United States Patent
Stivoric et al.

(10) Patent No.: US 7,285,090 B2
(45) Date of Patent: *Oct. 23, 2007

(54) APPARATUS FOR DETECTING, RECEIVING, DERIVING AND DISPLAYING HUMAN PHYSIOLOGICAL AND CONTEXTUAL INFORMATION

(75) Inventors: John Stivoric, Pittsburgh, PA (US); Christopher Pacione, Pittsburgh, PA (US); Eric Teller, Pittsburgh, PA (US); David Andre, Pittsburgh, PA (US); Christopher Kasabach, Pittsburgh, PA (US); Scott Boehmke, Wexford, PA (US); Suresh Vishnubhatla, Wexford, PA (US); Scott Safier, Pittsburgh, PA (US); Jonathan Farringdon, Pittsburgh, PA (US); Raymond Pelletier, Pittsburgh, PA (US)

(73) Assignee: BodyMedia, Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/682,759

(22) Filed: Oct. 9, 2003

(65) Prior Publication Data

US 2004/0152957 A1 Aug. 5, 2004

Related U.S. Application Data

(63) Continuation-in-part of application No. 09/923,181, filed on Aug. 6, 2001, which is a continuation-in-part of application No. 09/602,537, filed on Jun. 23, 2000, now Pat. No. 6,605,038, which is a continuation-in-part of application No. 09/595,660, filed on Jun. 16, 2000.

(60) Provisional application No. 60/417,163, filed on Oct. 9, 2002.

(51) Int. Cl.
*A61B 5/00* (2006.01)

(52) U.S. Cl. ............... 600/300; 128/905; 128/920; 600/301

(58) Field of Classification Search ........ 600/300–301, 600/587–595, 481, 500, 532, 529; 128/897–898, 128/903, 904, 920–921; 705/2–4; 340/539.1, 340/573.1–573.3; 482/4–9

See application file for complete search history.

(56) References Cited

U.S. PATENT DOCUMENTS 4,031,365 A 6/1977 Raggiotti et al.

(Continued)

FOREIGN PATENT DOCUMENTS

DE 198 32 361 A1 2/2000

(Continued)

OTHER PUBLICATIONS

Georgia Tech. "Smart T-shirt," Georgia Institute of Technology Press Release, Nov. 14, 1997.

(Continued)

*Primary Examiner*—Max F. Hindenburg
*Assistant Examiner*—Michael C Astorino
(74) *Attorney, Agent, or Firm*—Metz Lewis LLC; Barry I. Friedman

(57) ABSTRACT

A monitoring apparatus that includes a sensor device and an I/O device in communication with the sensor device that generates derived data using the data from the sensor device. The derived data cannot be directly detected by the associated sensors. Alternatively, an apparatus that includes a wearable sensor device and an I/O device in communication with the sensor device that includes means for displaying information and a dial for entering information. Alternatively, an apparatus for tracking caloric consumption and caloric expenditure data that includes a sensor device and an I/O device in communication with the sensor device. The sensor device includes a processor programmed to generate data relating to caloric expenditure from sensor data. Alternatively, an apparatus for tracking caloric information for an individual that utilizes a plurality of classification identifiers for classifying meals consumed by the individual, each of the classification identifiers having a corresponding caloric amount.

39 Claims, 47 Drawing Sheets

U.S. PATENT DOCUMENTS

| | | |
|---|---|---|
| 4,052,979 A | 10/1977 | Scherr et al. |
| 4,129,125 A | 12/1978 | Lester et al. |
| 4,148,304 A | 4/1979 | Mull |
| 4,151,831 A | 5/1979 | Lester |
| 4,192,000 A | 3/1980 | Lipsey |
| 4,364,398 A | 12/1982 | Sassi et al. |
| 4,377,171 A | 3/1983 | Wada |
| 4,407,295 A | 10/1983 | Steuer et al. |
| 4,488,558 A | 12/1984 | Simbruner et al. |
| 4,509,531 A | 4/1985 | Ward |
| 4,531,527 A | 7/1985 | Reinhold, Jr. et al. |
| 4,539,994 A | 9/1985 | Baumbach et al. |
| 4,557,273 A | 12/1985 | Stoller et al. |
| 4,608,987 A | 9/1986 | Mills |
| 4,622,979 A | 11/1986 | Katchis et al. |
| 4,672,977 A | 6/1987 | Kroll |
| 4,676,254 A | 6/1987 | Frohn |
| 4,757,453 A | 7/1988 | Nasiff |
| RE32,758 E | 10/1988 | Zartmann |
| 4,784,162 A | 11/1988 | Ricks et al. |
| 4,803,625 A | 2/1989 | Fu et al. |
| 4,819,860 A | 4/1989 | Hargrove et al. |
| 4,827,943 A | 5/1989 | Bornn et al. |
| 4,828,257 A | 5/1989 | Dyer et al. |
| 4,883,063 A | 11/1989 | Bernard et al. |
| 4,891,756 A | 1/1990 | Williams, III |
| 4,917,108 A | 4/1990 | Mault |
| 4,958,645 A | 9/1990 | Cadell et al. |
| 4,966,154 A | 10/1990 | Cooper et al. |
| 4,981,139 A | 1/1991 | Pfohl |
| 5,007,427 A | 4/1991 | Suzuki et al. |
| 5,012,411 A | 4/1991 | Policastro |
| 5,027,824 A | 7/1991 | Dougherty et al. |
| 5,038,792 A | 8/1991 | Mault |
| 5,040,541 A | 8/1991 | Poppendiek |
| 5,050,612 A | 9/1991 | Matsumura |
| 5,072,458 A | 12/1991 | Suzuki |
| 5,111,818 A | 5/1992 | Suzuki et al. |
| 5,135,311 A | 8/1992 | Alpert |
| 5,148,002 A | 9/1992 | Kuo et al. |
| 5,178,155 A | 1/1993 | Mault |
| 5,179,958 A | 1/1993 | Mault |
| 5,216,599 A | 6/1993 | Uebe et al. |
| 5,224,479 A | 7/1993 | Sekine |
| 5,263,491 A | 11/1993 | Thornton |
| 5,285,398 A | 2/1994 | Janik |
| 5,305,244 A | 4/1994 | Newman et al. |
| 5,335,664 A | 8/1994 | Nagashima |
| 5,353,793 A | 10/1994 | Bornn |
| 5,410,471 A | 4/1995 | Alyfuku et al. |
| 5,435,315 A | 7/1995 | McPhee et al. |
| 5,445,149 A | 8/1995 | Rotolo et al. |
| 5,458,123 A | 10/1995 | Unger |
| 5,474,090 A | 12/1995 | Begun et al. |
| 5,484,389 A | 1/1996 | Stark et al. |
| 5,491,651 A | 2/1996 | Janik |
| 5,511,553 A | 4/1996 | Segalowitz |
| 5,515,858 A | 5/1996 | Myllymaki |
| 5,515,865 A | 5/1996 | Scanlon |
| 5,523,730 A | 6/1996 | Van Zeeland |
| 5,524,618 A | 6/1996 | Pottgen et al. |
| 5,555,490 A | 9/1996 | Carroll |
| 5,559,497 A | 9/1996 | Hong |
| 5,566,679 A | 10/1996 | Herriott |
| 5,581,238 A | 12/1996 | Chang et al. |
| 5,581,492 A | 12/1996 | Janik |
| 5,583,758 A | 12/1996 | McIlroy et al. |
| 5,611,085 A | 3/1997 | Rasmussen |
| 5,617,477 A | 4/1997 | Boyden |
| 5,622,180 A | 4/1997 | Tammi et al. |
| 5,645,068 A | 7/1997 | Mezack et al. |
| 5,663,703 A | 9/1997 | Pearlman et al. |
| 5,666,096 A | 9/1997 | Van Zeeland |
| 5,670,944 A | 9/1997 | Myllymaki |
| 5,673,691 A | 10/1997 | Abrams et al. |
| 5,673,692 A | 10/1997 | Schulze et al. |
| 5,686,516 A | 11/1997 | Tzur |
| 5,687,734 A | 11/1997 | Dempsey et al. |
| 5,697,791 A | 12/1997 | Nashner et al. |
| 5,704,350 A | 1/1998 | Williams, III |
| 5,719,743 A | 2/1998 | Jenkins et al. |
| 5,724,025 A | 3/1998 | Tavori |
| 5,726,631 A | 3/1998 | Lin |
| 5,730,140 A | 3/1998 | Fitch |
| 5,738,104 A | 4/1998 | Lo et al. |
| 5,741,217 A | 4/1998 | Gero |
| 5,752,976 A | 5/1998 | Duffin et al. |
| 5,771,001 A | 6/1998 | Cobb |
| 5,778,882 A | 7/1998 | Raymond et al. |
| 5,798,907 A | 8/1998 | Janik |
| 5,803,915 A | 9/1998 | Kremenchugsky et al. |
| 5,813,766 A | 9/1998 | Chen |
| 5,813,994 A | 9/1998 | Pottgen et al. |
| 5,823,975 A | 10/1998 | Stark et al. |
| 5,827,180 A | 10/1998 | Goodman |
| 5,828,943 A | 10/1998 | Brown |
| 5,832,296 A | 11/1998 | Wang et al. |
| 5,832,448 A | 11/1998 | Brown |
| 5,836,300 A | 11/1998 | Mault |
| 5,853,005 A | 12/1998 | Scanlon |
| 5,855,550 A | 1/1999 | Lai et al. |
| 5,857,939 A | 1/1999 | Kaufman |
| 5,857,967 A | 1/1999 | Frid et al. |
| 5,862,803 A | 1/1999 | Besson et al. |
| 5,865,733 A | 2/1999 | Malinouskas et al. |
| 5,868,669 A | 2/1999 | Iliff |
| 5,868,671 A | 2/1999 | Mahoney |
| 5,871,451 A | 2/1999 | Unger et al. |
| 5,876,350 A | 3/1999 | Lo et al. |
| 5,879,163 A | 3/1999 | Brown et al. |
| 5,879,309 A | 3/1999 | Johnson et al. |
| 5,884,198 A | 3/1999 | Kese et al. |
| 5,888,172 A | 3/1999 | Andrus et al. |
| 5,897,493 A | 4/1999 | Brown |
| 5,899,855 A | 5/1999 | Brown |
| 5,902,250 A | 5/1999 | Verrier et al. |
| 5,908,396 A | 6/1999 | Hayakawa et al. |
| 5,912,865 A | 6/1999 | Ortega |
| 5,913,310 A | 6/1999 | Brown |
| 5,919,141 A | 7/1999 | Money et al. |
| 5,929,782 A | 7/1999 | Stark et al. |
| 5,933,136 A | 8/1999 | Brown |
| 5,941,837 A | 8/1999 | Amano et al. |
| 5,951,300 A | 9/1999 | Brown |
| 5,956,501 A | 9/1999 | Brown |
| 5,959,611 A | 9/1999 | Smailagic et al. |
| 5,960,403 A | 9/1999 | Brown |
| 5,976,083 A | 11/1999 | Richardson et al. |
| 5,990,772 A | 11/1999 | Van Zeeland |
| 6,032,119 A | 2/2000 | Brown et al. |
| 6,047,203 A | 4/2000 | Sackner et al. |
| 6,053,872 A | 4/2000 | Mohler |
| 6,059,692 A | 5/2000 | Hickman |
| 6,067,468 A | 5/2000 | Korenman et al. |
| 6,069,552 A | 5/2000 | Van Zeeland |
| 6,091,973 A | 7/2000 | Colla et al. |
| 6,101,407 A | 8/2000 | Groezinger |
| 6,101,478 A | 8/2000 | Brown |
| 6,135,107 A | 10/2000 | Mault |
| 6,138,079 A | 10/2000 | Putnam |
| 6,154,668 A | 11/2000 | Pedersen et al. |
| 6,168,563 B1 | 1/2001 | Brown |
| 6,184,797 B1 | 2/2001 | Stark et al. |
| 6,198,394 B1 | 3/2001 | Jacobsen et al. |

| | | |
|---|---|---|
| 6,208,900 B1 | 3/2001 | Ecker et al. |
| 6,225,901 B1 | 5/2001 | Kail, IV |
| 6,225,980 B1 | 5/2001 | Weiss et al. |
| 6,247,647 B1 | 6/2001 | Courtney et al. |
| 6,248,065 B1 | 6/2001 | Brown |
| 6,251,048 B1 | 6/2001 | Kaufman |
| 6,265,978 B1 | 7/2001 | Atlas |
| 6,285,897 B1 | 9/2001 | Kilcoyne et al. |
| 6,290,646 B1 | 9/2001 | Cosentino et al. |
| 6,290,650 B1 | 9/2001 | Butterfield et al. |
| 6,292,698 B1 | 9/2001 | Duffin et al. |
| 6,298,218 B1 | 10/2001 | Lowe et al. |
| 6,305,071 B1 | 10/2001 | Van Zeeland |
| 6,306,088 B1 | 10/2001 | Krausman et al. |
| 6,312,363 B1 | 11/2001 | Watterson et al. |
| 6,315,719 B1 | 11/2001 | Rode et al. |
| 6,336,900 B1 | 1/2002 | Alleckson et al. |
| 6,339,720 B1 | 1/2002 | Anzellini et al. |
| 6,341,229 B1 | 1/2002 | Akiva |
| 6,364,834 B1 | 4/2002 | Reuss et al. |
| 6,366,871 B1 | 4/2002 | Geva |
| 6,368,287 B1 | 4/2002 | Hadas |
| 6,371,123 B1 | 4/2002 | Stark et al. |
| 6,377,162 B1 | 4/2002 | Delestienne et al. |
| 6,385,473 B1 | 5/2002 | Haines et al. |
| 6,392,515 B1 | 5/2002 | Van Zeeland et al. |
| 6,416,471 B1 | 7/2002 | Kumar et al. |
| 6,420,959 B1 | 7/2002 | Lizzi |
| 6,450,922 B1 | 9/2002 | Henderson et al. |
| 6,450,953 B1 | 9/2002 | Place et al. |
| 6,454,708 B1 | 9/2002 | Ferguson et al. |
| 6,466,232 B1 | 10/2002 | Newell et al. |
| 6,468,222 B1 | 10/2002 | Mault et al. |
| 6,478,736 B1 | 11/2002 | Mault |
| 6,494,829 B1 | 12/2002 | New, Jr. et al. |
| 6,513,532 B2 | 2/2003 | Mault et al. |
| 6,527,711 B1 | 3/2003 | Stivoric et al. |
| 6,532,381 B2 | 3/2003 | Bayer et al. |
| 6,547,745 B1 | 4/2003 | Rubinstein et al. |
| 6,551,251 B2 | 4/2003 | Zuckerwar et al. |
| 6,553,251 B1 | 4/2003 | Lahdesmaki |
| 6,571,200 B1 | 5/2003 | Mault |
| 6,584,344 B2 | 6/2003 | Hannula |
| 6,595,929 B2 | 7/2003 | Stivoric et al. |
| 6,597,944 B1 | 7/2003 | Hadas |
| 6,605,038 B1 | 8/2003 | Teller et al. |
| 6,610,012 B2 | 8/2003 | Mault |
| 6,656,125 B2 | 12/2003 | Misczynski et al. |
| 6,665,559 B2 | 12/2003 | Rowlandson |
| 6,690,959 B2 | 2/2004 | Thompson |
| 6,712,615 B2 | 3/2004 | Martin |
| 6,734,802 B2 | 5/2004 | Halleck et al. |
| 6,755,795 B2 | 6/2004 | Mammaropoulos et al. |
| 6,790,178 B1 * | 9/2004 | Mault et al. ............ 600/300 |
| 6,808,473 B2 | 10/2004 | Hisano et al. |
| 6,842,877 B2 | 1/2005 | Robarts et al. |
| 6,852,085 B2 | 2/2005 | Rubinstein |
| 6,874,127 B2 | 3/2005 | Newell et al. |
| 6,920,348 B2 | 7/2005 | Vasin et al. |
| 6,968,375 B1 | 11/2005 | Brown |
| 2001/0029340 A1 | 10/2001 | Mault et al. |
| 2001/0032059 A1 | 10/2001 | Kelly, Jr. et al. |
| 2001/0044581 A1 | 11/2001 | Mault |
| 2001/0049470 A1 | 12/2001 | Mault et al. |
| 2001/0056229 A1 | 12/2001 | Cosentino et al. |
| 2002/0019296 A1 | 2/2002 | Freeman et al. |
| 2002/0019586 A1 | 2/2002 | Teller |
| 2002/0028995 A1 | 3/2002 | Mault |
| 2002/0032386 A1 | 3/2002 | Sackner et al. |
| 2002/0107450 A1 | 8/2002 | Ogura |
| 2002/0111539 A1 | 8/2002 | Cosentino et al. |
| 2002/0128804 A1 | 9/2002 | Geva |
| 2002/0133378 A1 | 9/2002 | Mault et al. |
| 2003/0055460 A1 | 3/2003 | Owen et al. |
| 2003/0069510 A1 | 4/2003 | Semler |
| 2003/0083559 A1 | 5/2003 | Thompson |
| 2003/0176797 A1 | 9/2003 | Anzellini |
| 2005/0070778 A1 | 3/2005 | Lackey et al. |
| 2005/0226310 A1 | 10/2005 | Nakazawa et al. |

FOREIGN PATENT DOCUMENTS

| | | |
|---|---|---|
| DE | 199 11 766 A1 | 9/2000 |
| EP | 0670064 B1 | 11/1993 |
| EP | 0707825 A2 | 4/1996 |
| GB | 2322952 A | 5/1997 |
| WO | 93/01574 | 1/1993 |
| WO | 94/25841 | 11/1994 |
| WO | 97/06499 | 2/1997 |
| WO | 99/27483 | 11/1998 |
| WO | 00/11578 | 3/2000 |
| WO | 00/26882 | 5/2000 |
| WO | 00/32098 | 6/2000 |
| WO | 00/47108 | 8/2000 |
| WO | 00/51543 | 9/2000 |
| WO | 00/52604 | 9/2000 |
| WO | 01/28495 | 10/2000 |
| WO | 01/08554 | 2/2001 |
| WO | 01/26535 | 4/2001 |
| WO | 01/26547 | 4/2001 |
| WO | 01/28416 | 4/2001 |
| WO | 01/39089 | 5/2001 |
| WO | 01/52718 | 7/2001 |
| WO | 01/56454 | 9/2001 |
| WO | 01/82783 | 11/2001 |
| WO | 01/82789 | 11/2001 |
| WO | 01/89365 | 11/2001 |
| WO | 01/89368 | 11/2001 |
| WO | 02/069798 | 9/2002 |

OTHER PUBLICATIONS

Personal Health Monitor for Homes, Time Tuomisto & Vesa Pentikainen, ERCIM News, No. 29, Apr. 1997.

CYBeR-CARE Internet Healthcare Technologies, BW Health Wire, Oct. 7, 1999.

"Nearer to the Heart," Brianna Krebs, Washington Post, Jan. 17, 1999.

"Portable Sensor Provides Remote Monitoring of Heart", Nikkei Weekly, Oct. 27, 1998.

"FDA Clears Dates-Ohmeda Pulse Oximeter," BW Health Wire, Dec. 3, 1998.

"Estee Soft New Version of LifeConnect," Business Wire, Jan. 20, 1999.

Matsushita Home Health Check System, The Nihon Keizai Shimbun, Dec. 17, 1998.

Warfighter Physiological Status Monitoring, MOMRP Fact Sheet No. 6, USAMRMC (1999) (downloaded from www.momrp.org).

"The H.J. Andrews Climatological Field Measurement Program," Henshaw, D. , Aug. 9, 1997 (downloaded fr m www.fsl.orst.edu).

"Ironman Speed and Distance System" (downloaded from www. timex.com), Timex, Oct. 4, 2002.

"Ironman Speed Distance System—Once Again Timex Revolutionizes the Sportwatch" (downloaded from www.timex.com), Timex, Jan. 8, 2002.

Polar M91ti Heart Rate Monitor Users Manual—Quick Guide, Polar Electro Inc., Nov. 2000.

Polar USA—Product Detail—M91ti (downloaded from www. polarusa.com), Polar USA, Oct. 4, 2002.

Polar USA—Product Detail—S-610 (downloaded from www. polarusa.com), Polar USA, Oct. 4, 2002.

Thermal Gap Fillers, Kent Young, (article downloaded from www. chomerics.com), Feb. 6, 2001.

Therm-A-Gap, Chromerics Technical Bulletin 70, Feb. 6, 2001.

CoolPoly, the Original Thermally Conductive Polymer, (article downloaded from www.coolpolymers.com), Feb. 7, 2001.

Micro-Foil Heat Flux Sensors, RdF Corporation Catalog No. HFS-A, Mar. 1998.

Industrial Micro-Foil Heat Flux Sensor, RdF CORPORATION Datasheet No. HFS-B, Oct. 1995.

Industrial/Commercial Micro-Foil Heat Flux Sensor, RdF CORPORATION Catalog No. HFS-C, Dec. 1999.

Lightweight Ambulatory Physiological Monitoring System, Ames Research Center, Moffett Field, CA (undated).

Weight Watchres TurnAround, Weight Watchers (downloaded from www.weightwatchers.com), 2004.

Jenny Craig Weight Loss Programs, Jenny Craig (downloaded from www.jennycraig.com), 2004.

The Complete Nutrition and Weight Management Solution Based on Your Unique Metabolic Fingerprint & Goals, BALANCELOG, (downloaded from www.healthetech.com), 2004.

What is FitDay?, FITDAY (downloaded from www.fitday.com), 2004.

A combined heart rate and movement sensor: proof of concept and preliminary testing study, K. Rennie, T. Rowsell, S.A. Jebb, D. Holburn & N.J. Wareham, 2004.

* cited by examiner

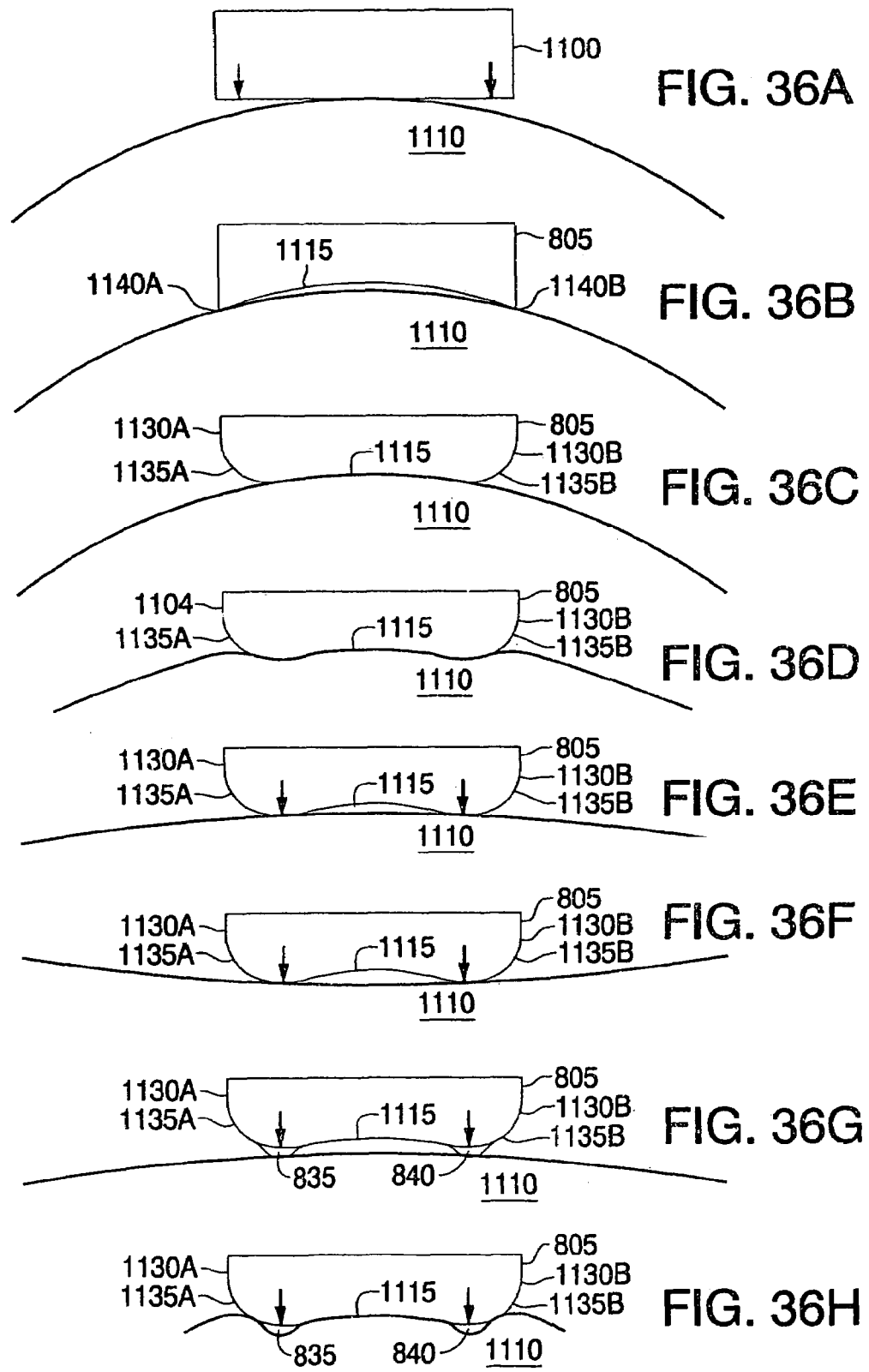

APPARATUS FOR DETECTING, RECEIVING, DERIVING AND DISPLAYING HUMAN PHYSIOLOGICAL AND CONTEXTUAL INFORMATION

CROSS REFERENCE TO A RELATED APPLICATIONS

This application claims the benefit of U.S. Provisional Application No. 60/417,163 filed on Oct. 9, 2002 and is a continuation-in-part of U.S. application Ser. No. 09/923,181, filed on Aug. 6, 2001, which is a continuation-in-part of U.S. application Ser. No. 09/602,537, filed on Jun. 23, 2000, now U.S. Pat. No. 6,605,038, which is a continuation-in-part of U.S. application Ser. No. 09/595,660, filed on Jun. 16, 2000.

FIELD OF THE INVENTION

The present invention relates to an apparatus which includes one or more sensors for collecting data relating to an individual's physiological state and various contextual parameters and a data input and output device for enabling the individual to enter information and for displaying information to the individual. In particular, the invention, according to one aspect, relates to an apparatus and method for tracking caloric consumption and/or caloric expenditure of an individual.

BACKGROUND OF THE INVENTION

Research has shown that a large number of the top health problems in society are either caused in whole or in part by an unhealthy lifestyle. More and more, our society requires people to lead fast-paced, achievement-oriented lifestyles that often result in poor eating habits, high stress levels, lack of exercise, poor sleep habits and the inability to find the time to center the mind and relax. Recognizing this fact, people are becoming increasingly interested in establishing a healthier lifestyle.

Traditional medicine, embodied in the form of an HMO or similar organizations, does not have the time, the training, or the reimbursement mechanism to address the needs of those individuals interested in a healthier lifestyle. There have been several attempts to meet the needs of these individuals, including a perfusion of fitness programs and exercise equipment, dietary plans, self-help books, alternative therapies, and most recently, a plethora of health information web sites on the Internet. Each of these attempts are targeted to empower the individual to take charge and get healthy. Each of these attempts, however, addresses only part of the needs of individuals seeking a healthier lifestyle and ignores many of the real barriers that most individuals face when trying to adopt a healthier lifestyle. These barriers include the fact that the individual is often left to himself or herself to find motivation, to implement a plan for achieving a healthier lifestyle, to monitor progress, and to brainstorm solutions when problems arise; the fact that existing programs are directed to only certain aspects of a healthier lifestyle, and rarely come as a complete package; and the fact that recommendations are often not targeted to the unique characteristics of the individual or his life circumstances.

SUMMARY OF THE INVENTION

The present invention relates to an apparatus for monitoring human status parameters that includes a sensor device in electronic communication with at least one sensor adapted to generate data indicative of at least a first parameter of the individual and an I/O device in electronic communication with the sensor device. The I/O device receives the data indicative of at least a first parameter from the sensor device and data indicative of a second parameter of the individual generated by a second sensor. At least one of the first parameter and the second parameter are physiological. The I/O device generates derived data using the data indicative of at least a first parameter and the data indicative of a second parameter, wherein the derived data comprises a third parameter of the individual that is an individual status parameter that cannot be directly detected by the at least one sensor or the second sensor. The I/O device further includes means for displaying information based on the third parameter.

The I/O device may further include means for enabling the individual to enter information relating to the individual into the I/O device. The third parameter of the individual may any one of physical activity, sleep activity, nutrition activity, mind centering activity, stress level, metabolic rate, and oxygen consumption rate. Specifically, the third parameter may be data relating to caloric expenditure of said individual. In such an embodiment, the I/O device may include means for enabling the individual to enter information relating to calories consumed by the individual, and the I/O device may generate caloric consumption data using the information relating to calories consumed. Information based on the caloric expenditure data and the caloric consumption data, such as energy balance data, a rate of weight loss or gain, or information relating to one or more goals of said individual may then be displayed. The third parameter may also includes data relating to caloric consumption of said individual. In any embodiment, the information entered into the I/O device may also be used to generate the derived data.

In the apparatus, at least one of the at least one sensor and the second sensor may be a contextual sensor. In addition, the I/O device may further comprise a processor for generating the derived data. Alternatively, the may further comprise a computing device having a processor in electronic communication with the I/O device, wherein the I/O device generates the derived data by communicating the data indicative of at least a first parameter and the data indicative of a second parameter to the computing device and receiving the derived data from the computing device, wherein the processor of the computing device generates the derived data.

In an alternate embodiment, the present invention relates to an apparatus for detecting at least one of human physiological and contextual information from the body of a wearer that includes a sensor device adapted to be worn on the body having one or more sensors selected from the group consisting of physiological sensors and contextual sensors and an I/O device in electronic communication with said sensor device. The I/O device includes means for displaying information and a dial, the dial being supported for rotational movement about an external surface of the I/O device. The dial enables the wearer to enter information into the I/O device. The I/O device may further include at least one button that also enables the wearer to enter information into the I/O device. The I/O device may also have access to a database of reference data, with the dial and the at least one button being used to access portions of said reference data.

In one embodiment, the sensor device has a processing unit in electronic communication with and receiving one or more signals from the one or more sensors. The processing unit generates data indicative of calories expended by the wearer from at least one of the one or more signals, the data indicative of calories expended being transmitted from the sensor device to the I/O device. The information entered by the wearer in this embodiment includes data relating to calories consumed by the wearer. The apparatus displays caloric expenditure data and caloric consumption data, the caloric expenditure data being based on the data indicative of calories expended by said wearer and the caloric consumption data being based on the data relating to calories consumed by the wearer. The I/O device may have access to a database of food data including food items and associated caloric values, wherein the information is entered by the wearer by accessing and selecting specific pieces of the food data from said database.

The present invention also relates to an apparatus for tracking caloric consumption and caloric expenditure of an individual that includes a sensor device adapted to be worn on an individual's body and an I/O device in electronic communication with the sensor device. The sensor device includes a processor in electronic communication with at least two sensors, at least one sensor being a physiological sensor, the sensors being adapted to generate data indicative of at least a first parameter of the individual and a second parameter of the individual, the first parameter being physiological. The processor is programmed to generate data relating to caloric expenditure of the individual using the data indicative of a first parameter and a second parameter. The I/O device receives the caloric expenditure data from the sensor device. The I/O device includes means for enabling the individual to enter information relating to calories consumed by the individual, wherein the information relating to calories consumed is used to generate caloric consumption data. The I/O device further includes means for displaying information based on the caloric expenditure data and the caloric consumption data. The I/O device may have access to a database of food data comprising food items and associated caloric values, the database being used to generate the caloric consumption data. The displayed information may include energy balance data, a rate of weight loss or gain, or information relating to one or more goals of the individual. The at least two sensors may be included within the sensor device, or at least one of the sensors may located separately from the sensor device. At least one of the at least two sensors may be a contextual sensor. The I/O device may be adapted to display one or more suggestions for achieving one or more goals based on the caloric consumption data and the caloric expenditure data.

In yet another alternate embodiment, The present invention relates to an apparatus for tracking caloric information for an individual that includes means for displaying a plurality of classification identifiers for classifying meals consumed by the individual, each of the classification identifiers having a corresponding caloric amount, means for selecting, for each meal consumed by the individual, one of the classification identifiers, and a processor for generating and storing caloric consumption data for the individual based on the caloric amount corresponding to the classification identifier selected by the individual for each meal consumed by the individual. The corresponding caloric amounts may be generic amounts designed to suit the general public or may be tailored specifically for the individual. The corresponding caloric amounts maybe determined for each of the classification identifiers based on an algorithm, which may be a simple look-up table or may be more complicated in addition, the classification identifiers may each comprise an indication of an estimated size of a meal, such as S, M, L and XL, or may comprise a point value based on an estimated size of a meal. Alternatively, each of the classification identifiers may be comprise a plurality of point values forming a grid, each of the point values being based on an estimated size and caloric density associated with a meal. The apparatus may further comprise a sensor device adapted to be worn on the individual's body that generates data relating to caloric expenditure of the individual, the sensor device being in electronic communication with the processor. The processor receives the caloric expenditure data from the sensor device and generates information based on the caloric expenditure data and the caloric consumption data that may include energy balance data, a rate of weight loss or gain, or information relating to one or more goals of the individual. The sensor device may further include a second processor in electronic communication with at least two sensors, at least one sensor being a physiological sensor, the sensors being adapted to generate data indicative of at least a first parameter of the individual and a second parameter of the individual, the first parameter being physiological. The second processor is programmed to generate the caloric expenditure data using the data indicative of a first parameter and a second parameter. The apparatus may also further comprise a computing device having software for enabling the individual to enter one or more food items for each meal consumed by the individual and for associating a second caloric amount with the meal based on the food items. The processor in this embodiment receiving, for each meal consumed by the individual over a predetermined time period, the second caloric amounts and adjusting for each of the classification identifiers the corresponding caloric amount based on the second caloric amounts. The software may include a database of food data including the food items and the second caloric amounts.

BRIEF DESCRIPTION OF THE DRAWINGS

Further features and advantages of the present invention will be apparent upon consideration of the following detailed description of the present invention, taken in conjunction with the following drawings, in which like reference characters refer to like parts, and in which:

FIG. 36A is a cross-sectional view of a housing for a prior art sensor device;

FIGS. 36B through H are cross-sectional views of various embodiments of a housing for a sensor device according to an aspect of the present invention taken along lines D-D in FIG. 23;

DESCRIPTION OF THE PREFERRED EMBODIMENTS

Figure 1:
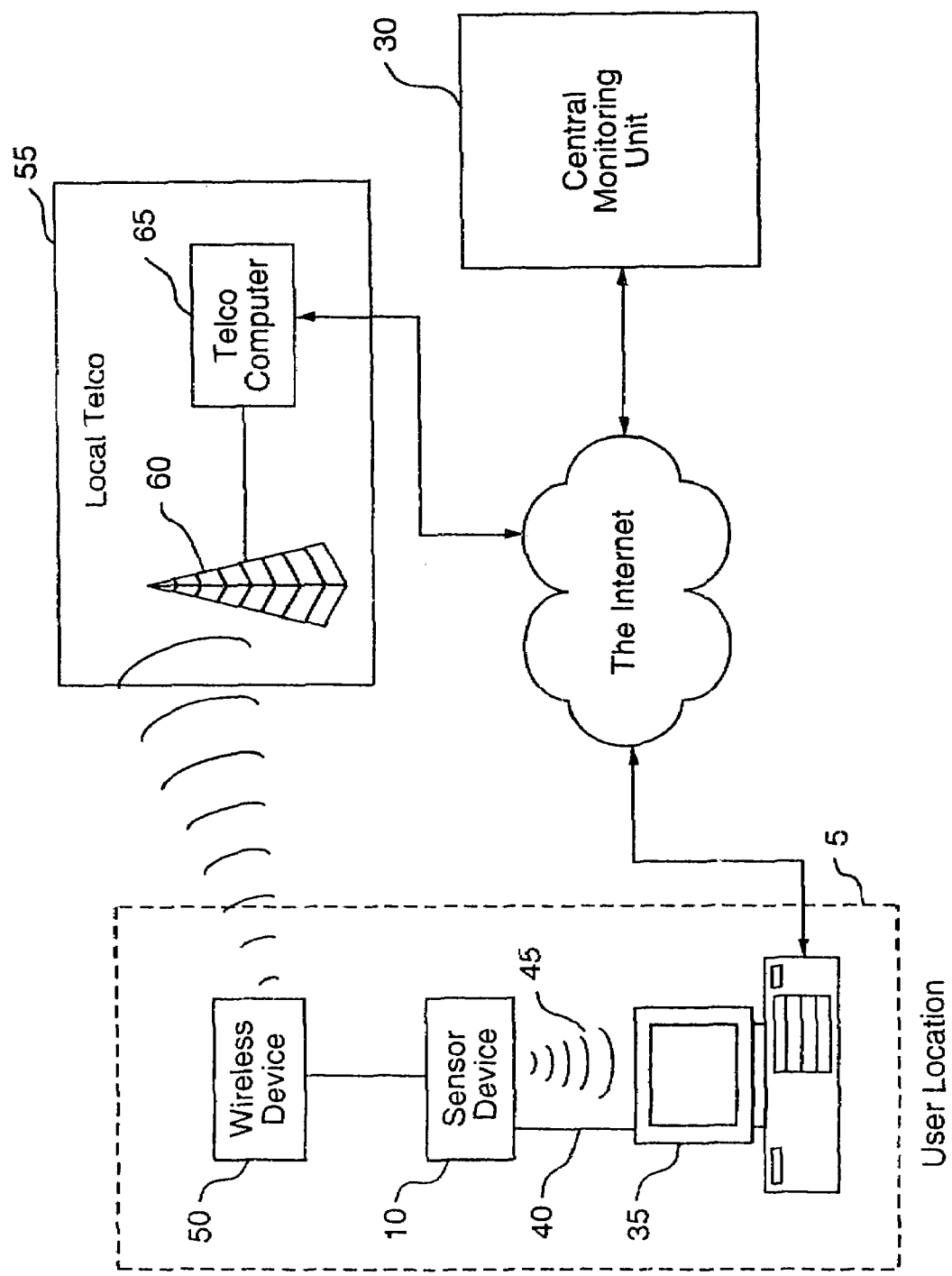
FIG. 1 is a diagram of an embodiment of a system for monitoring physiological data and lifestyle over an electronic network according to the present invention.

In general, according to the present invention, data relating to the physiological state, the lifestyle and certain contextual parameters of an individual is collected and transmitted, either subsequently or in real-time, to a site, preferably remote from the individual, where it is stored for later manipulation and presentation to a recipient, preferably over an electronic network such as the Internet. Contextual parameters as used herein means parameters relating to the environment, surroundings and location of the individual, including, but not limited to, air quality, sound quality, ambient temperature, global positioning and the like. Referring to FIG. 1, located at user location 5 is sensor device 10 adapted to be placed in proximity with at least a portion of the human body. Sensor device 10 is preferably worn by an individual user on his or her body, for example as part of a garment such as a form fitting shirt, or as part of an arm band or the like. Sensor device 10, includes one or more sensors, which are adapted to generate signals in response to physiological characteristics of an individual, and a microprocessor. Proximity as used herein means that the sensors of sensor device 10 are separated from the individual's body by a material or the like, or a distance such that the capabilities of the sensors are not impeded.

Sensor device 10 generates data indicative of various physiological parameters of an individual, such as the individual's heart rate, pulse rate, beat-to-beat heart variability, EKG or ECG, respiration rate, skin temperature, core body temperature, heat flow off the body, galvanic skin response or GSR, EMG, EEG, EOG, blood pressure, body fat, hydration level, activity level, oxygen consumption, glucose or blood sugar level, body position, pressure on muscles or bones, and UV radiation exposure and absorption. In certain cases, the data indicative of the various physiological parameters is the signal or signals themselves generated by the one or more sensors and in certain other cases the data is calculated by the microprocessor based on the signal or signals generated by the one or more sensors. Methods for generating data indicative of various physiological parameters and sensors to be used therefor are well known. Table 1 provides several examples of such well known methods and shows the parameter in question, the method used, the sensor device used, and the signal that is generated. Table 1 also provides an indication as to whether further processing based on the generated signal is required to generate the data.

TABLE 1

| Parameter | Method | Sensor | Signal | Further Processing |
|---|---|---|---|---|
| Heart Rate | EKG | 2 Electrodes | DC Voltage | Yes |
| Pulse Rate | BVP | LED Emitter and Optical Sensor | Change in Resistance | Yes |
| Beat-to-Beat Variability | Heart Rate | 2 Electrodes | DC Voltage | Yes |
| EKG | Skin Surface Potentials | 3-10 Electrodes | DC Voltage | No |
| Respiration Rate | Chest Volume Change | Strain Gauge | Change in Resistance | Yes |
| Skin Temperature | Surface Temperature Probe | Thermistors | Change in Resistance | Yes |
| Core Temperature | Esophageal or Rectal Probe | Thermistors | Change in Resistance | Yes |
| Heat Flow | Heat Flux | Thermopile | DC Voltage | Yes |
| Galvanic Skin Response | Skin Conductance | 2 Electrodes | Change in Resistance | No |
| EMG | Skin Surface Potentials | 3 Electrodes | DC Voltage | No |
| EEG | Skin Surface Potentials | Multiple Electrodes | DC Voltage | Yes |
| EOG | Eye Movement | Thin Film Piezoelectric Sensors | DC Voltage | Yes |
| Blood Pressure | Non-Invasive Korotkuff Sounds | Electronic Sphygromarometer | Change in Resistance | Yes |
| Body Fat | Body Impedance | 2 Active Electrodes | Change in Impedance | Yes |
| Activity in Interpreted G Shocks per Minute | Body Movement | Accelerometer | DC Voltage, Capacitance Changes | Yes |
| Oxygen Consumption | Oxygen Uptake | Electro-chemical | DC Voltage Change | Yes |
| Glucose Level | Non-Invasive | Electro-chemical | DC Voltage Change | Yes |
| Body Position (e.g. supine, erect, sitting) | N/A | Mercury Switch Array | DC Voltage Change | Yes |
| Muscle Pressure | N/A | Thin Film Piezoelectric Sensors | DC Voltage Change | Yes |

TABLE 1-continued

| Parameter | Method | Sensor | Signal | Further Processing |
|---|---|---|---|---|
| UV Radiation Absorption | N/A | UV Sensitive Photo Cells | DC Voltage Change | Yes |

The types of data listed in Table 1 are intended to be examples of the types of data that can be generated by sensor device 10. It is to be understood that other types of data relating to other parameters can be generated by sensor device 10 without departing from the scope of the present invention.

The microprocessor of sensor device 10 may be programmed to summarize and analyze the data. For example, the microprocessor can be programmed to calculate an average, minimum or maximum heart rate or respiration rate over a defined period of time, such as ten minutes. Sensor device 10 may be able to derive information relating to an individual's physiological state based on the data indicative of one or more physiological parameters. The microprocessor of sensor device 10 is programmed to derive such information using known methods based on the data indicative of one or more physiological parameters. Table 2 provides examples of the type of information that can be derived, and indicates some of the types of data that can be used therefor.

TABLE 2

| Derived Information | Data Used |
|---|---|
| Ovulation | Skin temperature, core temperature, oxygen consumption |
| Sleep onset/wake | Beat-to-beat variability, heart rate, pulse rate, respiration rate, skin temperature, core temperature, heat flow, galvanic skin response, EMG, EEG, EOG, blood pressure, oxygen consumption |
| Calories burned | Heart rate, pulse rate, respiration rate, heat flow, activity, oxygen consumption |
| Basal metabolic rate | Heart rate, pulse rate, respiration rate, heat flow, activity, oxygen consumption |
| Basal temperature | Skin temperature, core temperature |
| Activity level | Heart rate, pulse rate, respiration rate, heat flow, activity, oxygen consumption |
| Stress level | EKG, beat-to-beat variability, heart rate, pulse rate, respiration rate, skin temperature, heat flow, galvanic skin response, EMG, EEG, blood pressure, activity, oxygen consumption |
| Relaxation level | EKG, beat-to-beat variability, heart rate, pulse rate, respiration rate, skin temperature, heat flow, galvanic skin response, EMG, EEG, blood pressure, activity, oxygen consumption |
| Maximum oxygen consumption rate | EKG, heart rate, pulse rate, respiration rate, heat flow, blood pressure, activity, oxygen consumption |
| Rise time or the time it takes to rise from a resting rate to 85% of a target maximum | Heart rate, pulse rate, heat flow, oxygen consumption |
| Time in zone or the time heart rate was above 85% of a target maximum | Heart rate, pulse rate, heat flow, oxygen consumption |
| Recovery time or the time it takes heart rate to return to a resting rate after heart rate was above 85% of a target maximum | Heart rate, pulse rate, heat flow, oxygen consumption |

Additionally, sensor device 10 may also generate data indicative of various contextual parameters relating to the environment surrounding the individual. For example, sensor device 10 can generate data indicative of the air quality, sound level/quality, light quality or ambient temperature near the individual, or even the global positioning of the individual. Sensor device 10 may include one or more sensors for generating signals in response to contextual characteristics relating to the environment surrounding the individual, the signals ultimately being used to generate the type of data described above. Such sensors are well known, as are methods for generating contextual parametric data such as air quality, sound level/quality, ambient temperature and global positioning.

Figure 2:
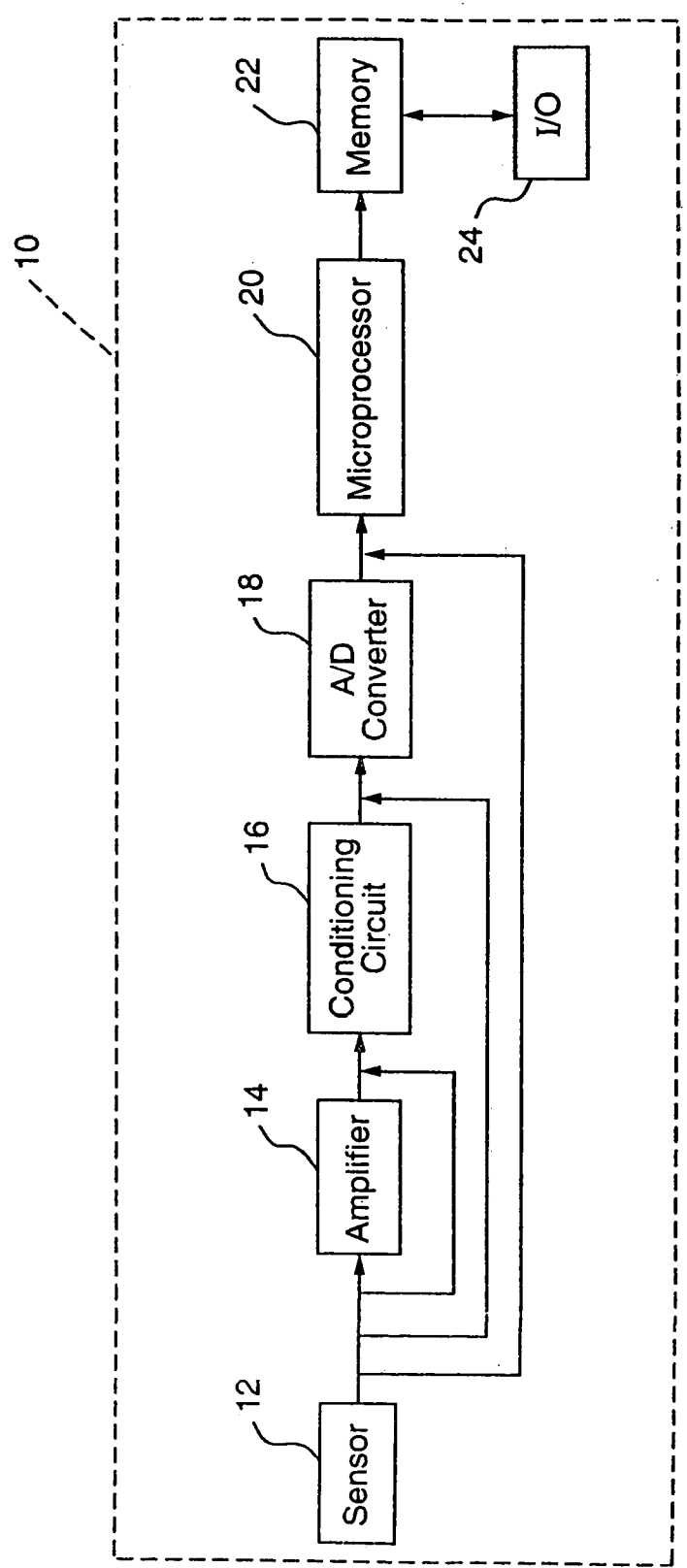
FIG. 2 is a block diagram of an embodiment of the sensor device shown in FIG. 1.

FIG. 2 is a block diagram of an embodiment of sensor device 10. Sensor device 10 includes at least one sensor 12 and microprocessor 20. Depending upon the nature of the signal generated by sensor 12, the signal can be sent through one or more of amplifier 14, conditioning circuit 16, and analog-to-digital converter 18, before being sent to microprocessor 20. For example, where sensor 12 generates an analog signal in need of amplification and filtering, that signal can be sent to amplifier 14, and then on to conditioning circuit 16, which may, for example, be a band pass filter. The amplified and conditioned analog signal can then be transferred to analog-to-digital converter 18, where it is converted to a digital signal. The digital signal is then sent to microprocessor 20. Alternatively, if sensor 12 generates a digital signal, that signal can be sent directly to microprocessor 20.

A digital signal or signals representing certain physiological and/or contextual characteristics of the individual user may be used by microprocessor 20 to calculate or generate data indicative of physiological and/or contextual parameters of the individual user. Microprocessor 20 is programmed to derive information relating to at least one aspect of the individual's physiological state. It should be understood that microprocessor 20 may also comprise other forms of processors or processing devices, such as a microcontroller, or any other device that can be programmed to perform the functionality described herein.

The data indicative of physiological and/or contextual parameters can, according to one embodiment of the present invention, be sent to memory 22, such as flash memory, where it is stored until uploaded in the manner to be described below. Although memory 22 is shown in FIG. 2 as a discrete element, it will be appreciated that it may also be part of microprocessor 20. Sensor device 10 also includes input/output circuitry 24, which is adapted to output and receive as input certain data signals in the manners to be described herein. Thus, memory 22 of the sensor device 10 will build up, over time, a store of data relating to the individual user's body and/or environment. That data is periodically uploaded from sensor device 10 and sent to remote central monitoring unit 30, as shown in FIG. 1, where it is stored in a database for subsequent processing and presentation to the user, preferably through a local or global electronic network such as the Internet. This uploading of data can be an automatic process that is initiated by sensor device 10 periodically or upon the happening of an event such as the detection by sensor device 10 of a heart rate below a certain level, or can be initiated by the individual user or some third party authorized by the user, preferably according to some periodic schedule, such as every day at 10:00 p.m. Alternatively, rather than storing data in memory 22, sensor device 10 may continuously upload data in real time.

The uploading of data from sensor device 10 to central monitoring unit 30 for storage can be accomplished in various ways. In one embodiment, the data collected by sensor device 10 is uploaded by first transferring the data to personal computer 35 shown in FIG. 1 by means of physical connection 40, which, for example, may be a serial connection such as an RS232 or USB port. This physical connection may also be accomplished by using a cradle, not shown, that is electronically coupled to personal computer 35 into which sensor device 10 can be inserted, as is common with many commercially available personal digital assistants. The uploading of data could be initiated by then pressing a button on the cradle or could be initiated automatically upon insertion of sensor device 10. The data collected by sensor device 10 may be uploaded by first transferring the data to personal computer 35 by means of short-range wireless transmission, such as infrared or RF transmission, as indicated at 45.

Once the data is received by personal computer 35, it is optionally compressed and encrypted by any one of a variety of well known methods and then sent out over a local or global electronic network, preferably the Internet, to central monitoring unit 30. It should be noted that personal computer 35 can be replaced by any computing device that has access to and that can transmit and receive data through the electronic network, such as, for example, a personal digital assistant such as the Palm VII sold by Palm, Inc., or the Blackberry 2-way pager sold by Research in Motion, Inc.

Alternatively, the data collected by sensor device 10, after being encrypted and, optionally, compressed by microprocessor 20, may be transferred to wireless device 50, such as a 2-way pager or cellular phone, for subsequent long distance wireless transmission to local telco site 55 using a wireless protocol such as e-mail or as ASCII or binary data. Local telco site 55 includes tower 60 that receives the wireless transmission from wireless device 50 and computer 65 connected to tower 60. According to the preferred embodiment, computer 65 has access to the relevant electronic network, such as the Internet, and is used to transmit the data received in the form of the wireless transmission to the central monitoring unit 30 over the Internet. Although wireless device 50 is shown in FIG. 1 as a discrete device coupled to sensor device 10, it or a device having the same or similar functionality may be embedded as part of sensor device 10.

Sensor device 10 may be provided with a button to be used to time stamp events such as time to bed, wake time, and time of meals. These time stamps are stored in sensor device 10 and are uploaded to central monitoring unit 30 with the rest of the data as described above. The time stamps may include a digitally recorded voice message that, after being uploaded to central monitoring unit 30, are translated using voice recognition technology into text or some other information format that can be used by central monitoring unit 30.

In addition to using sensor device 10 to automatically collect physiological data relating to an individual user, a kiosk could be adapted to collect such data by, for example, weighing the individual, providing a sensing device similar to sensor device 10 on which an individual places his or her hand or another part of his or her body, or by scanning the individual's body using, for example, laser technology or an iStat blood analyzer. The kiosk would be provided with processing capability as described herein and access to the relevant electronic network, and would thus be adapted to send the collected data to the central monitoring unit 30 through the electronic network. A desktop sensing device, again similar to sensor device 10, on which an individual places his or her hand or another part of his or her body may also be provided. For example, such a desktop sensing device could be a blood pressure monitor in which an individual places his or her arm. An individual might also wear a ring having a sensor device 10 incorporated therein. A base, not shown, could then be provided which is adapted to be coupled to the ring. The desktop sensing device or the base just described may then be coupled to a computer such as personal computer 35 by means of a physical or short range wireless connection so that the collected data could be uploaded to central monitoring unit 30 over the relevant electronic network in the manner described above. A mobile device such as, for example, a personal digital assistant, might also be provided with a sensor device 10 incorporated therein. Such a sensor device 10 would be adapted to collect data when mobile device is placed in proximity with the individual's body, such as by holding the device in the palm of one's hand, and upload the collected data to central monitoring unit 30 in any of the ways described herein.

Furthermore, in addition to collecting data by automatically sensing such data in the manners described above, individuals can also manually provide data relating to various life activities that is ultimately transferred to and stored at central monitoring unit 30. An individual user can access a web site maintained by central monitoring unit 30 and can directly input information relating to life activities by entering text freely, by responding to questions posed by the web site, or by clicking through dialog boxes provided by the web site. Central monitoring unit 30 can also be adapted to periodically send electronic mail messages containing questions designed to elicit information relating to life activities to personal computer 35 or to some other device that can receive electronic mail, such as a personal digital assistant, a pager, or a cellular phone. The individual would then provide data relating to life activities to central monitoring unit 30 by responding to the appropriate electronic mail message with the relevant data. Central monitoring unit 30 may also be adapted to place a telephone call to an individual user in which certain questions would be posed to the individual user. The user could respond to the questions by entering information using a telephone keypad, or by voice, in which case conventional voice recognition technology would be used by central monitoring unit 30 to receive and process the response. The telephone call may also be initiated by the user, in which case the user could speak to a person directly or enter information using the keypad or by voice/voice recognition technology. Central monitoring unit 30 may also be given access to a source of information controlled by the user, for example the user's electronic calendar such as that provided with the Outlook product sold by Microsoft Corporation of Redmond, Wash., from which it could automatically collect information. The data relating to life activities may relate to the eating, sleep, exercise, mind centering or relaxation, and/or daily living habits, patterns and/or activities of the individual. Thus, sample questions may include: What did you have for lunch today? What time did you go to sleep last night? What time did you wake up this morning? How long did you run on the treadmill today?

Feedback may also be provided to a user directly through sensor device 10 in a visual form, for example through an LED or LCD or by constructing sensor device 10, at least in part, of a thermochromatic plastic, in the form of an acoustic signal or in the form of tactile feedback such as vibration. Such feedback may be a reminder or an alert to eat a meal or take medication or a supplement such as a vitamin, to engage in an activity such as exercise or meditation, or to drink water when a state of dehydration is detected. Additionally, a reminder or alert can be issued in the event that a particular physiological parameter such as ovulation has been detected, a level of calories burned during a workout has been achieved or a high heart rate or respiration rate has been encountered.

As will be apparent to those of skill in the art, it may be possible to Adownload@ data from central monitoring unit 30 to sensor device 10. The flow of data in such a download process would be substantially the reverse of that described above with respect to the upload of data from sensor device 10. Thus, it is possible that the firmware of microprocessor 20 of sensor device 10 can be updated or altered remotely, i.e., the microprocessor can be reprogrammed, by downloading new firmware to sensor device 10 from central monitoring unit 30 for such parameters as timing and sample rates of sensor device 10. Also, the reminders/alerts provided by sensor device 10 may be set by the user using the web site maintained by central monitoring unit 30 and subsequently downloaded to the sensor device 10.

Figure 3:
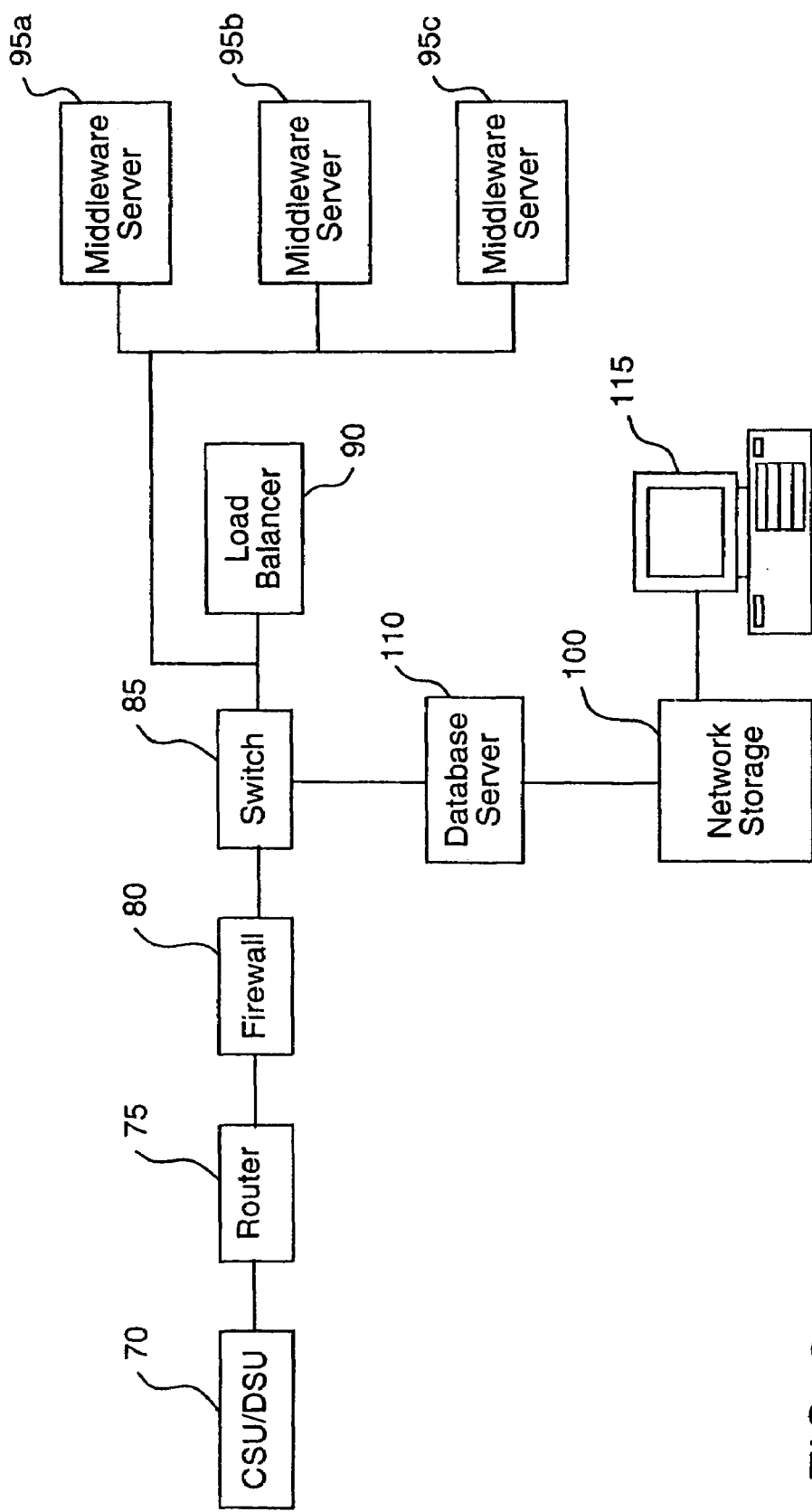
FIG. 3 is a block diagram of an embodiment of the central monitoring unit shown in FIG. 1.

Referring to FIG. 3, a block diagram of an embodiment of central monitoring unit 30 is shown. Central monitoring unit 30 includes CSU/DSU 70 which is connected to router 75, the main function of which is to take data requests or traffic, both incoming and outgoing, and direct such requests and traffic for processing or viewing on the web site maintained by central monitoring unit 30. Connected to router 75 is firewall 80. The main purpose of firewall 80 is to protect the remainder of central monitoring unit 30 from unauthorized or malicious intrusions. Switch 85, connected to firewall 80, is used to direct data flow between middleware servers 95a through 95c and database server 110. Load balancer 90 is provided to spread the workload of incoming requests among the identically configured middleware servers 95a through 95c. Load balancer 90, a suitable example of which is the F5 ServerIron product sold by Foundry Networks, Inc. of San Jose, Calif., analyzes the availability of each middleware server 95a through 95c, and the amount of system resources being used in each middleware server 95a through 95c, in order to spread tasks among them appropriately.

Central monitoring unit 30 includes network storage device 100, such as a storage area network or SAN, which acts as the central repository for data. In particular, network storage device 100 comprises a database that stores all data gathered for each individual user in the manners described above. An example of a suitable network storage device 100 is the Symmetrix product sold by EMC Corporation of Hopkinton, Mass. Although only one network storage device 100 is shown in FIG. 3, it will be understood that multiple network storage devices of various capacities could be used depending on the data storage needs of central monitoring unit 30. Central monitoring unit 30 also includes database server 110 which is coupled to network storage device 100. Database server 110 is made up of two main components: a large scale multiprocessor server and an enterprise type software server component such as the 8/8i component sold by Oracle Corporation of Redwood City, Calif., or the 5067 component sold by Microsoft Corporation of Redmond, Wash. The primary functions of database server 110 are that of providing access upon request to the data stored in network storage device 100, and populating network storage device 100 with new data. Coupled to network storage device 100 is controller 115, which typically comprises a desktop personal computer, for managing the data stored in network storage device 100.

Middleware servers 95a through 95c, a suitable example of which is the 22OR Dual Processor sold by Sun Microsystems, Inc. of Palo Alto, Calif., each contain software for generating and maintaining the corporate or home web page or pages of the web site maintained by central monitoring unit 30. As is known in the art, a web page refers to a block or blocks of data available on the World-Wide Web comprising a file or files written in Hypertext Markup Language or HTML, and a web site commonly refers to any computer on the Internet running a World-Wide Web server process. The corporate or home web page or pages are the opening or landing web page or pages that are accessible by all members of the general public that visit the site by using the appropriate uniform resource locator or URL. As is known in the art, URLs are the form of address used on the World-Wide Web and provide a standard way of specifying the location of an object, typically a web page, on the Internet. Middleware servers 95a through 95c also each contain software for generating and maintaining the web pages of the web site of central monitoring unit 30 that can only be accessed by individuals that register and become members of central monitoring unit 30. The member users will be those individuals who wish to have their data stored at central monitoring unit 30. Access by such member users is controlled using passwords for security purposes. Preferred embodiments of those web pages are described in detail below and are generated using collected data that is stored in the database of network storage device 100.

Middleware servers 95a through 95c also contain software for requesting data from and writing data to network storage device 100 through database server 110. When an individual user desires to initiate a session with the central monitoring unit 30 for the purpose of entering data into the database of network storage device 100, viewing his or her data stored in the database of network storage device 100, or both, the user visits the home web page of central monitoring unit 30 using a browser program such as Internet Explorer distributed by Microsoft Corporation of Redmond, Wash., and logs in as a registered user. Load balancer 90 assigns the user to one of the middleware servers 95a through 95c, identified as the chosen middleware server. A user will preferably be assigned to a chosen middleware server for each entire session. The chosen middleware server authenticates the user using any one of many well known methods, to ensure that only the true user is permitted to access the information in the database. A member user may also grant access to his or her data to a third party such as a health care provider or a personal trainer. Each authorized third party may be given a separate password and may view the member user's data using a conventional browser. It is therefore possible for both the user and the third party to be the recipient of the data.

When the user is authenticated, the chosen middleware server requests, through database server 110, the individual user's data from network storage device 100 for a predetermined time period. The predetermined time period is preferably thirty days. The requested data, once received from network storage device 100, is temporarily stored by the chosen middleware server in cache memory. The cached data is used by the chosen middleware server as the basis for presenting information, in the form of web pages, to the user again through the user's browser. Each middleware server 95a through 95c is provided with appropriate software for generating such web pages, including software for manipulating and performing calculations utilizing the data to put the data in appropriate format for presentation to the user. Once the user ends his or her session, the data is discarded from cache. When the user initiates a new session, the process for obtaining and caching data for that user as described above is repeated. This caching system thus ideally requires that only one call to the network storage device 100 be made per session, thereby reducing the traffic that database server 110 must handle. Should a request from a user during a particular session require data that is outside of a predetermined time period of cached data already retrieved, a separate call to network storage device 100 may be performed by the chosen middleware server. The predetermined time period should be chosen, however, such that such additional calls are minimized. Cached data may also be saved in cache memory so that it can be reused when a user starts a new session, thus eliminating the need to initiate a new call to network storage device 100.

As described in connection with Table 2, the microprocessor of sensor device 10 may be programmed to derive information relating to an individual's physiological state based on the data indicative of one or more physiological parameters. Central monitoring unit 30, and preferably middleware servers 95a through 95c, may also be similarly programmed to derive such information based on the data indicative of one or more physiological parameters.

It is also contemplated that a user will input additional data during a session, for example, information relating to the user's eating or sleeping habits. This additional data is preferably stored by the chosen middleware server in a cache during the duration of the user's session. When the user ends the session, this additional new data stored in a cache is transferred by the chosen middleware server to database server 110 for population in network storage device 100. Alternatively, in addition to being stored in a cache for potential use during a session, the input data may also be immediately transferred to database server 110 for population in network storage device 100, as part of a write-through cache system which is well known in the art.

Data collected by sensor device 10 shown in FIG. 1 is periodically uploaded to central monitoring unit 30. Either by long distance wireless transmission or through personal computer 35, a connection to central monitoring unit 30 is made through an electronic network, preferably the Internet. In particular, connection is made to load balancer 90 through CSU/DSU 70, router 75, firewall 80 and switch 85. Load balancer 90 then chooses one of the middleware servers 95a through 95c to handle the upload of data, hereafter called the chosen middleware server. The chosen middleware server authenticates the user using any one of many well known methods. If authentication is successful, the data is uploaded to the chosen middleware server as described above, and is ultimately transferred to database server 110 for population in the network storage device 100.

Figure 4:
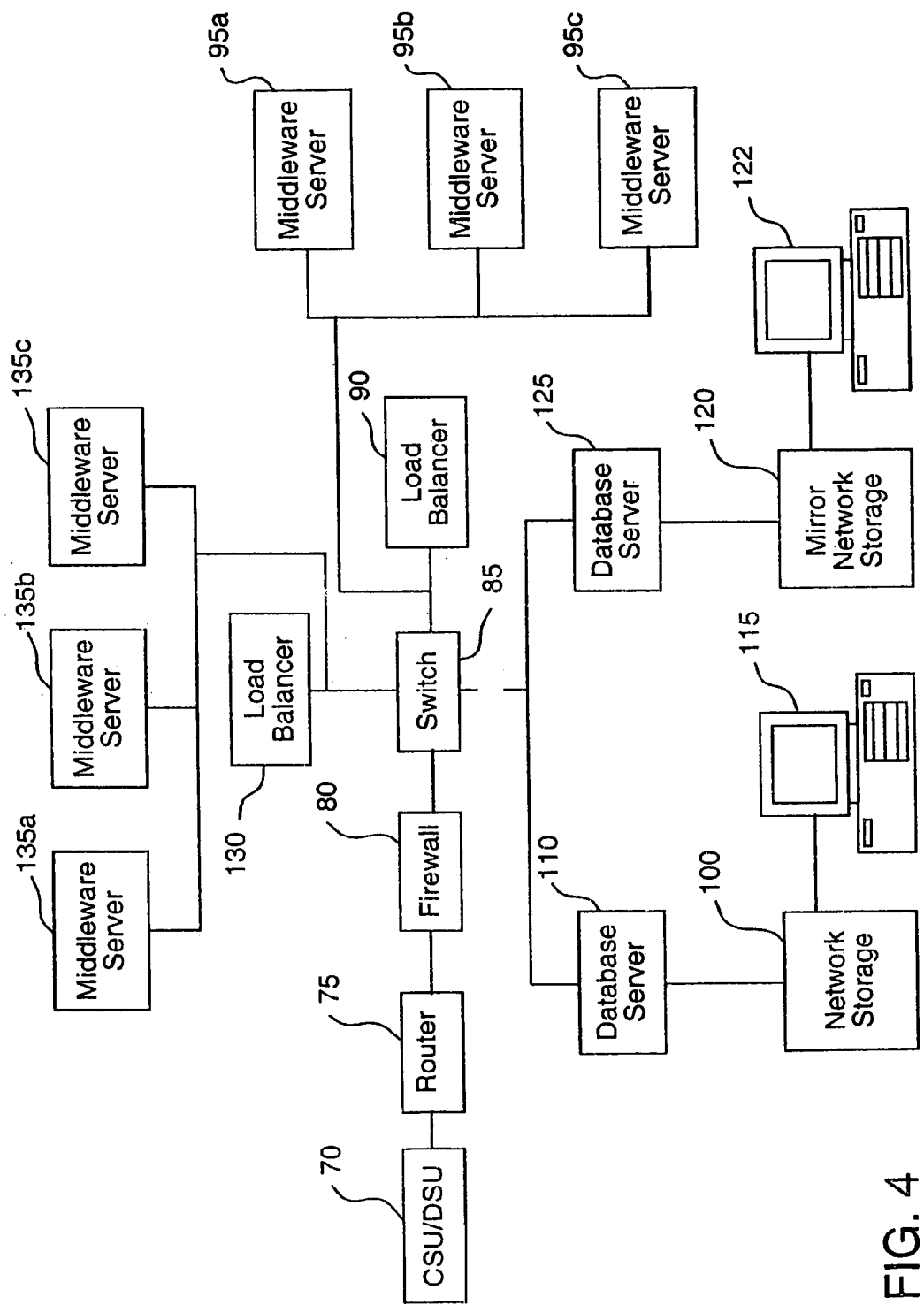
FIG. 4 is a block diagram of an alternate embodiment of the central monitoring unit shown in FIG. 1.

Referring to FIG. 4, an alternate embodiment of central monitoring unit 30 is shown. In addition to the elements shown and described with respect to FIG. 3, the embodiment of the central monitoring unit 30 shown in FIG. 4 includes a mirror network storage device 120 which is a redundant backup of network storage device 100. Coupled to mirror network storage device 120 is controller 122. Data from network storage device 100 is periodically copied to mirror network storage device 120 for data redundancy purposes.

Third parties such as insurance companies or research institutions may be given access, possibly for a fee, to certain of the information stored in mirror network storage device 120. Preferably, in order to maintain the confidentiality of the individual users who supply data to central monitoring unit 30, these third parties are not given access to such user's individual database records, but rather are only given access to the data stored in mirror network storage device 120 in aggregate form. Such third parties may be able to access the information stored in mirror network storage device 120 through the Internet using a conventional browser program. Requests from third parties may come in through CSU/DSU 70, router 75, firewall 80 and switch 85. In the embodiment shown in FIG. 4, a separate load balancer 130 is provided for spreading tasks relating to the accessing and presentation of data from mirror drive array 120 among identically configured middleware servers 135a through 135c. Middleware servers 135a through 135c each contain software for enabling the third parties to, using a browser, formulate queries for information from mirror network storage device 120 through separate database server 125. Middleware servers 135a through 135c also contain software for presenting the information obtained from mirror network storage device 120 to the third parties over the Internet in the form of web pages. In addition, the third parties can choose from a series of prepared reports that have information packaged along subject matter lines, such as various demographic categories.

As will be apparent to one of skill in the art, instead of giving these third parties access to the backup data stored in mirror network storage device 120, the third parties may be given access to the data stored in network storage device 100. Also, instead of providing load balancer 130 and middleware servers 135a through 135c, the same functionality, although at a sacrificed level of performance, could be provided by load balancer 90 and middleware servers 95a through 95c.

When an individual user first becomes a registered user or member, that user completes a detailed survey. The purposes of the survey are to: identify unique characteristics/circumstances for each user that they might need to address in order to maximize the likelihood that they will implement and maintain a healthy lifestyle as suggested by central monitoring unit 30; gather baseline data which will be used to set initial goals for the individual user and facilitate the calculation and display of certain graphical data output such as the Health Index pistons; identify unique user characteristics and circumstances that will help central monitoring unit 30 customize the type of content provided to the user in the Health Manager's Daily Dose; and identify unique user characteristics and circumstances that the Health Manager can guide the user to address as possible barriers to a healthy lifestyle through the problem-solving function of the Health Manager.

The specific information to be surveyed may include: key individual temperamental characteristics, including activity level, regularity of eating, sleeping, and bowel habits, initial response to situations, adaptability, persistence, threshold of responsiveness, intensity of reaction, and quality of mood; the user's level of independent functioning, i.e., self-organization and management, socialization, memory, and academic achievement skills; the user's ability to focus and sustain attention, including the user's level of arousal, cognitive tempo, ability to filter distractions, vigilance, and self-monitoring; the user's current health status including current weight, height, and blood pressure, most recent general physician visit, gynecological exam, and other applicable physician/healthcare contacts, current medications and supplements, allergies, and a review of current symptoms and/or health-related behaviors; the user's past health history, i.e., illnesses/surgeries, family history, and social stress events, such as divorce or loss of a job, that have required adjustment by the individual; the user's beliefs, values and opinions about health priorities, their ability to alter their behavior and, what might contribute to stress in their life, and how they manage it; the user's degree of self-awareness, empathy, empowerment, and self-esteem, and the user's current daily routines for eating, sleeping, exercise, relaxation and completing activities of daily living; and the user's perception of the temperamental characteristics of two key persons in their life, for example, their spouse, a friend, a co-worker, or their boss, and whether there are clashes present in their relationships that might interfere with a healthy lifestyle or contribute to stress.

Figure 5:
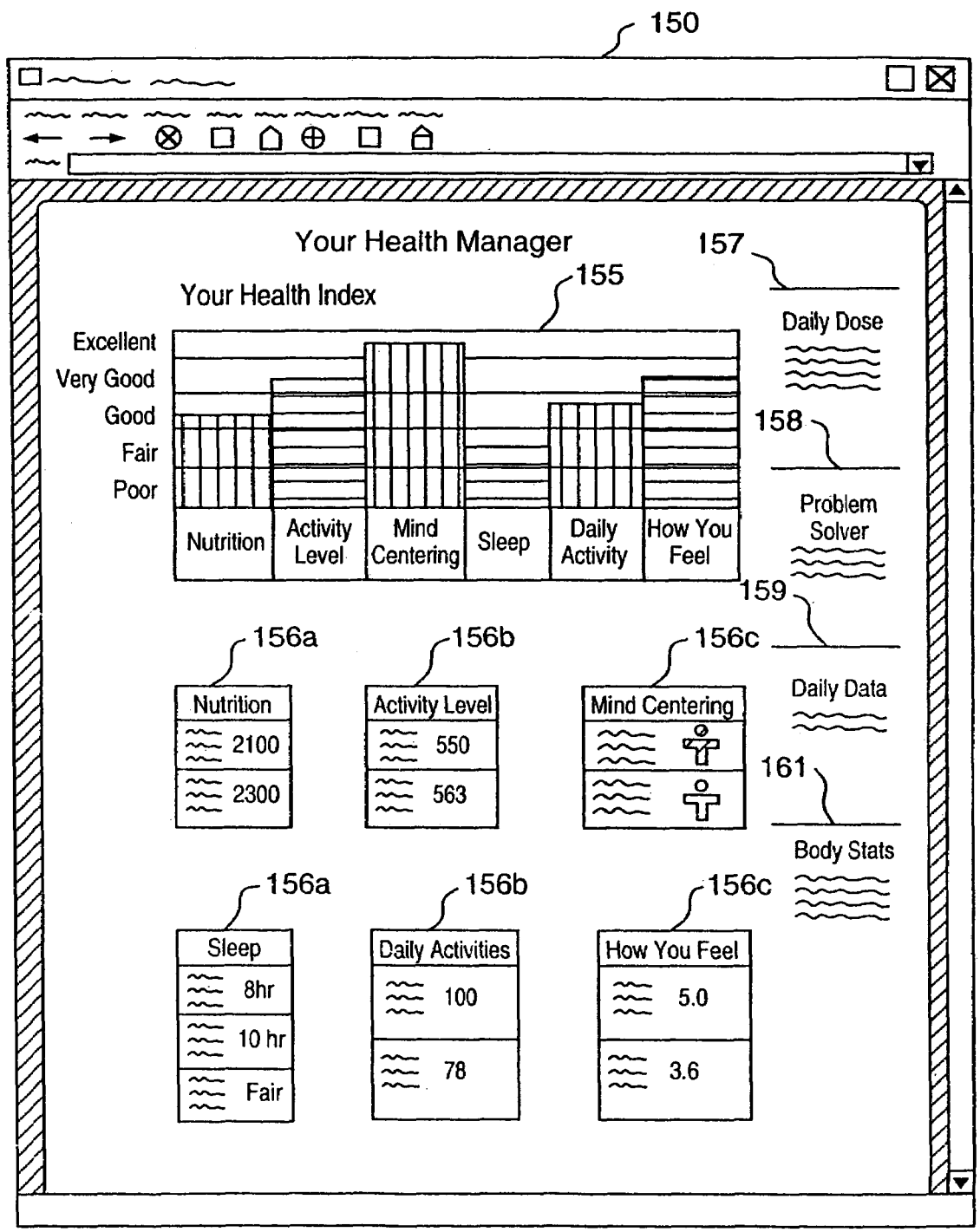
FIG. 5 is a representation of a preferred embodiment of the Health Manager web page according to an aspect of the present invention.

Each member user will have access, through the home web page of central monitoring unit 30, to a series of web pages customized for that user, referred to as the Health Manager. The opening Health Manager web page 150 is shown in FIG. 5. The Health Manager web pages are the main workspace area for the member user. The Health Manager web pages comprise a utility through which central monitoring unit 30 provides various types and forms of data, commonly referred to as analytical status data, to the user that is generated from the data it collects or generates, namely one or more of: the data indicative of various physiological parameters generated by sensor device 10; the data derived from the data indicative of various physiological parameters; the data indicative of various contextual parameters generated by sensor device 10; and the data input by the user. Analytical status data is characterized by the application of certain utilities or algorithms to convert one or more of the data indicative of various physiological parameters generated by sensor device 10, the data derived from the data indicative of various physiological parameters, the data indicative of various contextual parameters generated by sensor device 10, and the data input by the user into calculated health, wellness and lifestyle indicators. For example, based on data input by the user relating to the foods he or she has eaten, things such as calories and amounts of proteins, fats, carbohydrates, and certain vitamins can be calculated. As another example, skin temperature, heart rate, respiration rate, heat flow and/or GSR can be used to provide an indicator to the user of his or her stress level over a desired time period. As still another example, skin temperature, heat flow, beat-to-beat heart variability, heart rate, pulse rate, respiration rate, core temperature, galvanic skin response, EMG, EEG, EOG, blood pressure, oxygen consumption, ambient sound and body movement or motion as detected by a device such as an accelerometer can be used to provide indicators to the user of his or her sleep patterns over a desired time period.

Located on the opening Health Manager web page 150 is Health Index 155. Health Index 155 is a graphical utility used to measure and provide feedback to member users regarding their performance and the degree to which they have succeeded in reaching a healthy daily routine suggested by central monitoring unit 30. Health Index 155 thus provides an indication for the member user to track his or her progress. Health Index 155 includes six categories relating to the user's health and lifestyle: Nutrition, Activity Level, Mind Centering, Sleep, Daily Activities and How You Feel. The Nutrition category relates to what, when and how much a person eats and drinks. The Activity Level category relates to how much a person moves around. The Mind Centering category relates to the quality and quantity of time a person spends engaging in some activity that allows the body to achieve a state of profound relaxation while the mind becomes highly alert and focused. The Sleep category relates to the quality and quantity of a person's sleep. The Daily Activities category relates to the daily responsibilities and health risks people encounter. Finally, the How You Feel category relates to the general perception that a person has about how they feel on a particular day. Each category has an associated level indicator or piston that indicates, preferably on a scale ranging from poor to excellent, how the user is performing with respect to that category.

When each member user completes the initial survey described above, a profile is generated that provides the user with a summary of his or her relevant characteristics and life circumstances. A plan and/or set of goals is provided in the form of a suggested healthy daily routine. The suggested healthy daily routine may include any combination of specific suggestions for incorporating proper nutrition, exercise, mind centering, sleep, and selected activities of daily living in the user's life. Prototype schedules may be offered as guides for how these suggested activities can be incorporated into the user's life. The user may periodically retake the survey, and based on the results, the items discussed above will be adjusted accordingly.

The Nutrition category is calculated from both data input by the user and sensed by sensor device 10. The data input by the user comprises the time and duration of breakfast, lunch, dinner and any snacks, and the foods eaten, the supplements such as vitamins that are taken, and the water and other liquids consumed during a relevant, pre-selected time period. Based upon this data and on stored data relating to known properties of various foods, central monitoring unit 30 calculates well known nutritional food values such as calories and amounts of proteins, fats, carbohydrates, vitamins, etc., consumed.

The Nutrition Health Index piston level is preferably determined with respect to the following suggested healthy daily routine: eat at least three meals; eat a varied diet consisting of 6-11 servings of bread, pasta, cereal, and rice, 2-4 servings fruit, 3-5 servings of vegetables, 2-3 servings of fish, meat, poultry, dry beans, eggs, and nuts, and 2-3 servings of milk, yogurt and cheese; and drink 8 or more 8 ounce glasses of water. This routine may be adjusted based on information about the user, such as sex, age, height and/or weight. Certain nutritional targets may also be set by the user or for the user, relating to daily calories, protein, fiber, fat, carbohydrates, and/or water consumption and percentages of total consumption. Parameters utilized in the calculation of the relevant piston level include the number of meals per day, the number of glasses of water, and the types and amounts of food eaten each day as input by the user.

Figure 6:
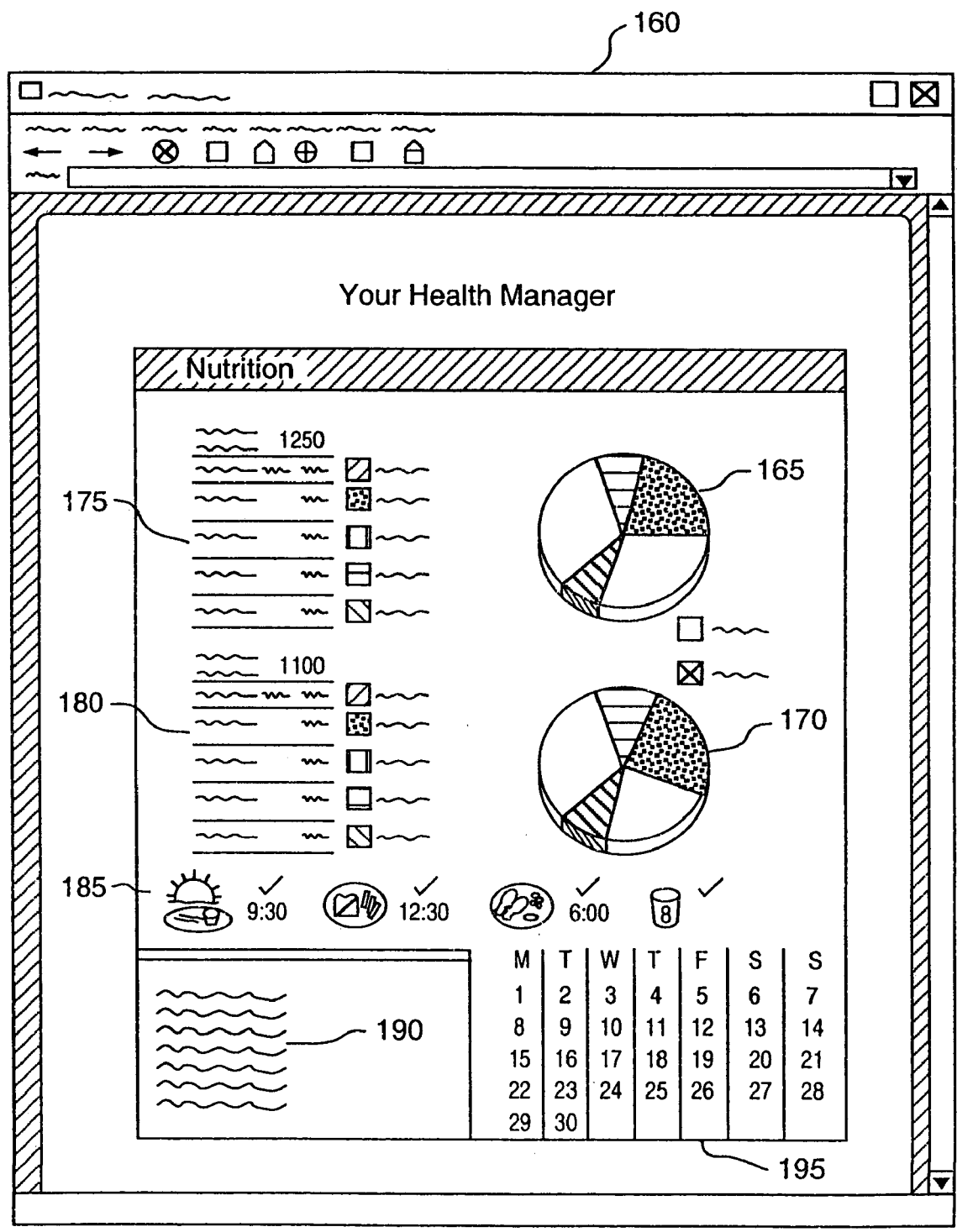
FIG. 6 is a representation of a preferred embodiment of the nutrition web page according to an aspect of the present invention.

Nutritional information is presented to the user through nutrition web page 160 as shown in FIG. 6. The preferred nutritional web page 160 includes nutritional fact charts 165 and 170 which illustrate actual and target nutritional facts, respectively as pie charts, and nutritional intake charts 175 and 180 which show total actual nutritional intake and target nutritional intake, respectively as pie charts. Nutritional fact charts 165 and 170 preferably show a percentage breakdown of items such as carbohydrates, protein and fat, and nutritional intake charts 175 and 180 are preferably broken down to show components such as total and target calories, fat, carbohydrates, protein, and vitamins. Web page 160 also includes meal and water consumption tracking 185 with time entries, hyperlinks 190 which allow the user to directly access nutrition-related news items and articles, suggestions for refining or improving daily routine with respect to nutrition and affiliate advertising elsewhere on the network, and calendar 195 for choosing between views having variable and selectable time periods. The items shown at 190 may be selected and customized based on information learned about the individual in the survey and on their performance as measured by the Health Index.

The Activity Level category of Health Index 155 is designed to help users monitor how and when they move around during the day and utilizes both data input by the user and data sensed by sensor device 10. The data input by the user may include details regarding the user's daily activities, for example the fact that the user worked at a desk from 8 a.m. to 5 p.m. and then took an aerobics class from 6 p.m. to 7 p.m. Relevant data sensed by sensor device 10 may include heart rate, movement as sensed by a device such as an accelerometer, heat flow, respiration rate, calories burned, GSR and hydration level, which may be derived by sensor device 60 or central monitoring unit 30. Calories burned may be calculated in a variety of manners, including: the multiplication of the type of exercise input by the user by the duration of exercise input by the user; sensed motion multiplied by time of motion multiplied by a filter constant; or sensed heat flux multiplied by time multiplied by a filter constant.

The Activity Level Health Index piston level is preferably determined with respect to a suggested healthy daily routine that includes: exercising aerobically for a pre-set time period, preferably 20 minutes, or engaging in a vigorous lifestyle activity for a pre-set time period, preferably one hour, and burning at least a minimum target number of calories, preferably 205 calories, through the aerobic exercise and/or lifestyle activity. The minimum target number of calories may be set according to information about the user, such as sex, age, height and/or weight. Parameters utilized in the calculation of the relevant piston level include the amount of time spent exercising aerobically or engaging in a vigorous lifestyle activity as input by the user and/or sensed by sensor device 10, and the number of calories burned above pre-calculated energy expenditure parameters.

Figure 7:
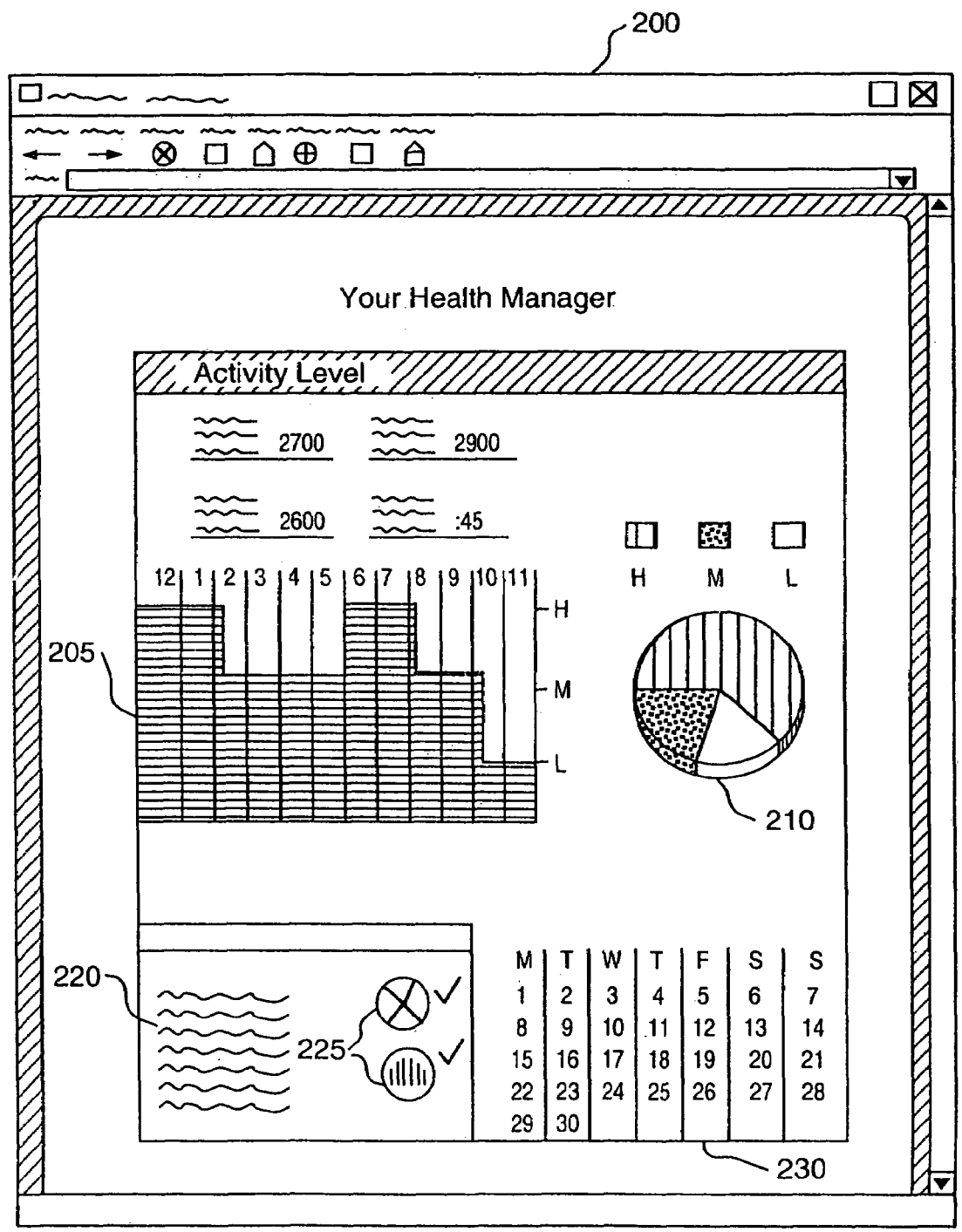
FIG. 7 is a representation of a preferred embodiment of the activity level web page according to an aspect of the present invention.

Information regarding the individual user's movement is presented to the user through activity level web page 200 shown in FIG. 7, which may include activity graph 205 in the form of a bar graph, for monitoring the individual user's activities in one of three categories: high, medium and low intensity with respect to a pre-selected unit of time. Activity percentage chart 210, in the form or a pie chart, may also be provided for showing the percentage of a pre-selected time period, such as one day, that the user spent in each category. Activity level web page 200 may also include calorie section 215 for displaying items such as total calories burned, daily target calories burned, total caloric intake, and duration of aerobic activity. Finally, activity level web page 200 may include at least one hyperlink 220 to allow a user to directly access relevant news items and articles, suggestions for refining or improving daily routine with respect to activity level and affiliate advertising elsewhere on the network. Activity level web page 200 may be viewed in a variety of formats, and may include user-selectable graphs and charts such as a bar graph, pie chart, or both, as selectable by Activity level check boxes 225. Activity level calendar 230 is provided for selecting among views having variable and selectable time periods. The items shown at 220 may be selected and customized based on information learned about the individual in the survey and on their performance as measured by the Health Index.

The Mind Centering category of Health Index 155 is designed to help users monitor the parameters relating to time spent engaging in certain activities which allow the body to achieve a state of profound relaxation while the mind becomes focused, and is based upon both data input by the user and data sensed by the sensor device 10. In particular, a user may input the beginning and end times of relaxation activities such as yoga or meditation. The quality of those activities as determined by the depth of a mind centering event can be measured by monitoring parameters including skin temperature, heart rate, respiration rate, and heat flow as sensed by sensor device 10. Percent change in GSR as derived either by sensor device 10 or central monitoring unit 30 may also be utilized.

The Mind Centering Health Index piston level is preferably calculated with respect to a suggested healthy daily routine that includes participating each day in an activity that allows the body to achieve profound relaxation while the mind stays highly focused for at least fifteen minutes. Parameters utilized in the calculation of the relevant piston level include the amount of time spent in a mind centering activity, and the percent change in skin temperature, heart rate, respiration rate, heat flow or GSR as sensed by sensor device 10 compared to a baseline which is an indication of the depth or quality of the mind centering activity.

Figure 8:
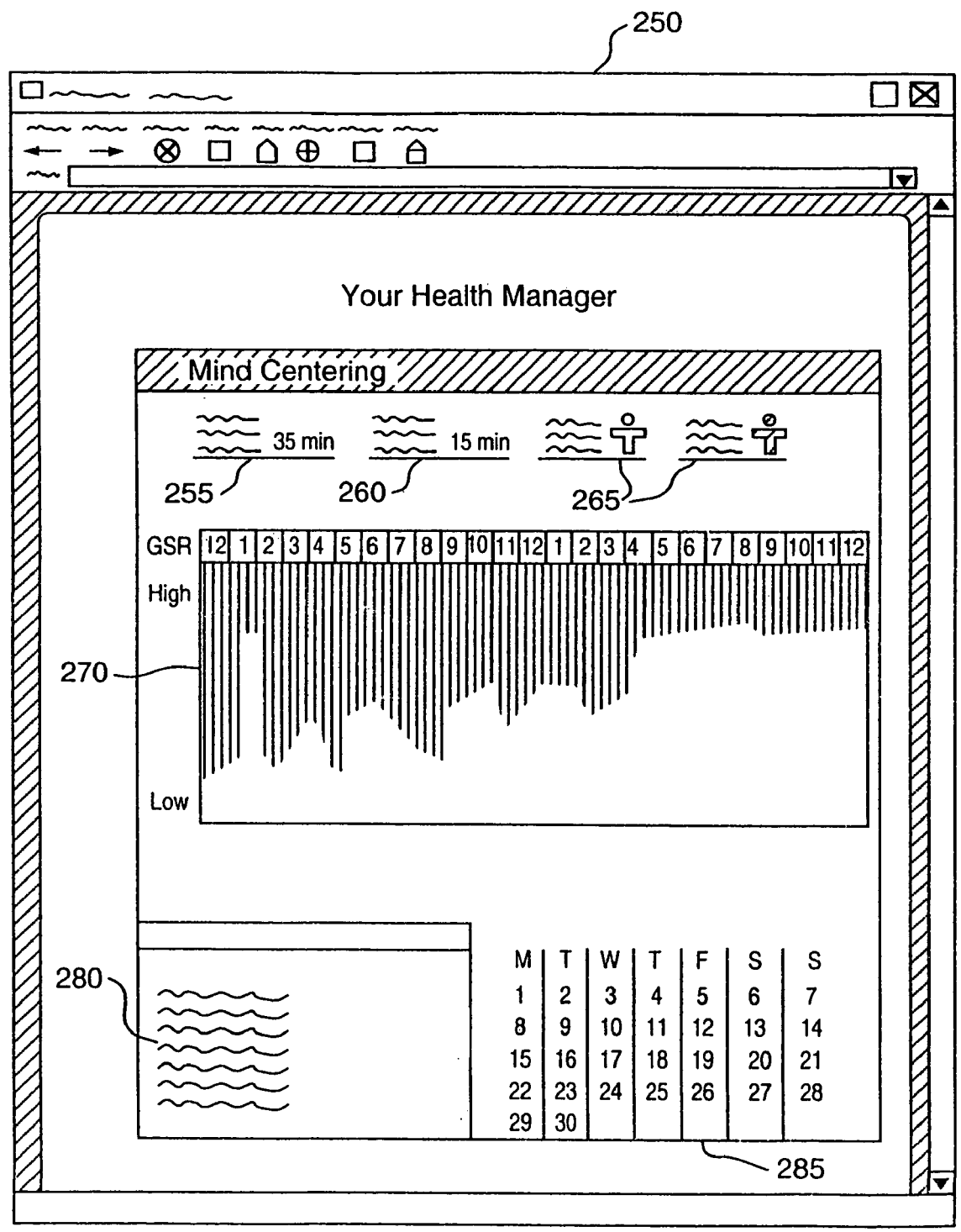
FIG. 8 is a representation of a preferred embodiment of the mind centering web page according to an aspect of the present invention.

Information regarding the time spent on self-reflection and relaxation is presented to the user through mind centering web page 250 shown in FIG. 8. For each mind centering activity, referred to as a session, the preferred mind centering web page 250 includes the time spent during the session, shown at 255, the target time, shown at 260, comparison section 265 showing target and actual depth of mind centering, or focus, and a histogram 270 that shows the overall level of stress derived from such things as skin temperature, heart rate, respiration rate, heat flow and/or GSR. In comparison section 265, the human figure outline showing target focus is solid, and the human figure outline showing actual focus ranges from fuzzy to solid depending on the level of focus. The preferred mind centering web page may also include an indication of the total time spent on mind centering activities, shown at 275, hyperlinks 280 which allow the user to directly access relevant news items and articles, suggestions for refining or improving daily routine with respect to mind centering and affiliate advertising, and a calendar 285 for choosing among views having variable and selectable time periods. The items shown at 280 may be selected and customized based on information learned about the individual in the survey and on their performance as measured by the Health Index.

The Sleep category of Health Index 155 is designed to help users monitor their sleep patterns and the quality of their sleep. It is intended to help users learn about the importance of sleep in their healthy lifestyle and the relationship of sleep to circadian rhythms, being the normal daily variations in body functions. The Sleep category is based upon both data input by the user and data sensed by sensor device 10. The data input by the user for each relevant time interval includes the times the user went to sleep and woke up and a rating of the quality of sleep. As noted in Table 2, the data from sensor device 10 that is relevant includes skin temperature, heat flow, beat-to-beat heart variability, heart rate, pulse rate, respiration rate, core temperature, galvanic skin response, EMG, EEG, EOG, blood pressure, and oxygen consumption. Also relevant is ambient sound and body movement or motion as detected by a device such as an accelerometer. This data can then be used to calculate or derive sleep onset and wake time, sleep interruptions, and the quality and depth of sleep.

The Sleep Health Index piston level is determined with respect to a healthy daily routine including getting a minimum amount, preferably eight hours, of sleep each night and having a predictable bed time and wake time. The specific parameters which determine the piston level calculation include the number of hours of sleep per night and the bed time and wake time as sensed by sensor device 10 or as input by the user, and the quality of the sleep as rated by the user or derived from other data.

Figure 9:
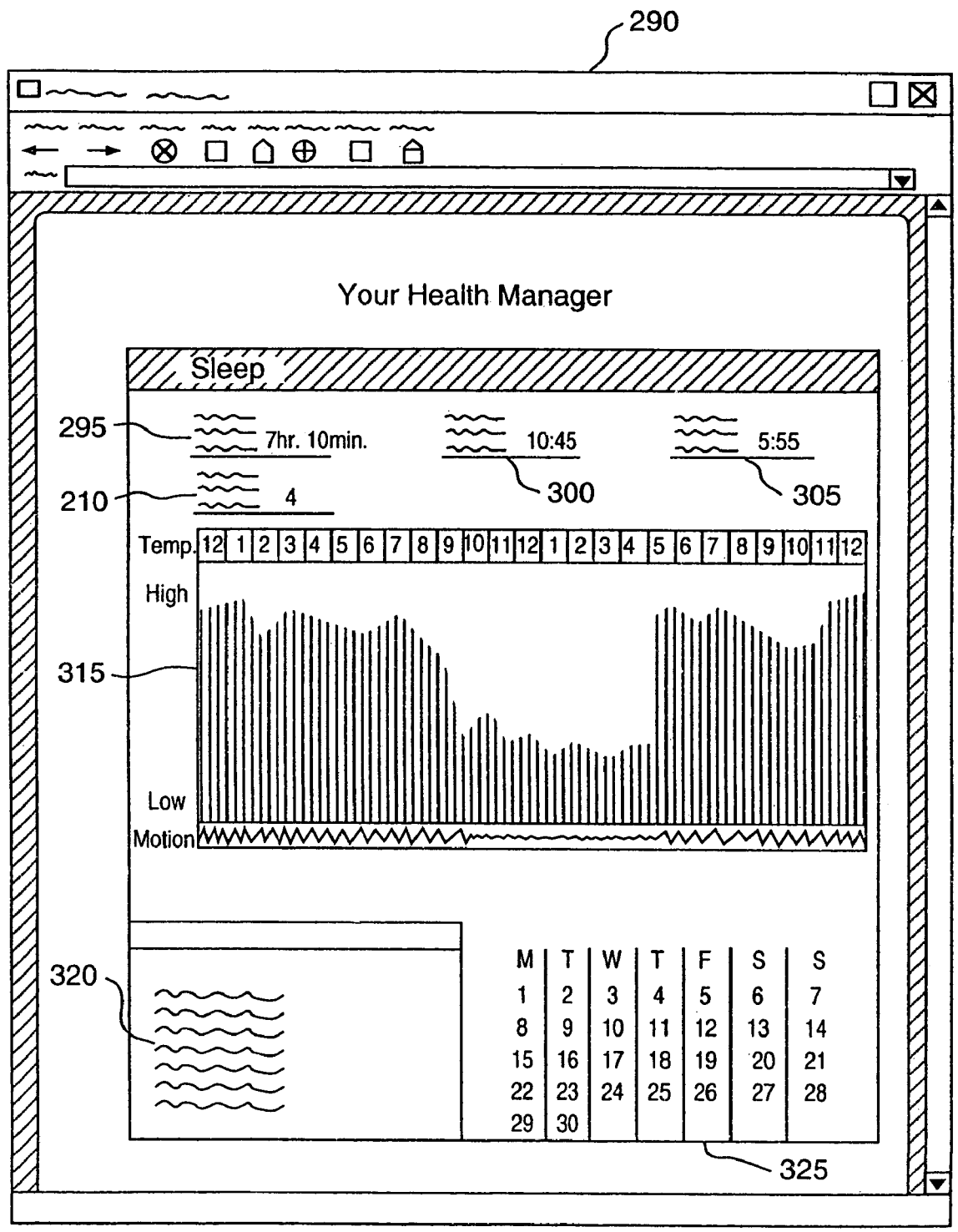
FIG. 9 is a representation of a preferred embodiment of the sleep web page according to an aspect of the present invention.

Information regarding sleep is presented to the user through sleep web page 290 shown in FIG. 9. Sleep web page 290 includes a sleep duration indicator 295, based on either data from sensor device 10 or on data input by the user, together with user sleep time indicator 300 and wake time indicator 305. A quality of sleep rating 310 input by the user may also be utilized and displayed. If more than a one day time interval is being displayed on sleep web page 290, then sleep duration indicator 295 is calculated and displayed as a cumulative value, and sleep time indicator 300, wake time indicator 305 and quality of sleep rating 310 are calculated and illustrated as averages. Sleep web page 290 also includes a user-selectable sleep graph 315 which calculates and displays one sleep related parameter over a pre-selected time interval. For illustrative purposes, FIG. 9 shows heat flow over a one-day period, which tends to be lower during sleeping hours and higher during waking hours. From this information, a person's bio-rhythms can be derived. Sleep graph 315 may also include a graphical representation of data from an accelerometer incorporated in sensor device 10 which monitors the movement of the body. The sleep web page 290 may also include hyperlinks 320 which allow the user to directly access sleep related news items and articles, suggestions for refining or improving daily routine with respect to sleep and affiliate advertising available elsewhere on the network, and a sleep calendar 325 for choosing a relevant time interval. The items shown at 320 may be selected and customized based on information learned about the individual in the survey and on their performance as measured by the Health Index.

The Activities of Daily Living category of Health Index 155 is designed to help users monitor certain health and safety related activities and risks and is based entirely on data input by the user. The Activities of Daily Living category is divided into four sub-categories: personal hygiene, which allows the user to monitor activities such as brushing and flossing his or her teeth and showering; health maintenance, that tracks whether the user is taking prescribed medication or supplements and allows the user to monitor tobacco and alcohol consumption and automobile safety such as seat belt use; personal time, that allows the user to monitor time spent socially with family and friends, leisure, and mind centering activities; and responsibilities, that allows the user to monitor certain work and financial activities such as paying bills and household chores.

The Activities of Daily Living Health Index piston level is preferably determined with respect to the healthy daily routine described below. With respect to personal hygiene, the routine requires that the users shower or bathe each day, brush and floss teeth each day, and maintain regular bowel habits. With respect to health maintenance, the routine requires that the user take medications and vitamins and/or supplements, use a seat belt, refrain from smoking, drink moderately, and monitor health each day with the Health Manager. With respect to personal time, the routine requires the users to spend at least one hour of quality time each day with family and/or friends, restrict work time to a maximum of nine hours a day, spend some time on a leisure or play activity each day, and engage in a mind stimulating activity. With respect to responsibilities, the routine requires the users to do household chores, pay bills, be on time for work, and keep appointments. The piston level is calculated based on the degree to which the user completes a list of daily activities as determined by information input by the user.

Figure 10:
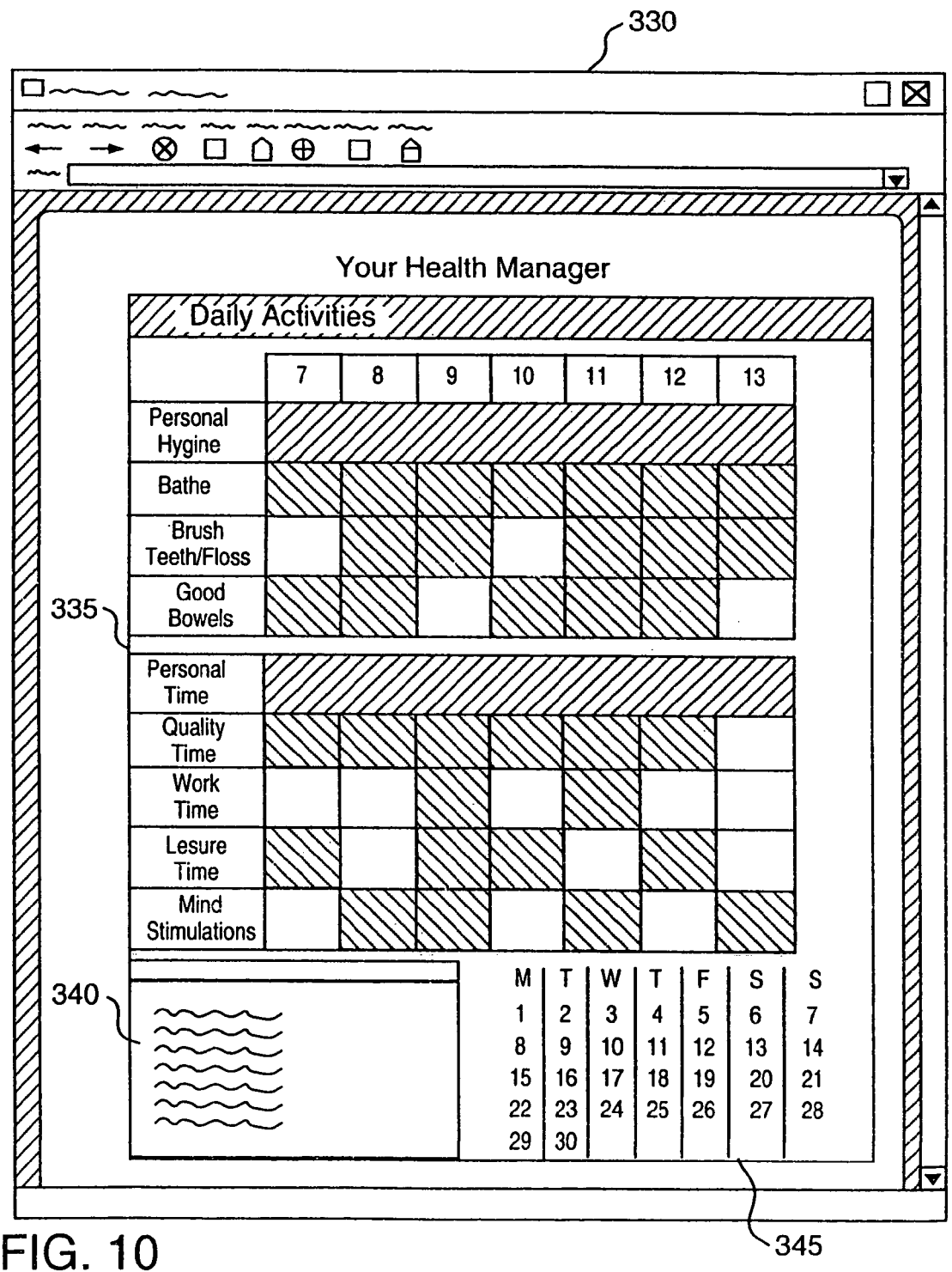
FIG. 10 is a representation of a preferred embodiment of the daily activities web page according to an aspect of the present invention.

Information relating to these activities is presented to the user through daily activities web page 330 shown in FIG. 10. In preferred daily activities web page 330, activities chart 335, selectable for one or more of the sub-categories, shows whether the user has done what is required by the daily routine. A colored or shaded box indicates that the user has done the required activity, and an empty, non-colored or shaded box indicates that the user has not done the activity. Activities chart 335 can be created and viewed in selectable time intervals. For illustrative purposes, FIG. 10 shows the personal hygiene and personal time sub-categories for a particular week. In addition, daily activities web page 330 may include daily activity hyperlinks 340 which allow the user to directly access relevant news items and articles, suggestions for improving or refining daily routine with respect to activities of daily living and affiliate advertising, and a daily activities calendar 345 for selecting a relevant time interval. The items shown at 340 may be selected and customized based on information learned about the individual in the survey and on their performance as measured by the Health Index.

The How You Feel category of Health Index 155 is designed to allow users to monitor their perception of how they felt on a particular day, and is based on information, essentially a subjective rating, that is input directly by the user. A user provides a rating, preferably on a scale of 1 to 5, with respect to the following nine subject areas: mental sharpness; emotional and psychological well being; energy level; ability to cope with life stresses; appearance; physical well being; self-control; motivation; and comfort in relating to others. Those ratings are averaged and used to calculate the relevant piston level.

Figure 11:
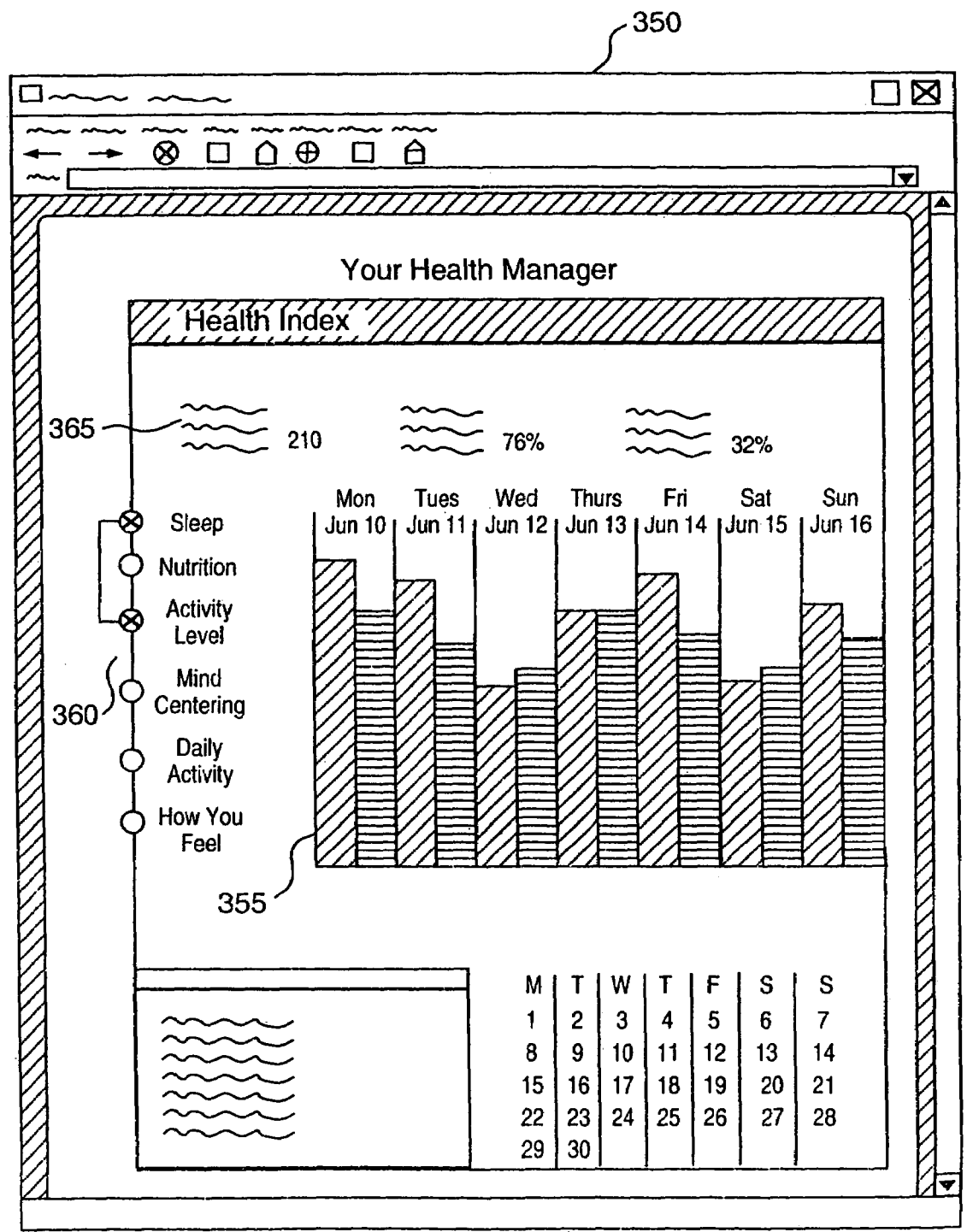
FIG. 11 is a representation of a preferred embodiment of the Health Index web page according to an aspect of the present invention.
Figure 12:
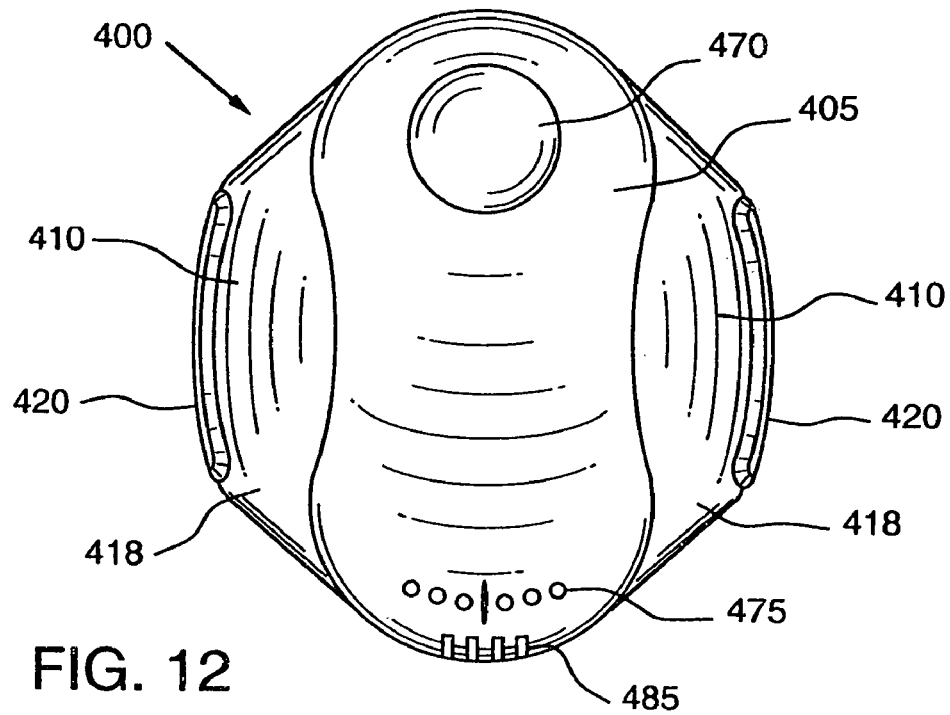
FIG. 12 is a front view of a specific embodiment of the sensor device shown in FIG. 1.

Referring to FIG. 11, Health Index web page 350 is shown. Health Index web page 350 enables users to view the performance of their Health Index over a user selectable time interval including any number of consecutive or non-consecutive days. Using Health Index selector buttons 360, the user can select to view the Health Index piston levels for one category, or can view a side-by-side comparison of the Health Index piston levels for two or more categories. For example, a user might want to just turn on Sleep to see if their overall sleep rating improved over the previous month, much in the same way they view the performance of their favorite stock. Alternatively, Sleep and Activity Level might be simultaneously displayed in order to compare and evaluate Sleep ratings with corresponding Activity Level ratings to determine if any day-to-day correlations exist. Nutrition ratings might be displayed with How You Feel for a pre-selected time interval to determine if any correlation exists between daily eating habits and how they felt during that interval. For illustrative purposes, FIG. 11 illustrates a comparison of Sleep and Activity Level piston levels for the week of June 10 through June 16. Health Index web page 350 also includes tracking calculator 365 that displays access information and statistics such as the total number of days the user has logged in and used the Health Manager, the percentage of days the user has used the Health Manager since becoming a subscriber, and percentage of time the user has used the sensor device 10 to gather data.

Referring again to FIG. 5, opening Health Manager web page 150 may include a plurality of user selectable category summaries 156a through 156f, one corresponding to each of the Health Index 155 categories. Each category summary 156a through 156f presents a pre-selected filtered subset of the data associated with the corresponding category. Nutrition category summary 156a displays daily target and actual caloric intake. Activity Level category summary 156b displays daily target and actual calories burned. Mind Centering category summary 156c displays target and actual depth of mind centering or focus. Sleep category summary 156d displays target sleep, actual sleep, and a sleep quality rating. Daily Activities category summary 156e displays a target and actual score based on the percentage of suggested daily activities that are completed. The How You Feel category summary 156f shows a target and actual rating for the day.

Opening Health Manager web page 150 also may include Daily Dose section 157 which provides, on a daily time interval basis, information to the user, including, but not limited to, hyperlinks to news items and articles, commentary and reminders to the user based on tendencies, such as poor nutritional habits, determined from the initial survey. The commentary for Daily Dose 157 may, for example, be a factual statement that drinking 8 glasses of water a day can reduce the risk of colon cancer by as much as 32%, accompanied by a suggestion to keep a cup of water by your computer or on your desk at work and refill often. Opening Health Manager web page 150 also may include a Problem Solver section 158 that actively evaluates the user's performance in each of the categories of Health Index 155 and presents suggestions for improvement. For example, if the system detects that a user's Sleep levels have been low, which suggest that the user has been having trouble sleeping, Problem Solver 158 can provide suggestions for way to improve sleep. Problem Solver 158 also may include the capability of user questions regarding improvements in performance. Opening Health Manager web page 150 may also include a Daily Data section 159 that launches an input dialog box. The input dialog box facilitates input by the user of the various data required by the Health Manager. As is known in the art, data entry may be in the form of selection from pre-defined lists or general free form text input. Finally, opening Health Manager web page 150 may include Body Stats section 161 which may provide information regarding the user's height, weight, body measurements, body mass index or BMI, and vital signs such as heart rate, blood pressure or any of the identified physiological parameters.

Figure 17:
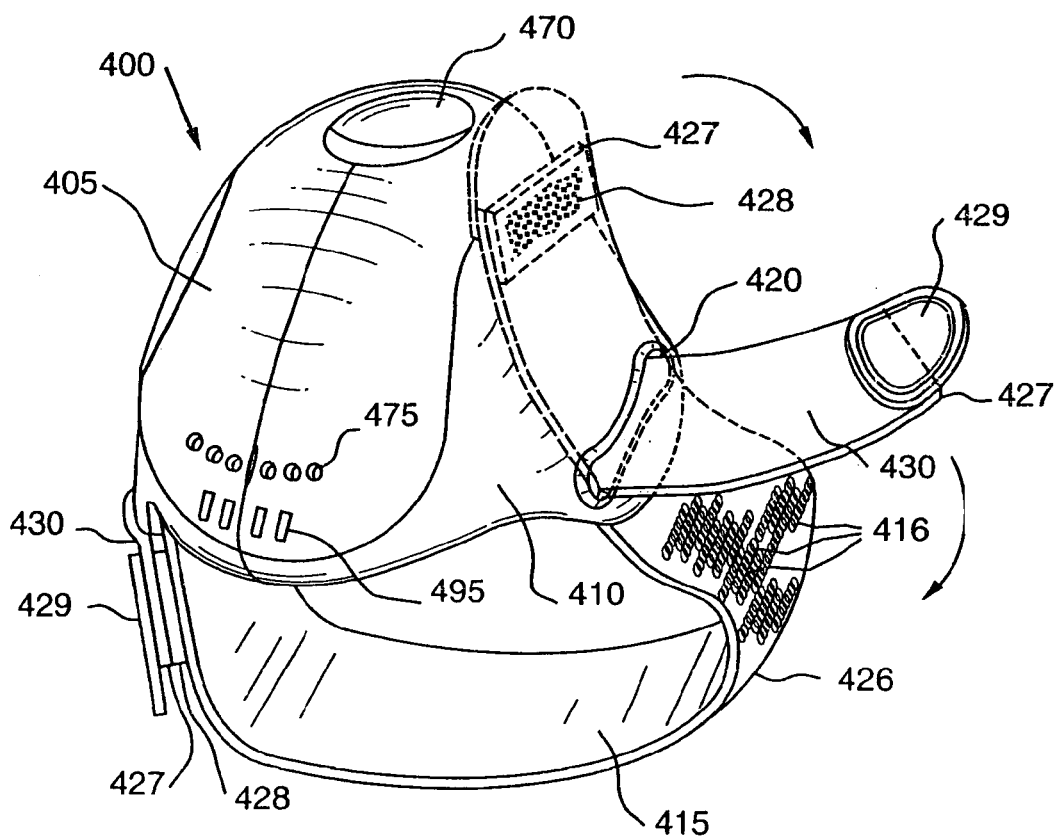

Referring to FIGS. 12-17, a specific embodiment of sensor device 10 is shown which is in the form of an armband adapted to be worn by an individual on his or her upper arm, between the shoulder and the elbow. The specific embodiment of sensor device 10 shown in FIGS. 12-17 will, for convenience, be referred to as armband sensor device 400. Armband sensor device 400 includes computer housing 405, flexible wing body 410, and, as shown in FIG. 17, elastic strap 415. Computer housing 405 and flexible wing body 410 are preferably made of a flexible urethane material or an elastomeric material such as rubber or a rubber-silicone blend by a molding process. Flexible wing body 410 includes first and second wings 418 each having a thru-hole 420 located near the ends 425 thereof. First and second wings 418 are adapted to wrap around a portion of the wearer's upper arm.

Elastic strap 415 is used to removably affix armband sensor device 400 to the individual's upper arm. As seen in FIG. 17, bottom surface 426 of elastic strap 415 is provided with Velcro loops 416 along a portion thereof. Each end 427 of elastic strap 415 is provided with Velcro hook patch 428 on bottom surface 426 and pull tab 429 on top surface 430. A portion of each pull tab 429 extends beyond the edge of each end 427.

In order to wear armband sensor device 400, a user inserts each end 427 of elastic strap 415 into a respective thru-hole 420 of flexible wing body 410. The user then places his arm through the loop created by elastic strap 415, flexible wing body 410 and computer housing 405. By pulling each pull tab 429 and engaging Velcro hook patches 428 with Velcro loops 416 at a desired position along bottom surface 426 of elastic strap 415, the user can adjust elastic strap 415 to fit comfortably. Since Velcro hook patches 428 can be engaged with Velcro loops 416 at almost any position along bottom surface 426, armband sensor device 400 can be adjusted to fit arms of various sizes. Also, elastic strap 415 may be provided in various lengths to accommodate a wider range of arm sizes. As will be apparent to one of skill in the art, other means of fastening and adjusting the size of elastic strap may be used, including, but not limited to, snaps, buttons, or buckles. It is also possible to use two elastic straps that fasten by one of several conventional means including Velcro, snaps, buttons, buckles or the like, or merely a single elastic strap affixed to wings 418.

Alternatively, instead of providing thru-holes 420 in wings 418, loops having the shape of the letter D, not shown, may be attached to ends 425 of wings 418 by one of several conventional means. For example, a pin, not shown, may be inserted through ends 425, wherein the pin engages each end of each loop. In this configuration, the D-shaped loops would serve as connecting points for elastic strap 415, effectively creating a thru-hole between each end 425 of each wing 418 and each loop.

Figure 18:
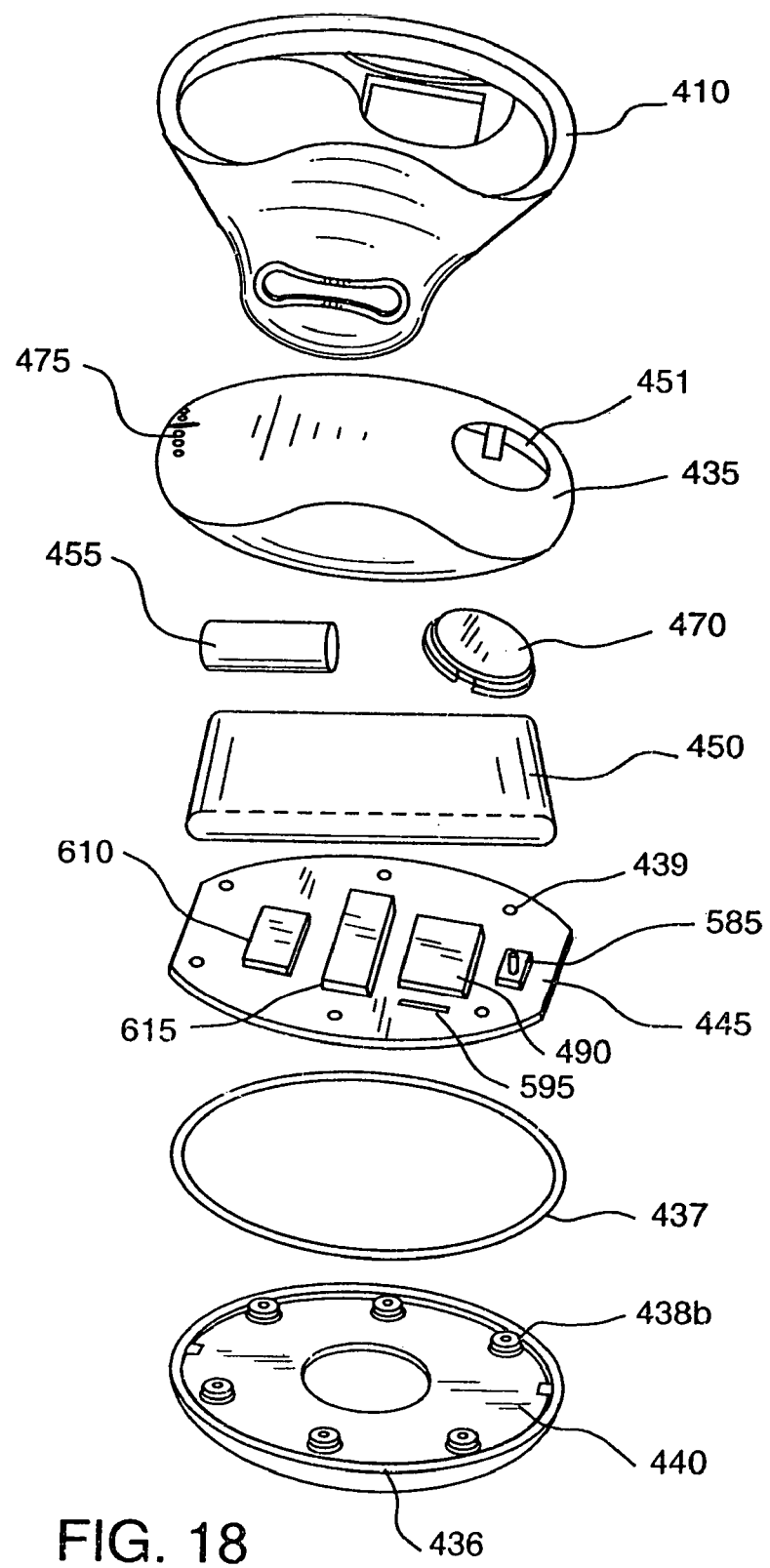
FIG. 18 is an exploded side perspective view of a specific embodiment of the sensor device shown in FIG. 1.

As shown in FIG. 18, which is an exploded view of armband sensor device 400, computer housing 405 includes a top portion 435 and a bottom portion 440. Contained within computer housing 405 are printed circuit board or PCB 445, rechargeable battery 450, preferably a lithium ion battery, and vibrating motor 455 for providing tactile feedback to the wearer, such as those used in pagers, suitable examples of which are the Model 12342 and 12343 motors sold by MG Motors Ltd. of the United Kingdom.

Top portion 435 and bottom portion 440 of computer housing 405 sealingly mate along groove 436 into which O-ring 437 is fit, and may be affixed to one another by screws, not shown, which pass through screw holes 438a and stiffeners 438b of bottom portion 440 and apertures 439 in PCB 445 and into threaded receiving stiffeners 451 of top portion 435. Alternately, top portion 435 and bottom portion 440 may be snap fit together or affixed to one another with an adhesive. Preferably, the assembled computer housing 405 is sufficiently water resistant to permit armband sensor device 400 to be worn while swimming without adversely affecting the performance thereof.

Figure 13:
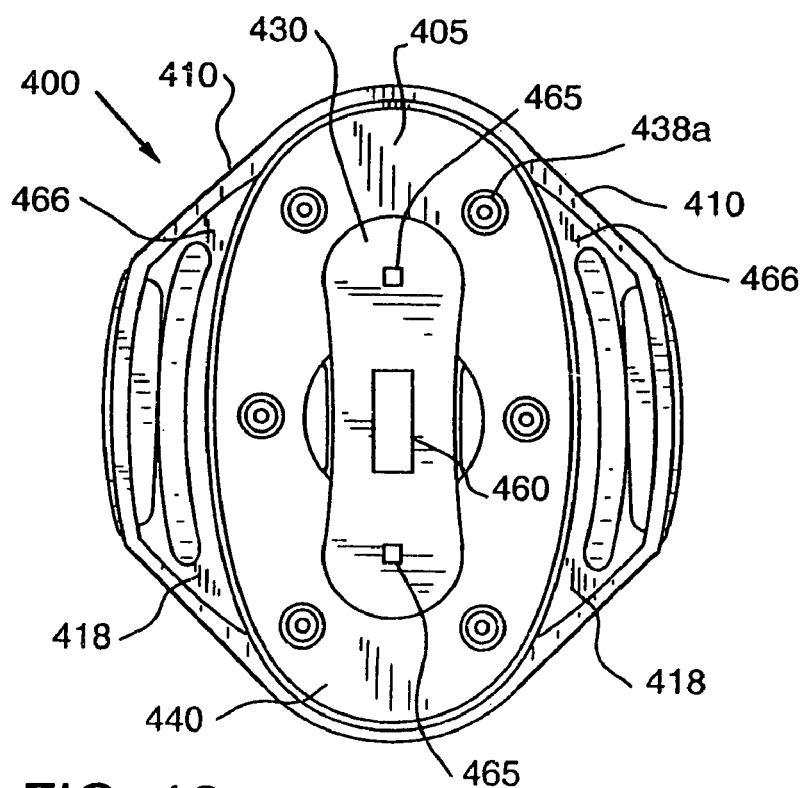
FIG. 13 is a back view of a specific embodiment of the sensor device shown in FIG. 1.
Figure 14:
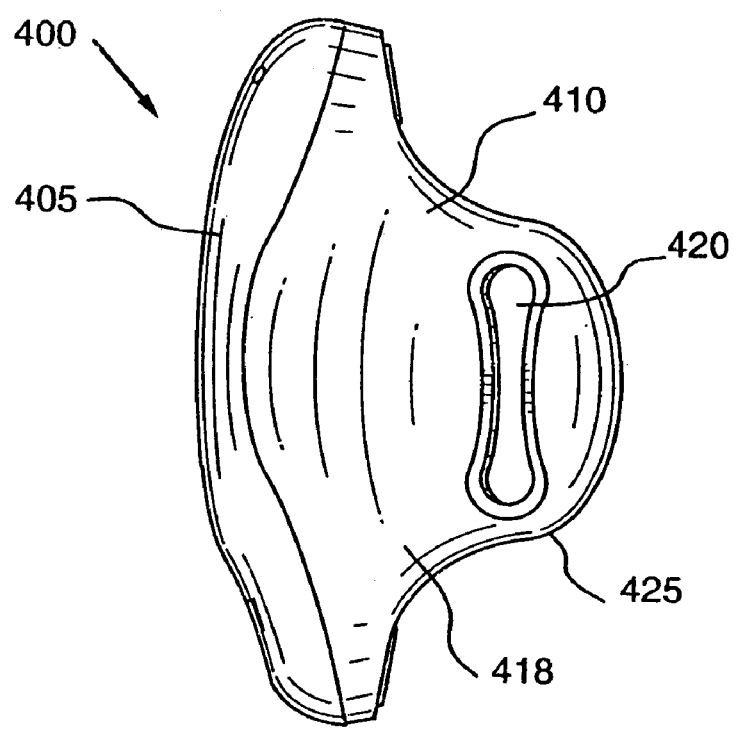
FIG. 14 is a side view of a specific embodiment of the sensor device shown in FIG. 1.
Figure 15:
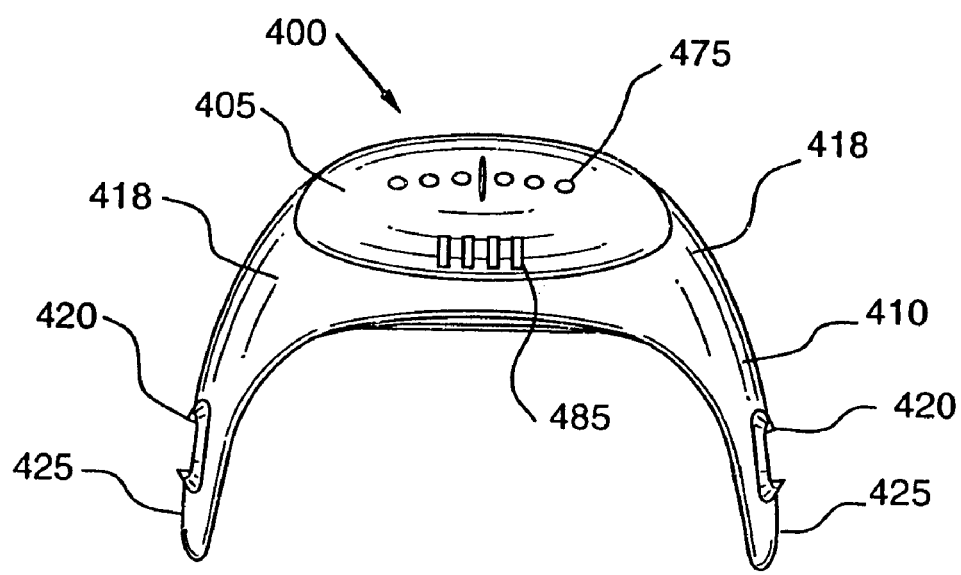
FIG. 15 is a bottom view of a specific embodiment of the sensor device shown in FIG. 1.
Figure 16:
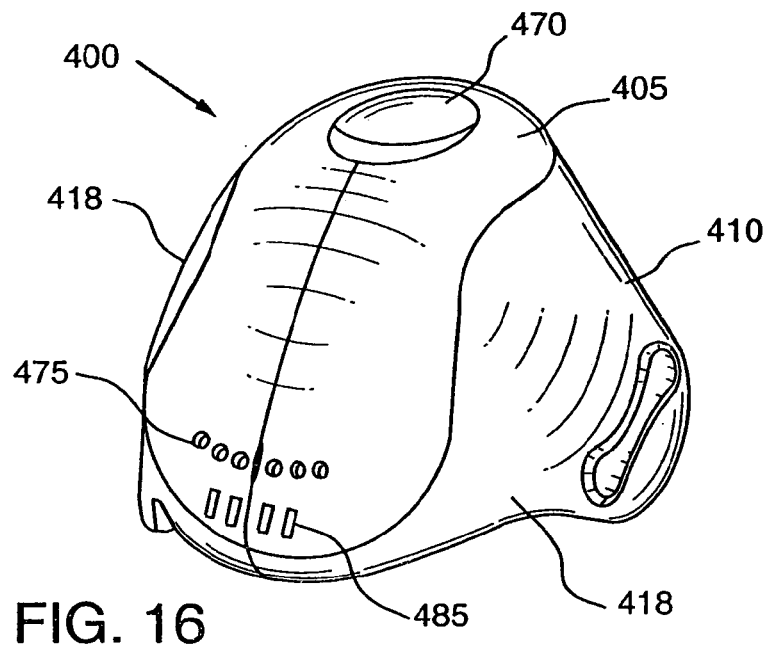
FIGS. 16 and 17 are front perspective views of a specific embodiment of the sensor device shown in FIG. 1.

As can be seen in FIG. 13, bottom portion 440 includes, on a bottom side thereof, a raised platform 430. Affixed to raised platform 430 is heat flow or flux sensor 460, a suitable example of which is the micro-foil heat flux sensor sold by RdF Corporation of Hudson, N.H. Heat flux sensor 460 functions as a self-generating thermopile transducer, and preferably includes a carrier made of a polyamide film. Bottom portion 440 may include on a top side thereof, that is on a side opposite the side to which heat flux sensor 460 is affixed, a heat sink, not shown, made of a suitable metallic material such as aluminum. Also affixed to raised platform 430 are GSR sensors 465, preferably comprising electrodes formed of a material such as conductive carbonized rubber, gold or stainless steel. Although two GSR sensors 465 are shown in FIG. 13, it will be appreciated by one of skill in the art that the number of GSR sensors 465 and the placement thereof on raised platform 430 can vary as long as the individual GSR sensors 465, i.e., the electrodes, are electrically isolated from one another. By being affixed to raised platform 430, heat flux sensor 460 and GSR sensors 465 are adapted to be in contact with the wearer's skin when armband sensor device 400 is worn. Bottom portion 440 of computer housing 405 may also be provided with a removable and replaceable soft foam fabric pad, not shown, on a portion of the surface thereof that does not include raised platform 430 and screw holes 438a. The soft foam fabric is intended to contact the wearer's skin and make armband sensor device 400 more comfortable to wear.

Electrical coupling between heat flux sensor 460, GSR sensors 465, and PCB 445 may be accomplished in one of various known methods. For example, suitable wiring, not shown, may be molded into bottom portion 440 of computer housing 405 and then electrically connected, such as by soldering, to appropriate input locations on PCB 445 and to heat flux sensor 460 and GSR sensors 465. Alternatively, rather than molding wiring into bottom portion 440, thru-holes may be provided in bottom portion 440 through which appropriate wiring may pass. The thru-holes would preferably be provided with a water tight seal to maintain the integrity of computer housing 405.

Rather than being affixed to raised platform 430 as shown in FIG. 13, one or both of heat flux sensor 460 and GSR sensors 465 may be affixed to the inner portion 466 of flexible wing body 410 on either or both of wings 418 so as to be in contact with the wearer's skin when armband sensor device 400 is worn. In such a configuration, electrical coupling between heat flux sensor 460 and GSR sensors 465, whichever the case may be, and the PCB 445 may be accomplished through suitable wiring, not shown, molded into flexible wing body 410 that passes through one or more thru-holes in computer housing 405 and that is electrically connected, such as by soldering, to appropriate input locations on PCB 445. Again, the thru-holes would preferably be provided with a water tight seal to maintain the integrity of computer housing 405. Alternatively, rather than providing thru-holes in computer housing 405 through which the wiring passes, the wiring may be captured in computer housing 405 during an overmolding process, described below, and ultimately soldered to appropriate input locations on PCB 445.

As shown in FIGS. 12, 16, 17 and 18, computer housing 405 includes a button 470 that is coupled to and adapted to activate a momentary switch 585 on PCB 445. Button 470 maybe used to activate armband sensor device 400 for use, to mark the time an event occurred or to request system status information such as battery level and memory capacity. When button 470 is depressed, momentary switch 585 closes a circuit and a signal is sent to processing unit 490 on PCB 445. Depending on the time interval for which button 470 is depressed, the generated signal triggers one of the events just described. Computer housing 405 also includes LEDs 475, which may be used to indicate battery level or memory capacity or to provide visual feedback to the wearer. Rather than LEDs 475, computer housing 405 may also include a liquid crystal display or LCD to provide battery level, memory capacity or visual feedback information to the wearer. Battery level, memory capacity or feedback information may also be given to the user tactily or audibly.

Armband sensor device 400 may be adapted to be activated for use, that is collecting data, when either of GSR sensors 465 or heat flux sensor 460 senses a particular condition that indicates that armband sensor device 400 has been placed in contact with the user's skin. Also, armband sensor device 400 may be adapted to be activated for use when one or more of heat flux sensor 460, GSR sensors 465, accelerometer 495 or 550, or any other device in communication with armband sensor device 400, alone or in combination, sense a particular condition or conditions that indicate that the armband sensor device 400 has been placed in contact with the user's skin for use. At other times, armband sensor device 400 would be deactivated, thus preserving battery power.

Figure 19:
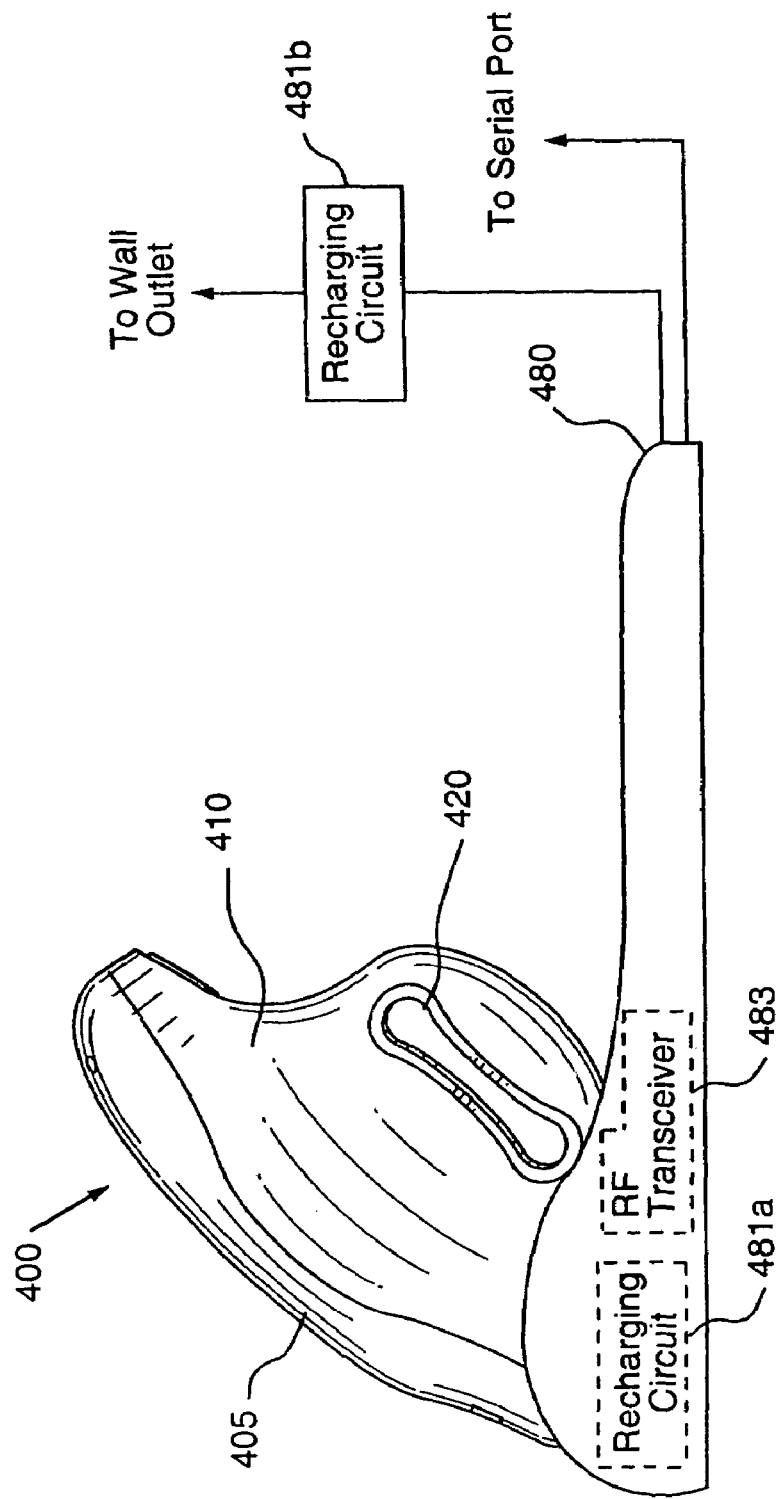
FIG. 19 is a side view of the sensor device shown in FIGS. 12 through 18 inserted into a battery recharger unit.

Computer housing 405 is adapted to be coupled to a battery recharger unit 480 shown in FIG. 19 for the purpose of recharging rechargeable battery 450. Computer housing 405 includes recharger contacts 485, shown in FIGS. 12, 15, 16 and 17, that are coupled to rechargeable battery 450. Recharger contacts 485 may be made of a material such as brass, gold or stainless steel, and are adapted to mate with and be electrically coupled to electrical contacts, not shown, provided in battery recharger unit 480 when armband sensor device 400 is placed therein. The electrical contacts provided in battery recharger unit 480 may be coupled to recharging circuit 481a provided inside battery recharger unit 480. In this configuration, recharging circuit 481 would be coupled to a wall outlet, such as by way of wiring including a suitable plug that is attached or is attachable to battery recharger unit 480. Alternatively, electrical contacts 480 may be coupled to wiring that is attached to or is attachable to battery recharger unit 480 that in turn is coupled to recharging circuit 481b external to battery recharger unit 480. The wiring in this configuration would also include a plug, not shown, adapted to be plugged into a conventional wall outlet.

Figure 20:
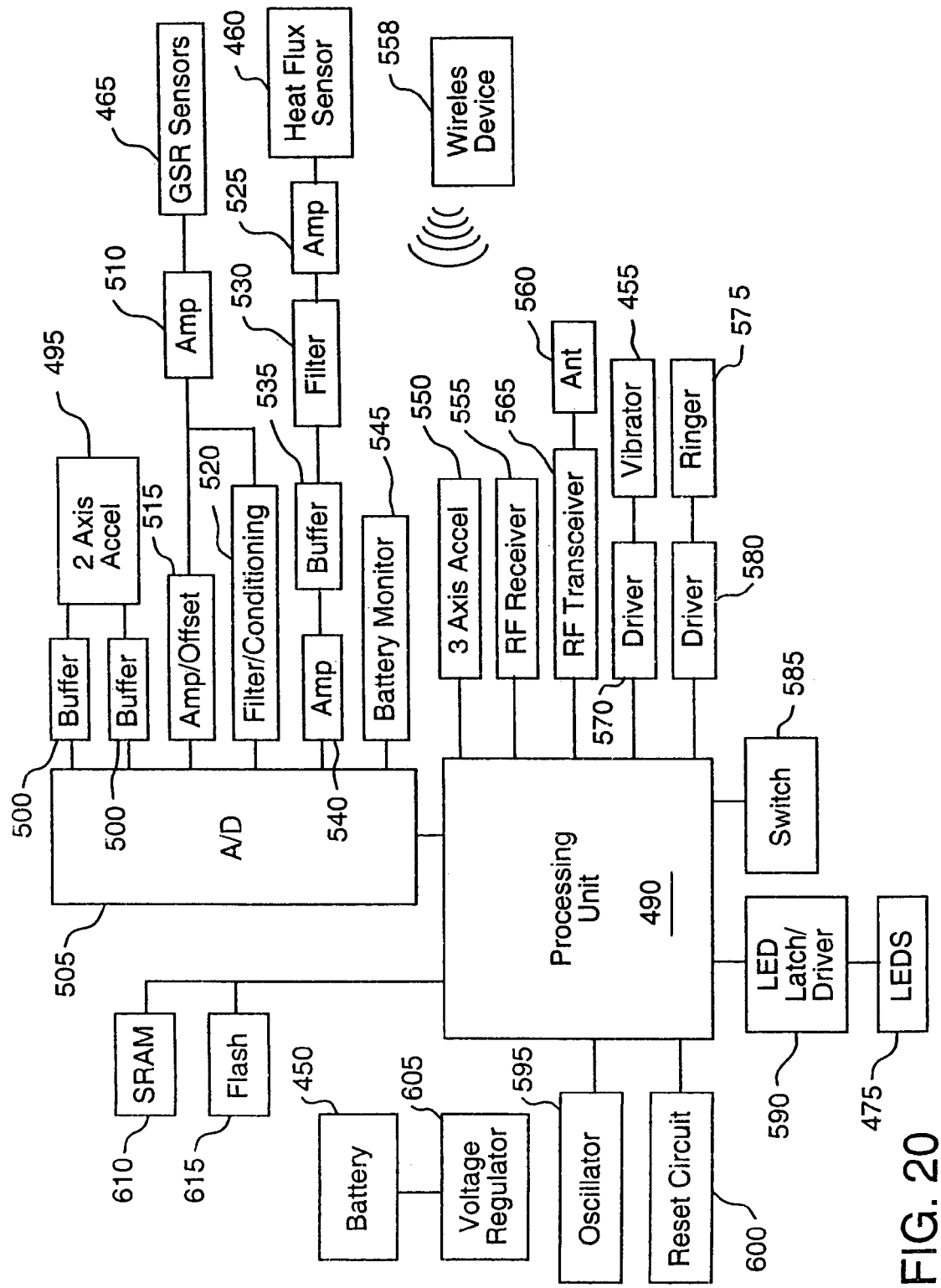
FIG. 20 is a block diagram illustrating all of the components either mounted on or coupled to the printed circuit board forming a part of the sensor device shown in FIGS. 12 through 18.

Also provided inside battery recharger unit 480 is RF transceiver 483 adapted to receive signals from and transmit signals to RF transceiver 565 provided in computer housing 405 and shown in FIG. 20. RF transceiver 483 is adapted to be coupled, for example by a suitable cable, to a serial port, such as an RS 232 port or a USB port, of a device such as personal computer 35 shown in FIG. 1. Thus, data may be uploaded from and downloaded to armband sensor device 400 using RF transceiver 483 and RF transceiver 565. It will be appreciated that although RF transceivers 483 and 565 are shown in FIGS. 19 and 20, other forms of wireless transceivers may be used, such as infrared transceivers. Alternatively, computer housing 405 may be provided with additional electrical contacts, not shown, that would be adapted to mate with and be electrically coupled to additional electrical contacts, not shown, provided in battery recharger unit 480 when armband sensor device 400 is placed therein. The additional electrical contacts in the computer housing 405 would be coupled to the processing unit 490 and the additional electrical contacts provided in battery recharger unit 480 would be coupled to a suitable cable that in turn would be coupled to a serial port, such as an RS R32 port or a USB port, of a device such as personal computer 35. This configuration thus provides an alternate method for uploading of data from and downloading of data to armband sensor device 400 using a physical connection.

FIG. 20 is a schematic diagram that shows the system architecture of armband sensor device 400, and in particular each of the components that is either on or coupled to PCB 445.

As shown in FIG. 17, PCB 445 includes processing unit 490, which maybe a microprocessor, a microcontroller, or any other processing device that can be adapted to perform the functionality described herein. Processing unit 490 is adapted to provide all of the functionality described in connection with microprocessor 20 shown in FIG. 2. A suitable example of processing unit 490 is the Dragonball EZ sold by Motorola, Inc. of Schaumburg, Ill. PCB 445 also has thereon a two-axis accelerometer 495, a suitable example of which is the Model ADXL210 accelerometer sold by Analog Devices, Inc. of Norwood, Mass. Two-axis accelerometer 495 is preferably mounted on PCB 445 at an angle such that its sensing axes are offset at an angle substantially equal to 45 degrees from the longitudinal axis of PCB 445 and thus the longitudinal axis of the wearer's arm when armband sensor device 400 is worn. The longitudinal axis of the wearer's arm refers to the axis defined by a straight line drawn from the wearer's shoulder to the wearer's elbow. The output signals of two-axis accelerometer 495 are passed through buffers 500 and input into analog to digital converter 505 that in turn is coupled to processing unit 490. GSR sensors 465 are coupled to amplifier 510 on PCB 445. Amplifier 510 provides amplification and low pass filtering functionality, a suitable example of which is the Model AD8544 amplifier sold by Analog Devices, Inc. of Norwood, Mass. The amplified and filtered signal output by amplifier 510 is input into amp/offset 515 to provide further gain and to remove any bias voltage and into filter/conditioning circuit 520, which in turn are each coupled to analog to digital converter 505. Heat flux sensor 460 is coupled to differential input amplifier 525, such as the Model INA amplifier sold by Burr-Brown Corporation of Tucson, Ariz., and the resulting amplified signal is passed through filter circuit 530, buffer 535 and amplifier 540 before being input to analog to digital converter 505. Amplifier 540 is configured to provide further gain and low pass filtering, a suitable example of which is the Model AD8544 amplifier sold by Analog Devices, Inc. of Norwood, Mass. PCB 445 also includes thereon a battery monitor 545 that monitors the remaining power level of rechargeable battery 450. Battery monitor 545 preferably comprises a voltage divider with a low pass filter to provide average battery voltage. When a user depresses button 470 in the manner adapted for requesting battery level, processing unit 490 checks the output of battery monitor 545 and provides an indication thereof to the user, preferably through LEDs 475, but also possibly through vibrating motor 455 or ringer 575. An LCD may also be used.

PCB 445 may include three-axis accelerometer 550 instead of or in addition to two-axis accelerometer 495. The three-axis accelerometer outputs a signal to processing unit 490. A suitable example of three-axis accelerometer is the IPAM product sold by I.M. Systems, Inc. of Scottsdale, Ariz. Three-axis accelerometer 550 is preferably tilted in the manner described with respect to two-axis accelerometer 495.

PCB 445 also includes RF receiver 555 that is coupled to processing unit 490. RF receiver 555 may be used to receive signals that are output by another device capable of wireless transmission, shown in FIG. 20 as wireless device 558, worn by or located near the individual wearing armband sensor device 400. Located near as used herein means within the transmission range of wireless device 558. For example, wireless device 558 may be a chest mounted heart rate monitor such as the Tempo product sold by Polar Electro of Oulu, Finland. Using such a heart rate monitor, data indicative of the wearer's heart rate can be collected by armband sensor device 400. Antenna 560 and RF transceiver 565 are coupled to processing unit 490 and are provided for purposes of uploading data to central monitoring unit 30 and receiving data downloaded from central monitoring unit 30. RF transceiver 565 and RF receiver 555 may, for example, employ Bluetooth technology as the wireless transmission protocol. Also, other forms of wireless transmission may be used, such as infrared transmission.

The fact that RF Transceiver 565 may be used for wirelessly uploading data from and wirelessly downloading data to armband sensor device 400 is advantageous because it eliminates the need to remove armband sensor device 400 to perform these functions, as would be required with a physical connection. For example, if armband sensor device 400 was being worn under the user's clothing, requiring removal of armband sensor device 400 prior to uploading and/or downloading data increases user inconvenience. In addition, the wearing of armband sensor device 400 has an effect on the user's skin and underlying blood vessels, which in turn may effect any measurements being made with respect thereto. It may be necessary for a period of time during which armband sensor device 400 is worn by the user to elapse before a steady state is achieved and consistent, accurate measurements can be made. By providing armband sensor device 400 with wireless communications capability, data can be uploaded and downloaded without disturbing an established steady state equilibrium condition. For example, programming data for processing unit 490 that controls the sampling characteristics of armband sensor device 400 can be downloaded to armband sensor device 400 without disturbing the steady state equilibrium condition.

In addition, antenna 560 and RF transceiver 565 permit armband sensor device 400 to communicate wirelessly with other devices capable of wireless communication, i.e., transmit information to and receive information from those devices. The devices may include, for example, devices that are implanted in the body of the person using armband sensor device 400, such as an implantable heart pacemaker or an implantable insulin dispensing device, for example the MiniMed® 2007 implantable insulin pump sold by MiniMed Inc. of Northridge, Calif., devices worn on the body of the person using armband sensor device 400, or devices located near the person using armband sensor device 400 at any particular time, such as an electronic scale, a blood pressure monitor, a glucose monitor, a cholesterol monitor or another armband sensor device 400. With this two-way wireless communication capability, armband sensor device 400 may be adapted to transmit information that activates or deactivates such a device for use or information that programs such a device to behave in a particular way. For example, armband sensor device 400 may be adapted to activate a piece of exercise equipment such as a treadmill and program it to operate with certain parameters that are dictated or desired by or optimal for the user of armband sensor device 400. As another example, armband sensor device 400 may be adapted to adjust a computer controlled thermostat in a home based on the detected skin temperature of the wearer or turn off a computer controlled lighting system, television or stereo when the wearer is determined to have fallen asleep.

Vibrating motor 455 is coupled to processing unit 490 through vibrator driver 570 and provides tactile feedback to the wearer. Similarly, ringer 575, a suitable example of which is the Model SMT916A ringer sold by Projects Unlimited, Inc. of Dayton, Ohio, is coupled to processing unit 490 through ringer driver 580, a suitable example of which is the Model MMBTA14 CTI darlington transistor driver sold by Motorola, Inc. of Schaumburg, Ill., and provides audible feedback to the wearer. Feedback may include, for example, celebratory, cautionary and other threshold or event driven messages, such as when a wearer reaches a level of calories burned during a workout.

Also provided on PCB 445 and coupled to processing unit 490 is momentary switch 585. Momentary switch 585 is also coupled to button 470 for activating momentary switch 585. LEDs 475, used to provide various types of feedback information to the wearer, are coupled to processing unit 490 through LED latch/driver 590.

Oscillator 595 is provided on PCB 445 and supplies the system clock to processing unit 490. Reset circuit 600, accessible and triggerable through a pin-hole in the side of computer housing 405, is coupled to processing unit 490 and enables processing unit 490 to be reset to a standard initial setting.

Rechargeable battery 450, which is the main power source for the armband sensor device 400, is coupled to processing unit 490 through voltage regulator 605. Finally, memory functionality is provided for armband sensor device 400 by SRAM 610, which stores data relating to the wearer of armband sensor device 400, and flash memory 615, which stores program and configuration data, provided on PCB 445. SRAM 610 and flash memory 615 are coupled to processing unit 490 and each preferably have at least 512 K of memory.

In manufacturing and assembling armband sensor device 400, top portion 435 of computer housing 405 is preferably formed first, such as by a conventional molding process, and flexible wing body 410 is then overmolded on top of top portion 435. That is, top portion 435 is placed into an appropriately shaped mold, i.e., one that, when top portion 435 is placed therein, has a remaining cavity shaped according to the desired shape of flexible wing body 410, and flexible wing body 410 is molded on top of top portion 435. As a result, flexible wing body 410 and top portion 435 will merge or bond together, forming a single unit. Alternatively, top portion 435 of computer housing 405 and flexible wing body 410 may be formed together, such as by molding in a single mold, to form a single unit. The single unit however formed may then be turned over such that the underside of top portion 435 is facing upwards, and the contents of computer housing 405 can be placed into top portion 435, and top portion 435 and bottom portion 440 can be affixed to one another. As still another alternative, flexible wing body 410 may be separately formed, such as by a conventional molding process, and computer housing 405, and in particular top portion 435 of computer housing 405, may be affixed to flexible wing body 410 by one of several known methods, such as by an adhesive, by snap-fitting, or by screwing the two pieces together. Then, the remainder of computer housing 405 would be assembled as described above. It will be appreciated that rather than assembling the remainder of computer housing 405 after top portion 435 has been affixed to flexible wing body 410, the computer housing 405 could be assembled first and then affixed to flexible wing body 410.

Figure 21:
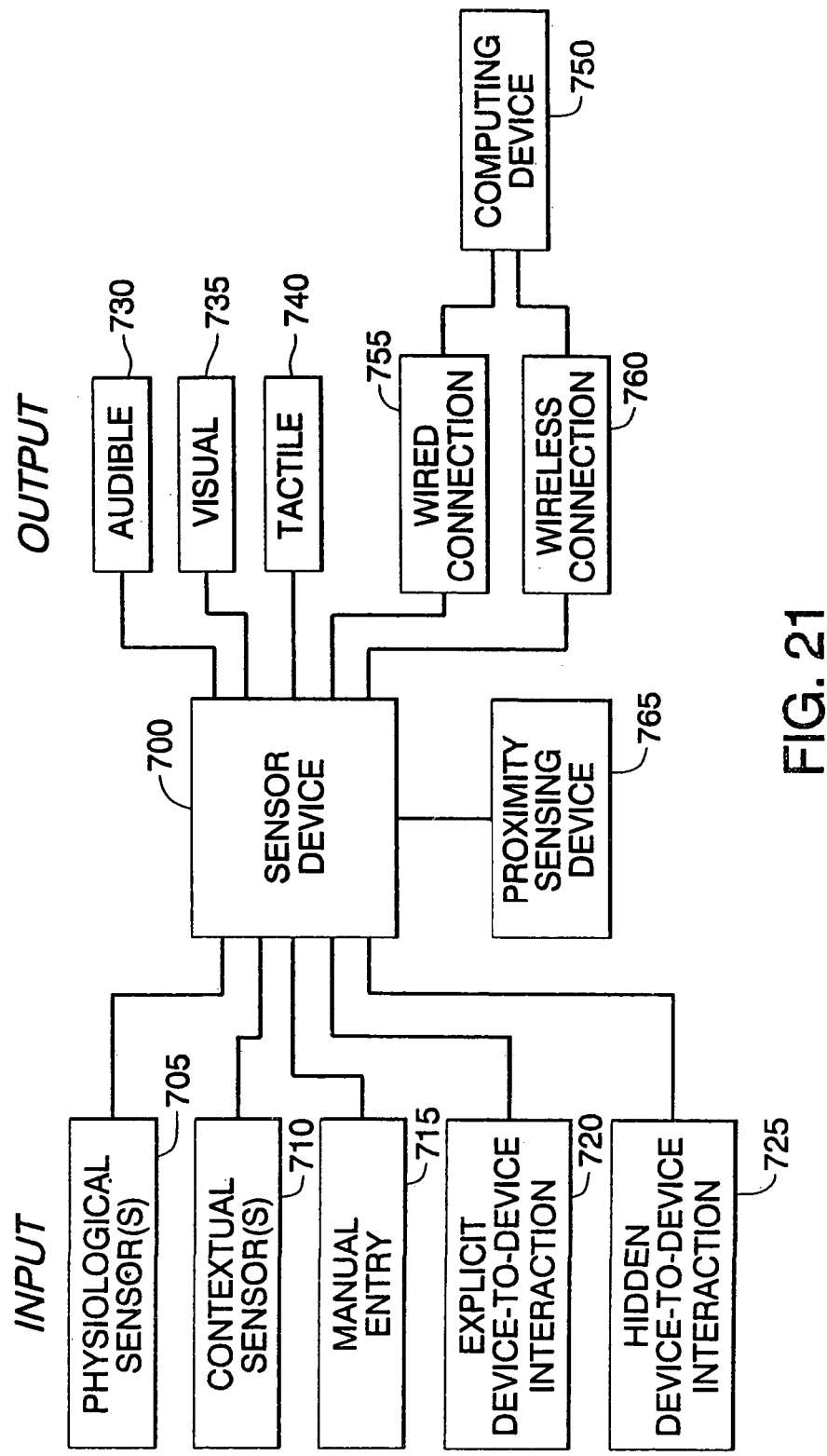
FIG. 21 is a block diagram of an apparatus for monitoring health, wellness and fitness according to an alternate embodiment of the present invention.

Referring to FIG. 21, a block diagram of an alternate embodiment of the present invention is shown. This alternate embodiment includes stand alone sensor device 700 which functions as an independent device, meaning that it is capable of collecting and/or generating the various types of data described herein in connection with sensor device 10 and sensor device 400 and providing analytical status data to the user without interaction with a remotely located apparatus such as central monitoring unit 30. Stand alone sensor device 700 includes a processor that is programmed and/or otherwise adapted to include the utilities and algorithms necessary to create analytical status data from the data indicative of various physiological and/or contextual parameters of the user, the data derived therefrom, and the data input by the user, all of which is stored in and accessed as needed from memory provided in stand alone sensor device 700. Stand alone sensor device 700 may comprise sensor device 10 shown in FIGS. 1 and 2 that includes microprocessor 20 and memory 22 or armband sensor device 400 shown in FIGS. 12-17 that includes processing unit 490 and SRAM 610.

As shown schematically in FIG. 21, data may be input into stand alone sensor device 700 in a number of ways. Stand alone sensor device 700 may include one or more physiological sensors 705 as described herein for facilitating the collection of data indicative of various physiological parameters of the user. Stand alone sensor device 700 may also include one or more contextual sensors 710 as described herein for facilitating the collection of data indicative of various contextual parameters of the user. As indicated by reference number 715, stand alone sensor device 700 maybe adapted to enable the manual entry of data by the user. For example, stand alone sensor device 700 may include a data input button, such as a button 470 of armband sensor device 400, through which a user could manually enter information such as information relating to various life activities of the user as described herein or information relating to the operation and/or control of stand alone sensor device 700, for example, the setting of reminders or alerts as described herein. In this example, activation of button 470 may simply record or time stamp that an event such as a meal has occurred, with the wearer needing to assign a meaning to that time stamp through data entry at a later time. Alternatively, activation of button 470 in certain sequences, such as one activation, two successive activations, three successive activations, etc., can be preset to have different specific meanings. A wearer would need to follow a menu or guide of such preset activation sequences to input relevant data. Alternatively, stand alone sensor device 700 may include a more sophisticated means for manual entry of information such as a keypad, a touch screen, a microphone, or a remote control device, for example a remote control device incorporated into a wristwatch. In the case of a microphone, the processor of stand alone sensor device 700 would be provided with well known voice recognition software or the like for converting the input speech into usable data.

As indicated by reference numbers 720 and 725, information comprising data indicative of various physiological and/or contextual parameters and data derived therefrom may be input into stand alone sensor device 700 through interaction with other devices. In addition, information such as handshake data or data indicative of various physiological and/or contextual parameters and data derived therefrom may be output from stand alone sensor device 700 to such other devices. According to one embodiment, the interaction is in the form of wireless communication between stand alone sensor device 700 and another device capable of wireless communication by way of a wireless transceiver provided in stand alone sensor device 700, such as wireless transceiver 565 shown and described in connection with FIG. 20. The device-to-device interaction may, as shown by reference number 720, be explicit, meaning that the user of stand alone sensor device 700 has knowingly initiated the interaction. For example, a user may activate a button on a scale to upload data to stand alone sensor device 700. The device-to-device interaction may also, as shown by reference number 725, be hidden, meaning that the user of stand alone sensor device 700 does not knowingly initiate the interaction. For example, a gym may have a sensor that wirelessly transmits a signal to sensing device 700 when the user enters and leaves the gym to time stamp when the user began and ended a workout.

As shown schematically in FIG. 21, information may be output or transmitted from stand alone sensor device 700 in a number of ways. Such information may include the data indicative of various physiological parameters and/or contextual parameters, the data derived therefrom, the data manually input by the user, the analytical status data, or any combination thereof. As shown by reference numbers 730, 735 and 740, information may be output or transmitted in an audible fashion such as by a series of tones or beeps or a recorded voice by a device such as a speaker, in a visual fashion such as by one or more LEDs, or in a tactile fashion such as by vibration. For example, stand alone sensor device 700 may be adapted to output a tone or tones, light an LED or LEDs, or vibrate as a reminder for an event, such as a reminder to eat or exercise at a particular time, or when a goal has been reached, such as a target number of calories burned during a workout, or a condition has been sensed, such as ovulation. Alternatively, stand alone sensor device 700 may be provided with a more sophisticated visual output means such as an LCD similar to those found on commercially available cell phones, pagers and personal digital assistants. With an LCD or a similar device and the expanded visual output capabilities it would provide, stand alone sensor device 700 may be adapted to output or transmit some or all of the information described in connection with FIGS. 5 through 11 in the same or a similar format. For example, stand alone sensor device 700 could provide analytical status data in the form of the Health Index to the user. As a further alternative, stand alone sensor device 700 may be coupled to computing device 750 such as a personal computer, a cell phone, a pager, a personal digital assistant, another stand alone sensor device 700 or any other device having a processor by either wired connection 755 or wireless connection 760. For example, battery recharger unit 480 shown in FIG. 19 may be used to provide the wired connection 755 or wireless connection 760. In this configuration, the display of the computing device could be used to visually output information from stand alone sensor device 700. It will be appreciated that since computing device 750 includes a sophisticated output means such as an LCD, it may be used to output or transmit to the user some or all of the information described in connection with FIGS. 5 through 11, such as the Health Index, in the same or a similar format.

Also, computing device 750 may in turn be used to control other devices, such as the lights or thermostat in a home, based on data output by stand alone sensor device 700, such as the fact that the wearer has fallen asleep or the fact that the wearer's skin temperature has reached a certain level. In other words, stand alone sensor device 700, and in particular its processor, may be adapted to cause a computing device 750 to trigger an event upon detection of one or more physiological and/or contextual conditions by stand alone sensor device 700. Alternatively, stand alone sensor device 700 may be adapted to cause a computing device 750 to trigger an event based upon information received from another computing device 750.

Stand alone sensor device 700 may be adapted to interact with and influence an interactive electronic media device, such as a video game, or non-interactive electronic media device, such as on a display device such as a DVD or digital video disc player playing a digitally recorded movie. For example, stand alone sensor device 700 may be adapted to transmit information relating to the physiological state of the wearer to the video game, which in turn adjusts the characteristics of the game, such as the level of difficulty. As another example, stand alone sensor device 700 may be adapted to transmit information relating to the physiological state of the wearer to the device displaying the digitally recorded movie which in turn adjusts the characteristics, such as the outcome, of the movie.

Furthermore, stand alone sensor device 700 may include location sensing device 765, such as an ultrasonic or a radio-frequency identification tag, for enabling a computing device 750 to detect the geographic location of stand alone sensor device 700, such as the location of stand alone sensor device 700 within a defined space such as a building. In one embodiment, a location indication causes computing device 750 to trigger an event, such as lowering the temperature in a room corresponding to the indicated location, preferably based on the detection by stand alone sensor device 700 of one or more physiological conditions of the wearer, such as skin temperature. In another embodiment, the location indication causes computing device 750 to trigger an event, such as lowering the temperature in a room corresponding to the indicated location, if stand alone sensor device 700 detects one or more physiological conditions, such as a skin temperature of the wearer being above a certain level. In addition, the input means of the computing device, such as the mouse and keyboard of a personal computer, the keypad of a cell phone or pager, or the touch screen of a personal digital assistant, may be used to manually input information into stand alone sensor device 700.

The different modes of output may be used in combination to provide different types and levels of information to a user. For example, stand alone sensor device 700 could be worn by an individual while exercising and an LED or a tone can be used to signal that a goal of a certain number of calories burned has been reached. The user could then transmit additional data wirelessly from stand alone sensor device 700 to a computing device 750 such as a cell phone after he or she is finished exercising to view data such as heart rate and/or respiration rate over time.

As a further alternative embodiment of the present invention, rather than the processor provided in stand alone sensor device 700 being programmed and/or otherwise adapted to generate the derived data and to include the utilities and algorithms necessary to create analytical status data, computing device 750 could be so programmed. In this embodiment, stand alone sensor device 700 collects and/or generates the data indicative of various physiological and/or contextual parameters of the user, the data manually input by the user, and/or data input as a result of device-to-device interaction shown at 720 and 725, all of which is stored in the memory provided in stand alone sensor device 700. This data is then periodically uploaded to computing device 750 which in turn generates derived data and/or analytical status data. Alternatively, the processor of stand alone sensor device 700 could be programmed to generate the derived data with computing device 750 being programmed and/or otherwise adapted to include the utilities and algorithms necessary to create analytical status data based on data indicative of one or more physiological and/or contextual parameters, data derived therefrom, data manually input by the user and/or data input as a result of device-to-device interaction shown at 720 and 725 uploaded from stand alone sensor device 700. As still a further alternative, the processor of stand alone sensor device 700 could be programmed and/or otherwise adapted to include the utilities and algorithms necessary to create analytical status data based on data indicative of one or more physiological and/or contextual parameters, data derived therefrom, data manually input by the user and/or data input as a result of device-to-device interaction shown at 720 and 725 uploaded from stand alone sensor device 700 with computing device 750 being programmed to generate the derived data. In either alternative, any or all of the data indicative of physiological and/or contextual parameters of the user, the data derived therefrom, the data manually input by the user, the data input as a result of device-to-device interaction shown at 720 and 725 and the analytical status data may then be viewed by the user using the output means of the programmed computing device 750 or another computing device 750 to which the data is downloaded. In the latter alternative, everything but the analytical status data may also be output by stand alone sensor device 700 as described herein.

Computing device 750 in these alternative embodiments may be connected to an electronic network, such as the Internet, to enable it to communicate with central monitoring unit 30 or the like. The programming of computing device 750 that enables it to generate the derived data and/or the analytical status data may, with such a configuration, be modified or replaced by downloading the relevant data to computing device 750 over the electronic network.

As still a further alternative embodiment, computing device 750 may be provided with a custom written plug-in adapted to provide data display functionality through use of a well known browser program. In this embodiment, stand alone sensor device 700 collects and/or generates the data indicative of various physiological and/or contextual parameters of the user, the derived data, the data input by the user, data input as a result of device-to-device interaction shown at 720 and 725, and/or analytical status data based thereon and uploads this data to computing device 750. The plug-in provided in computing device 750 then generates appropriate display pages based on the data which may be viewed by the user using the browser provided with computing device 750. The plug-in may be modified/updated from a source such as central monitoring unit 30 over an electronic network such as the Internet.

Referring to FIGS. 22-26, an alternate embodiment of a sensor device is shown at 800. Sensor device 800 may be a specific embodiment of either sensor device 10 described in connection with FIGS. 1-11 or stand alone sensor device 700 described in connection with FIG. 21. Sensor device 800 includes housing 805 affixed to flexible section 810, which is similar to flexible wing body 410 shown in FIGS. 12-17. Flexible section 810 is adapted to engage, such as by wrapping around or conforming to, at least a portion of the human body, such as the upper arm, to enable sensor device 800, in combination with a removable strap 811 inserted through slots 812 provided in flexible section 810, to be worn on the body. Preferably, flexible section 810 is made of a material having a durometer of between 75 and 85 Shore A. Flexible section 810 may take on a variety of shapes and may be made of a cloth material, a flexible plastic film, or an elastic material having an adhesive similar in structure to a Band-Aid® disposable adhesive bandage. In the embodiment shown in FIGS. 22-26, housing 805 is permanently affixed to flexible section 810, such as by an over molding or co-molding process, through the use of an adhesive material, or by a fastening mechanism such as one or more screws. Housing 805 includes top portion 815 affixed to bottom portion 820 by any known means, including, for example, an adhesive material, screws, snap fittings, sonic welding, or thermal welding. According to a preferred embodiment, a watertight seal is provided between top portion 815 and bottom portion 820. Such a water-tight seal is provided when sonic welding or thermal welding is used. Alternatively, an O-ring could be provided between top portion 815 and bottom portion 820 to create the water-tight seal.

Figure 22:
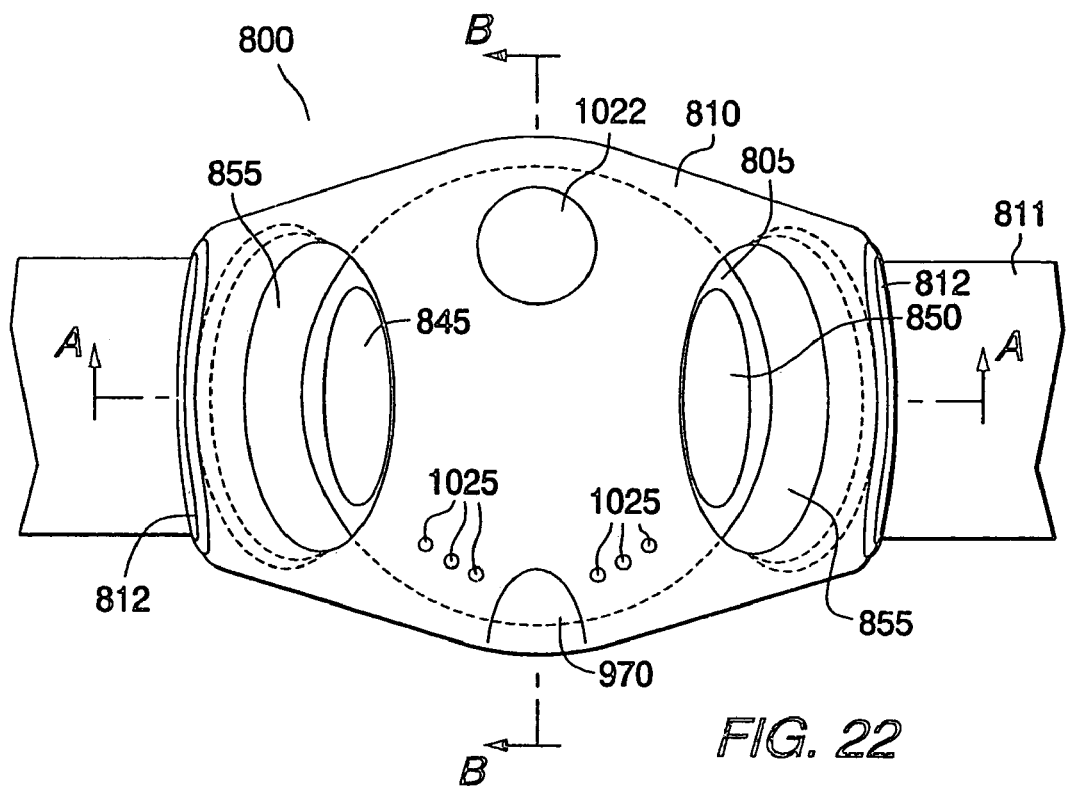
FIG. 22 is a front view of an alternate embodiment of a sensor device according to the present invention.
Figure 23:
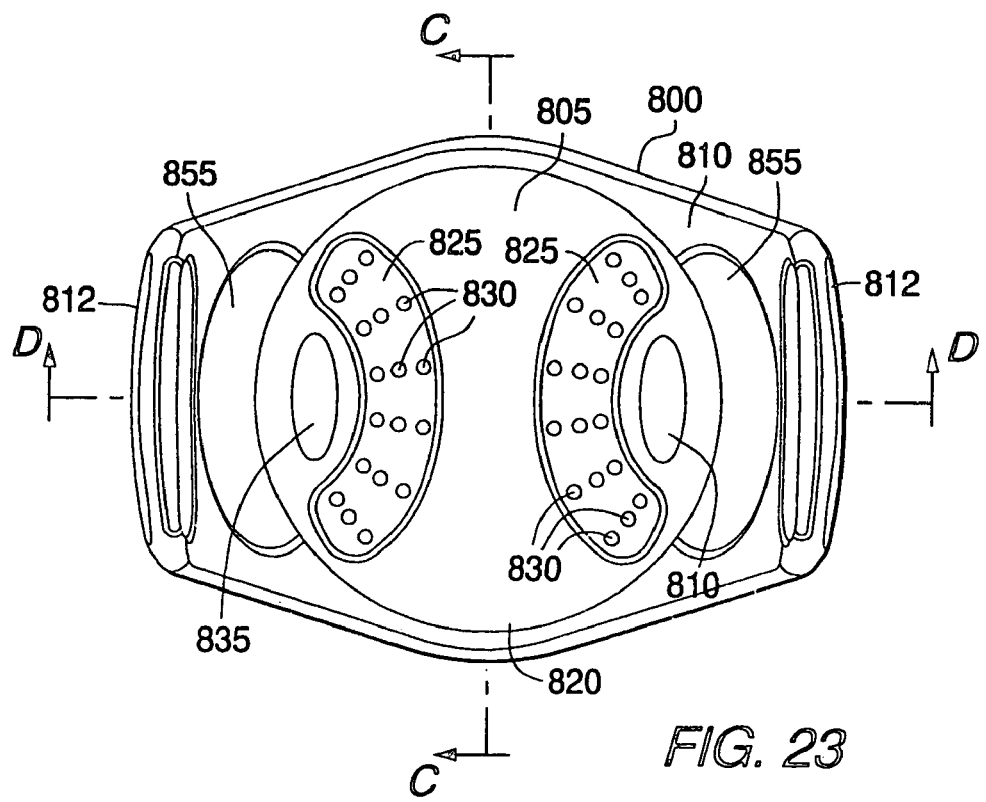
FIG. 23 is a back view of an alternate embodiment of a sensor device according to the present invention.
Figure 24:
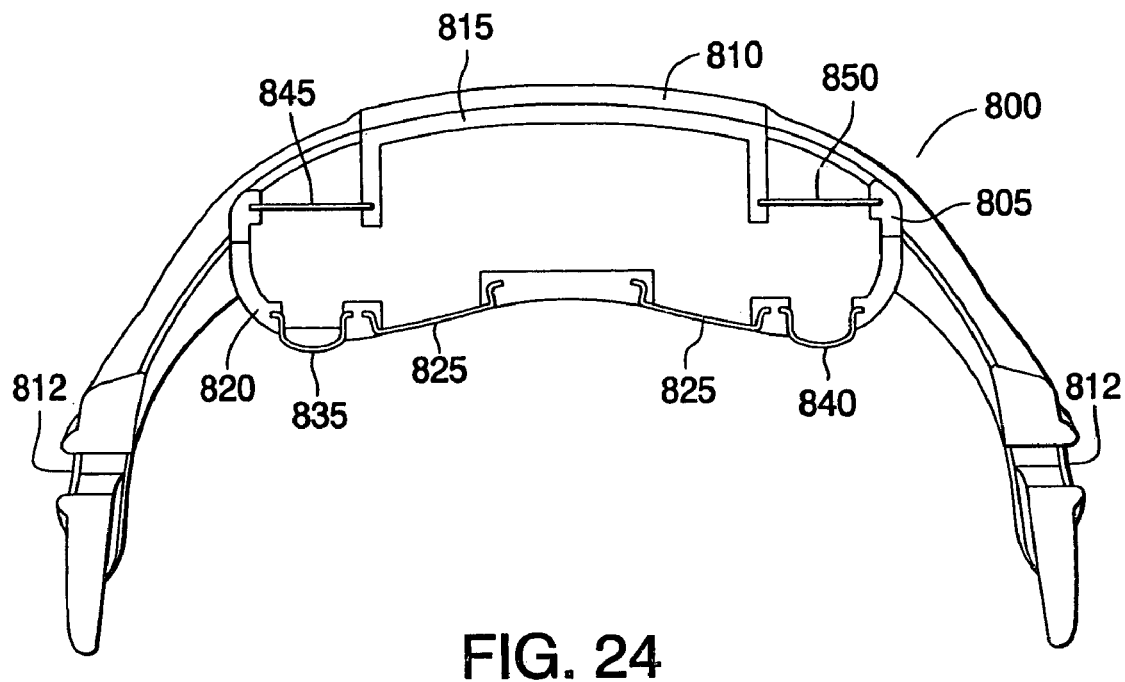
FIG. 24 is a cross-sectional view of the sensor device shown in FIG. 22 taken along lines A-A.
Figure 25:
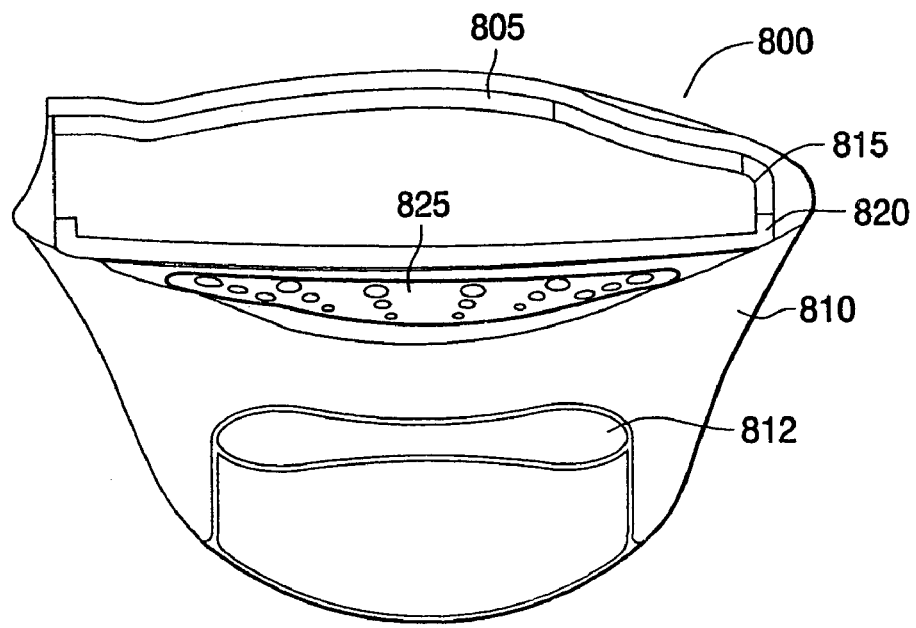
FIG. 25 is a cross-sectional view of the sensor device shown in FIG. 22 taken along lines B-B.
Figure 26:
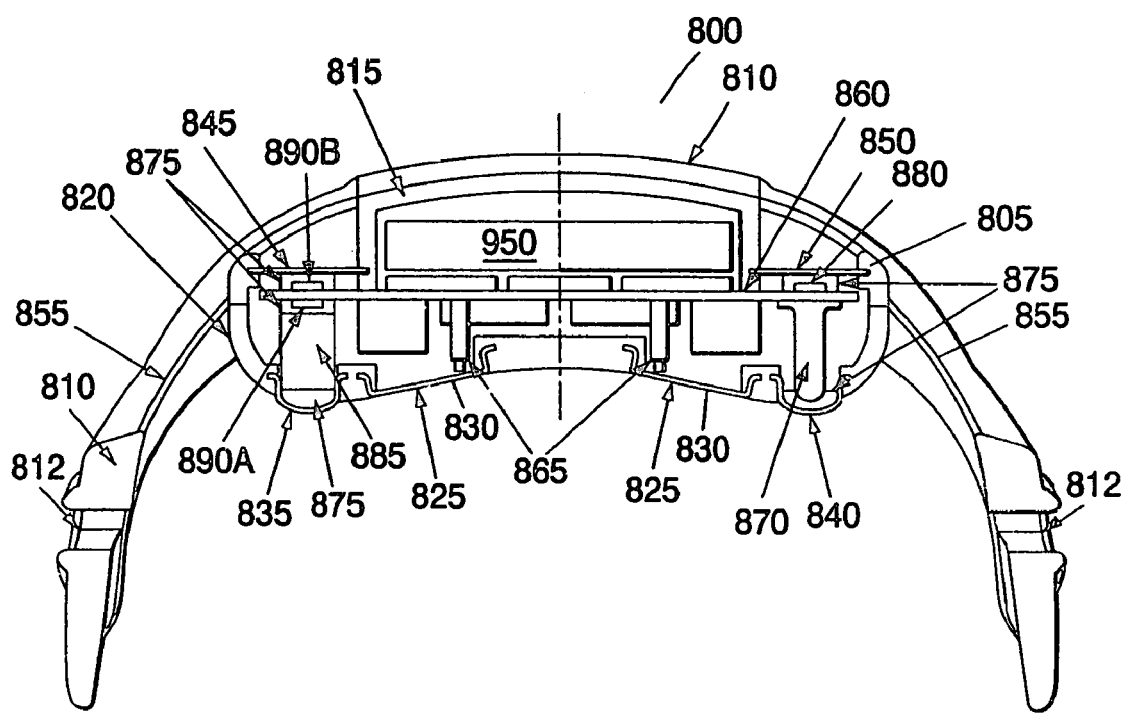
FIG. 26 is a cross-sectional view of the sensor device shown in FIG. 22 taken along lines A-A showing the internal components of the housing of the sensor device.

As can be seen most readily in FIGS. 23, 24 and 26, affixed to bottom portion 820 of housing 805 are GSR sensors 825. GSR sensors 825 measure the conductivity of the skin between two points and may comprise electrodes formed of a material such as stainless steel, gold or a conductive carbonized rubber. Preferably, GSR sensors 825 have an oblong, curved shape as shown in FIG. 23, much like a kidney bean shape, that allows some portion of GSR sensors 825 to maintain contact with the body even if sensor device 800 is rocking or otherwise moving while being worn. Most preferably, GSR sensors 825 include raised bumps 830, or some other three-dimensional textured surface, along the surface thereof to perturb the skin and push between hairs to ensure good contact with the skin. In addition, raised bumps 830 provide channels for the movement of sweat underneath sensor device 800, rather than trapping sweat, no matter the orientation of sensor device with respect to the body. Also affixed to bottom portion 820 are heat flux skin interface component 835 and skin temperature skin interface component 840, each comprising a plate made of a thermally conductive material such as stainless steel. Preferably, heat flux skin interface component 835 and skin temperature skin interface component 840 are made of a material having thermal conduction properties of at least 12.9 W/mK, such as 304 stainless steel. Preferably, GSR sensors 825 are spaced at least 0.44 inches apart from one another, and at least 0.09 inches apart from heat flux skin interface component 835 and skin temperature skin interface component 840. GSR sensors 825, heat flux skin interface component 835 and skin temperature skin interface component 840 are adapted to be in contact with the wearer's skin when sensor device 800 is worn, and facilitate the measurement of GSR, heat flux from the body and skin temperature data. As can be seen most readily in FIGS. 22, 24 and 26, affixed to top portion 815 of housing 805 are heat flux ambient interface component 845 and ambient temperature interface component 850, which also are made of a thermally conductive material such as stainless steel, preferably a material having thermal conduction properties of at least 12.9 W/mK, such as 304 stainless steel. Heat flux ambient interface component 845 and ambient temperature interface component 850 facilitate the measurement of heat flux from the body and ambient temperature, respectively, by providing a thermal interface to the surrounding environment. To further enhance the measurement of these parameters, holes 855 are provided in flexible section 810 to expose heat flux ambient interface component 845 and ambient temperature interface component 850 to the ambient air. Preferably, holes 855 are sized so that flexible section 810 occludes as little skin as possible in the regions surrounding heat flux ambient interface component 845 and ambient temperature interface component 850 so as to allow air flowing off of the skin of the wearer to pass these components.

GSR Sensors 825, heat flux, skin interface component 835, skin temperature skin interface component 840, or any other sensing component that comes into contact with the skin may be provided with a plurality of microneedles for, among other things, enhancing electrical contact with the skin and providing real time access to interstitial fluid in and below the epidermis, which access may be used to measure various parameters such as pH level of the skin through electrochemical, impedance based or other well known methods. Microneedles enhance electrical contact by penetrating the stratum corneum of the skin to reach the epidermis. Such microneedles are well known in the art and may be made of a metal or plastic material. Prior art microneedles are described in, for example, U.S. Pat. No. 6,312,612 owned by the Procter and Gamble Company. Based on the particular application, the number, density, length, width at the point or base, distribution and spacing of the microneedles will vary.

Referring to FIG. 26, which is a cross-section taken along lines A-A in FIG. 22, the internal components of sensor device 800, housed within housing 805, are shown. Printed circuit board or PCB 860 is affixed to top portion 815 of housing 805 and receives and supports the electronic components provided inside housing 805. Affixed to a bottom side of PCB 860 and electronically coupled to GSR sensors 825 are contacts 865, which preferably comprise gold plated contact pins such as the Pogo® contacts available from Everett Charles Technologies in Pomona, Calif. Also affixed to the bottom side of PCB 860 is skin temperature thermistor 870, a suitable example of which is the model 100K6D280 thermistor manufactured by BetaTherm Corporation in Shrewsbury, Mass. Skin temperature thermistor 870 is, according to a preferred embodiment, thermally coupled to skin temperature skin interface component 840 by a thermally conductive interface material 875. Thermally conductive interface material 875 may be any type of thermally conductive interface known in the art, including, for example, thermally conductive gap fillers, thermally conductive phase change interface materials, thermally conductive tapes, thermally conductive cure-in-place compounds or epoxies, and thermal greases. Suitable thermally conductive interface materials include a boron nitride filled expanded polytetrafluoroethylene matrix sold under the trademark PolarChip CP8000 by W. L. Gore & Associates, Inc. and a boron nitride and alumina filled silicone elastomer on an adhesive backed 5 mil. (0.013 cm) thick aluminum foil carrier called A574, which is available from the Chomerics division of Parker Hannefin Corp. located in Woburn, Mass.

Provided on top of PCB 860 is near-body ambient temperature thermistor 880, a suitable example of which is the model NTHS040ZN0IN100KJ thermistor manufactured by Vishay Intertechnology, Inc. in Malvern, Pa. Near-body ambient temperature thermistor 880 is thermally coupled to ambient temperature interface component 850 by thermally conductive interface material 875.

Still referring to FIG. 26, a preferred embodiment of sensor device 800 includes a particular embodiment of an apparatus for measuring heat flux between a living body and the ambient environment described in co-pending application Ser. No. 09/822,890, the disclosure of which is incorporated herein by reference in its entirety. Specifically, heat conduit 885 is provided within housing 805. As used herein, the term heat conduit refers to one or more heat conductors which are adapted to singly or jointly transfer heat from one location to another, such as a conductor made of stainless steel. Heat conduit 885 is thermally coupled to heat flux skin interface component 835 by thermally conductive interface material 875. Provided on the bottom side of PCB 860 is a first heat flux thermistor 890A, and provided on the top side of PCB 860 is a second heat flux thermistor 890B. PCB 860 acts as a base member for supporting these components. It will be appreciated that a base member separate and apart from PCB 860 may be substituted therefor as an alternative configuration. A suitable example of both heat flux thermistors 890A and 890B is the. Heat flux Thermistor 890A and 890B are soldered to pads provided on PCB 860. The second heat flux thermistor 890B is thermally coupled to heat flux ambient interface 845 by thermally conductive interface material 875. As is well-known in the art, PCB 860 is made of a rigid or flexible material, such as a fiberglass, having a preselected, known thermal resistance or resistivity K. The heat flux off of the body of the wearer can be determined by measuring a first voltage V1 with heat flux thermistor 890A and a second voltage V2 with heat flux thermistor 890B. These voltages are then electrically differenced, such as by using a differential amplifier, to provide a voltage value that, as is well known in the art, can be used to calculate the temperature difference (T2−T1) between the top and bottom sides of PCB 860. Heat flux can then be calculated according to the following formula:

Heat Flux=$K(T2-T1)$

The combination of PCB 860 and heat flux thermistors 890A and 890B are thus a form of a heat flux sensor One advantage of the configuration of the apparatus for measuring heat flux shown in FIG. 26 is that, due to the vertical orientation of the components, assembly of the apparatus for measuring heat flux, and thus sensor device 800 as a whole, is simplified. Also adding to the simplicity is the fact that thermally conductive interface materials that include a thin adhesive layer on one or both sides may be used for thermally conductive interface materials 875, enabling components to be adhered to one another. In addition, thermistors 890A and 890B are relatively inexpensive components, as compared to an integral heat flux sensor such as those commercially available from RdF Corporation of Hudson, N.H., thereby reducing the cost of sensor device 800. Although heat flux thermistors 890A and 890B are described as being provided on PCB 860 in the embodiment shown in FIG. 26, it will be appreciated that any piece of material having a known resistivity K may be used. Furthermore, other temperature measuring devices known in the art, such as a thermocouple or thermopile, may be substituted for heat flux thermistors 890A and 890B. As a further alternative, heat conduit 885 may be omitted such that thermal communication between heat flux thermistor 890A and heat flux skin interface component 835 is provided by one or more pieces of thermally conductive interface material 875. As still a further alternative, heat flux skin interface component 835 may be omitted such that thermal communication between heat flux thermistor 890A and the skin is provided by either or both of heat conduit 885 and one or more pieces of thermally conductive interface material 875. In any of the embodiments described herein, the combination of one or more of heat conduit 885, one or more pieces of thermally conductive interface material 875, and heat flux skin interface component 835 act as a thermal energy communicator for placing heat flux thermistor 890A in thermal communication with the body of the wearer of sensor device 800.

Figure 27:
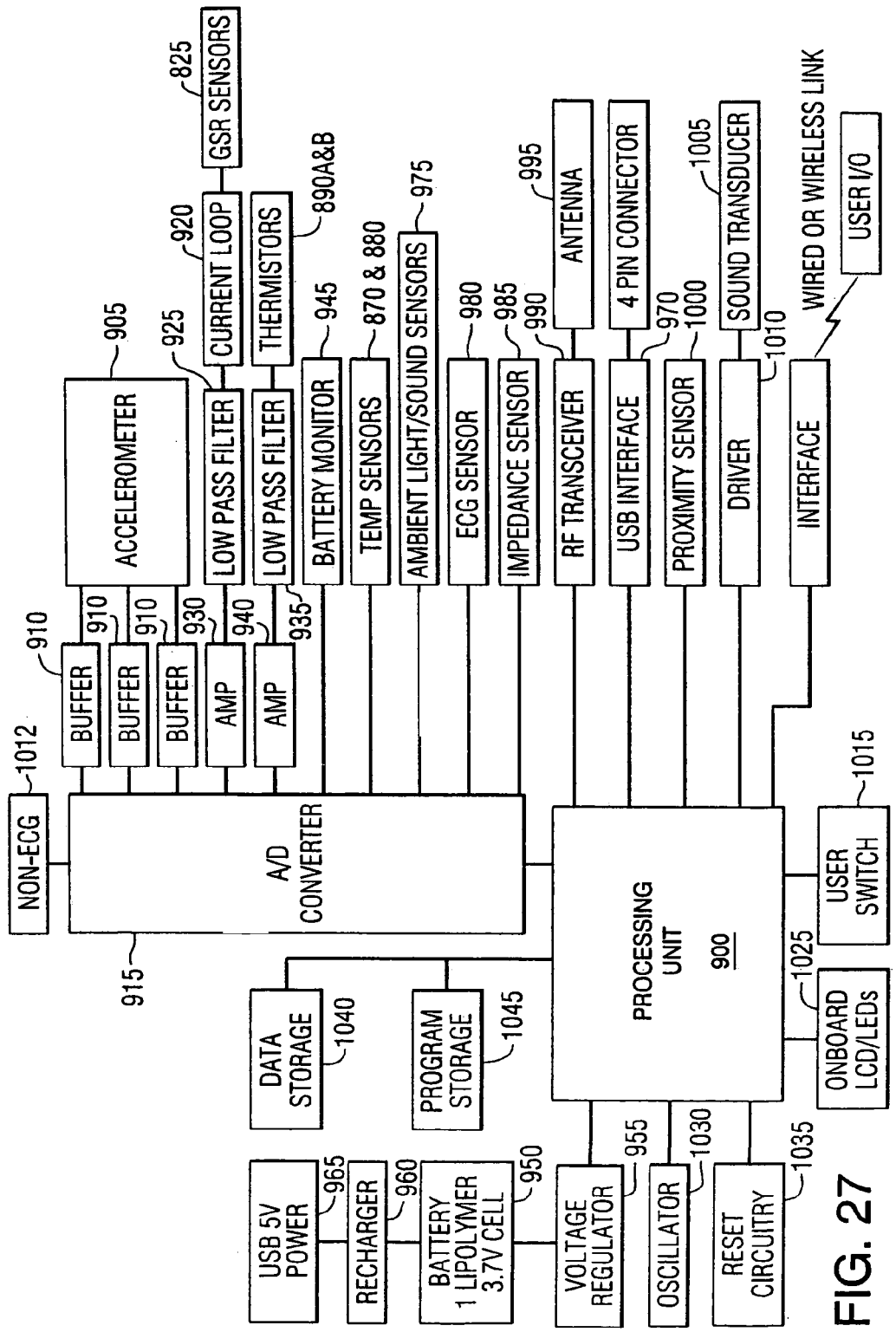
FIG. 27 is a block diagram illustrating the components mounted on or coupled to the printed circuit board forming a part of an embodiment of the sensor device shown in FIGS. 22 through 26.

FIG. 27 is a schematic diagram that shows an embodiment of the system architecture of sensor device 800, and in particular each of the components that is either provided on or coupled to PCB 860.

As shown in FIG. 27, PCB 860 includes processing unit 900, which maybe a microprocessor, a microcontroller, or any other processing device that can be adapted to perform the functionality described herein, in particular the functionality described in connection with microprocessor 20 shown in FIG. 2, processing unit 490 shown in FIG. 20, or stand alone sensor device 700 shown in FIG. 21. A suitable example of processing unit 900 is the Dragonball EZ sold by Motorola, Inc. of Schaumburg, Ill. Also provided on PCB 860 is accelerometer 905, which may be either a two-axis or a three-axis accelerometer. A suitable example of a two-axis accelerometer is the Model ADXL202 accelerometer sold by Analog Devices, Inc. of Norwood, Mass., and a suitable example of a three-axis accelerometer is the model ACH-04-08-05 accelerator sold by Measurement Specialties Incorporated in Norristown, Pa. The output signals of accelerometer 905 are passed through buffers 910 and input analog to digital, referred to as A/D, converter 915 that in turn is coupled to processing unit 900. GSR sensors 825 are coupled to A/D converter 915 through current loop 920, low pass filter 925, and amplifier 930. Current loop 920 comprises an opamp and a plurality of resistors, and applies a small, fixed current between the two GSR sensors 825 and measures the voltage across them. The measured voltage is directly proportional to the resistance of the skin in contact with the electrodes. Similarly, heat flux thermistors 890A and 890B are coupled to A/D converter 915 and processing unit 900, where the heat flux calculations are performed, through low pass filter 935 and amplifier 940.

Battery monitor 945, preferably comprising a voltage divider with low pass filter to provide average battery voltage, monitors the remaining power level of rechargeable battery 950. Rechargeable battery 950 is preferably a LiIon/LiPolymer 3.7 V Cell. Rechargeable battery 950, which is the main power source for sensor device 800, is coupled to processing unit 900 through voltage regulator 955. Rechargeable battery 950 may be recharged either using recharger 960 or USB cable 965, both of which may be coupled to sensor device 800 through USB interface 970. Preferably, USB interface 970 is hermetically sealable, such as with a removable plastic or rubber plug, to protect the contacts of USB interface 970 when not in use.

PCB 860 further includes skin temperature thermistor 870 for sensing the temperature of the skin of the wearer of sensor device 800, and near-body ambient temperature thermistor 880 for sensing the ambient temperature in the area near the body of the wearer of sensor device 800. Each of these components is biased and coupled to processing unit 900 through A/D converter 915.

According to a specific embodiment of sensor device 800, PCB 860 may include one or both of an ambient light sensor and an ambient sound sensor, shown at 975 in FIG. 27, coupled to A/D converter 915. The ambient light sensor and ambient sound sensor may be adapted to merely sense the presence or absence of ambient light or sound, the state where a threshold ambient light or sound level has been exceeded, or a reading reflecting the actual level of ambient light or sound. A suitable example of an ambient sound sensor is the WM-60A Condenser Microphone Cartridge sold by Matsushita Electric Corporation of America located in Secaucus, N.J., and suitable examples of an ambient light sensor are the Optek OPR5500 phototransistor and the Optek OPR5910 photodiode sold by Optek Technology, Inc. located in Carrollton, Tex. In addition, PCB 860 may include ECG sensor 980, including two or more electrodes, for measuring the heart rate of the wearer, and impedance sensor 985, also including a plurality of electrodes, for measuring the impedance of the skin of the wearer. Impedance sensor 985 may also be an EMG sensor which gives an indication of the muscular activity of the wearer. The electrodes forming part of ECG sensor 980 or impedance sensor 985 may be dedicated electrodes for such sensors, or may be the electrodes from GSR sensors 825 multiplexed for appropriate measurements. ECG sensor 980 and impedance sensor 985 are each coupled to A/D converter 915.

PCB 860 further includes RF transceiver 990, coupled to processing unit 900, and antenna 995 for wirelessly transmitting and receiving data to and from wireless devices in proximity to sensor device 800. RF transceiver 990 and antenna 995 may be used for transmitting and receiving data to and from a device such as a treadmill being used by a wearer of sensor device 800 or a heart rate monitor worn by the wearer of sensor device 800, or to upload and download data to and from a computing device such as a PDA or a PC. In addition, RF transceiver 990 and antenna 995 may be used to transmit information to a feedback device such as a bone conductivity microphone worn by a fireman to let the fireman know if a condition that may threaten the fireman's safety, such as hydration level or fatigue level, has been sensed by sensor device 800. As described in detail in connection with FIG. 21, stand along sensor device 700 may be coupled to computing device 750 to enable data to be communicated therebetween. Thus, as a further alternative, RF transceiver 990 and antenna 995 may be used to couple sensor device 800 to a computing device such as computing device 750 shown in FIG. 21. Such a configuration would enable sensor device 800 to transmit data to and receive data from the computing device 750, for example a computing device worn on the wrist. The computing device could be used to enable a user to input data, which may then be stored therein or transmitted to sensor device 800, and to display data, including data transmitted from sensor device 800. The configuration would also allow for computing tasks to be divided between sensor device 800 and computing device 750, referred to herein as shared computing, as described in detail in connection with FIG. 21.

As shown in FIG. 27, PCB 860 may include proximity sensor 1000 which is coupled to processing unit 900 for sensing whether sensor device 800 is being worn on the body. Proximity sensor 1000 may also be used as a way to automatically power on and off sensor device 800. Proximity sensor preferably comprises a capacitor, the electrical capacitance of which changes as sensor device 800 gets closer to the body. PCB 860 may also include sound transducer 1005, such as a ringer, coupled to processing unit 900 through driver 1010.

Sensor device 800 may also be provided with sensors in addition to those shown in FIG. 27, such as those taught by U.S. Pat. No. 5,853,005, the disclosure of which is incorporated herein by reference. The '005 patent teaches a sound transducer coupled to a pad containing an acoustic transmission material. The pad and sound transducer may be used to sense acoustic signals generated by the body which in turn may be converted into signals representative of physiological parameters such as heart rate or respiration rate. In addition, rather than being integrated in sensor device 800 as part of one or more of housing 805, flexible section 810 or strap 811, a sensing apparatus as taught by the '005 patent may be provided separate from sensor device 800 and be coupled, wired or wirelessly, to sensor device 800. According to the '005, the sound or acoustic transducer is preferably a piezoelectric, electret, or condenser-based hydrophone, similar to those used by the Navy in sonar applications, but can be any other type of waterproof pressure and motion sensing type of sensor.

The sensing apparatus as taught by the '005 patent is an example of what shall be referred to herein as a non-ECG heart parameter sensor, meaning that it has the following two qualities: (1) it does not need to make measurements across the torso using at least two contact separated by some distance; and (2) it does not measure electrical activity of the heart. The sensing apparatus as taught by the '005 patent has been shown to be capable of detecting heart rate information and information relating to individual beats of the heart with high reliability under certain circumstances, depending primarily on factors including the proximity of the apparatus to the heart, the level of ambient noise, and motion related sound artifacts caused by the movement of the body. As a result, the sensing apparatus as taught by the '005 patent is most reliable when worn in an ambient environment with a low level of ambient noise and when the body is not moving.

Certain characteristics, sensors and sensing capabilities of sensor device 800 are able to improve the reliability and accuracy of an acoustic-based non-ECG heart parameter sensor 1012 such as the sensing apparatus as taught by the '005 patent that is incorporated therein or coupled thereto. For example, in one specific embodiment, sensor device 800 is particularly suited to be worn on the upper arm. The upper arm is a good location for a sensor device 800 having an acoustic-based non-ECG heart parameter sensor 1012 incorporated therein because it is near the heart and provides a space for sensor device that allows it to be unobtrusive and comfortable to wear. In addition, ambient sound sensor shown at 975 in FIG. 27 may be used to filter out ambient noise from the signals detected by the acoustic-based non-ECG heart parameter sensor 1012 in order to isolate the sound signal originating from the body. Filtering of the signal produced by an acoustic-based non-ECG heart parameter sensor 1012 such as the sensing apparatus as taught by the '005 patent in this manner may be used both in the case where such an apparatus is incorporated in sensor device 800 and in the case where it is separated from but coupled to sensor device 800 as described above. Furthermore, the sound generated from the motion of the body that is not created by the heart can be accounted for and adjusted for through the use of a sensor or sensors that detect or that may be used to identify body sounds generated as a result of motion of the body, such as accelerometer 905 shown in FIGS. 27 and 29 or the body position or muscle pressure sensors identified in Table 1. For example, footfalls create sound within the body that can lower the signal to noise ratio of an acoustic-based non-ECG heart parameter sensor 1012, which will likely result in false positive and false negative heart beat identifications. As is well known in the art, accelerometer 905 may function as a footfall indicator. Accelerometer 905 may thus be used to filter or subtract out from the signal detected by the acoustic-based non-ECG heart parameter sensor 1012 signals related sound motion artifacts caused by the movement of the body such as by footfalls.

Several methodologies for performing the filtering or subtracting of signals described herein are known to those of ordinary skill in the art. Such filtering or subtracting of signals used in connection with the monitoring of disparate signal, some used for noise cancellation and some used for their direct measure, is also known as data integration.

Sensor device 800 may also be used to put parameters around and provide a context for the readings made by a non-ECG heart parameter sensor 1012 so that inaccurate reading can be identified and compensated for. For example, sensor device 800 may be used to detect real time energy expenditure of the wearer as well as the type of activity in which the wearer is engaging, such as running or riding a bike. Thus, as another example of how the sensors and sensing capabilities of sensor device 800 may be used to increase the reliability and accuracy of a non-ECG heart parameter sensor 1012 through data integration, the energy expenditure and activity type information can be used to provide a context in which the heart related parameters detected by the non-ECG heart parameter sensor 1012 can be assessed and possibly filtered. For example, if sensor device 800 detects that a person is burning 13 calories per minute and is biking, and the non-ECG heart parameter sensor 1012 is indicating that the wearer's heart rate is 60 beats per minute, then it is highly likely that further filtration of the signal from the non-ECG heart parameter sensor 1012 is necessary.

Other well known non-ECG heart parameter sensing devices include, for example, those based on micro-power impulse radar technology, those based on the use of piezoelectric based strain gauges, and those based on plethysmography, which involves the measurement of changes in the size of a body part as modified by the circulation of blood in that part. It will be appreciated that the performance of these devices may also be enhanced through the use of data integration as described herein.

Another sensor that may be incorporated into the sensor device 800 measures the pressure with which sensor device 800 is held against the body of the wearer. Such a sensor could be capacitive or resistive in nature. One such instantiation places a piezo-resistive strain gauge on the back of the enclosure to measure the small deflection of the plastic as increasing force is applied. Data gathered from such a sensor can be used to compensate the readings of other sensors in sensor device 800 according to the readings of such a sensor.

Also provided on PCB 860 and coupled to processing unit 900 is switch 1015. Switch 1015 is also coupled to button 1020 provided on housing 805. Button 1020, by activating switch 1015, may be used to enter information into sensor device 800, such as a time stamp to mark the occurrence of an event such taking medication. Preferably, button 1020 has a tactile, positive d-tent feedback when depressed, and a concave shape to prevent accidental depression. Also, in the embodiment shown in FIGS. 22-26, flexible section 810 includes membrane 1022 that covers and seals button 1020.

Figure 28:
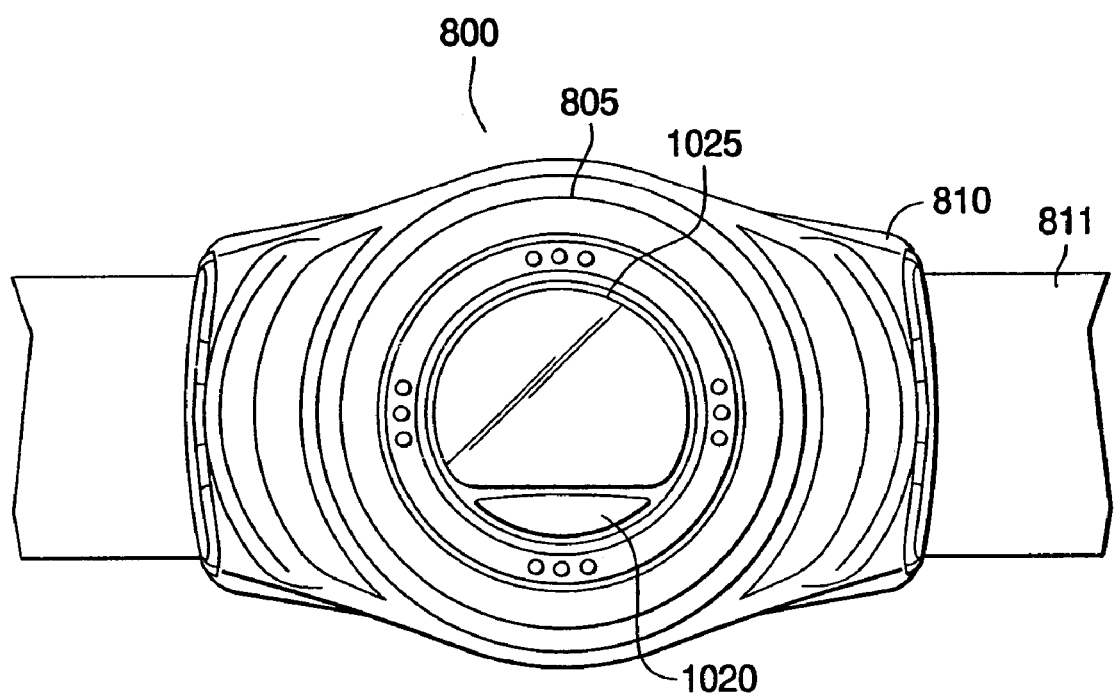
FIG. 28 is a front view of an alternate embodiment of a sensor device according to the present invention including an LCD.
Figure 30:
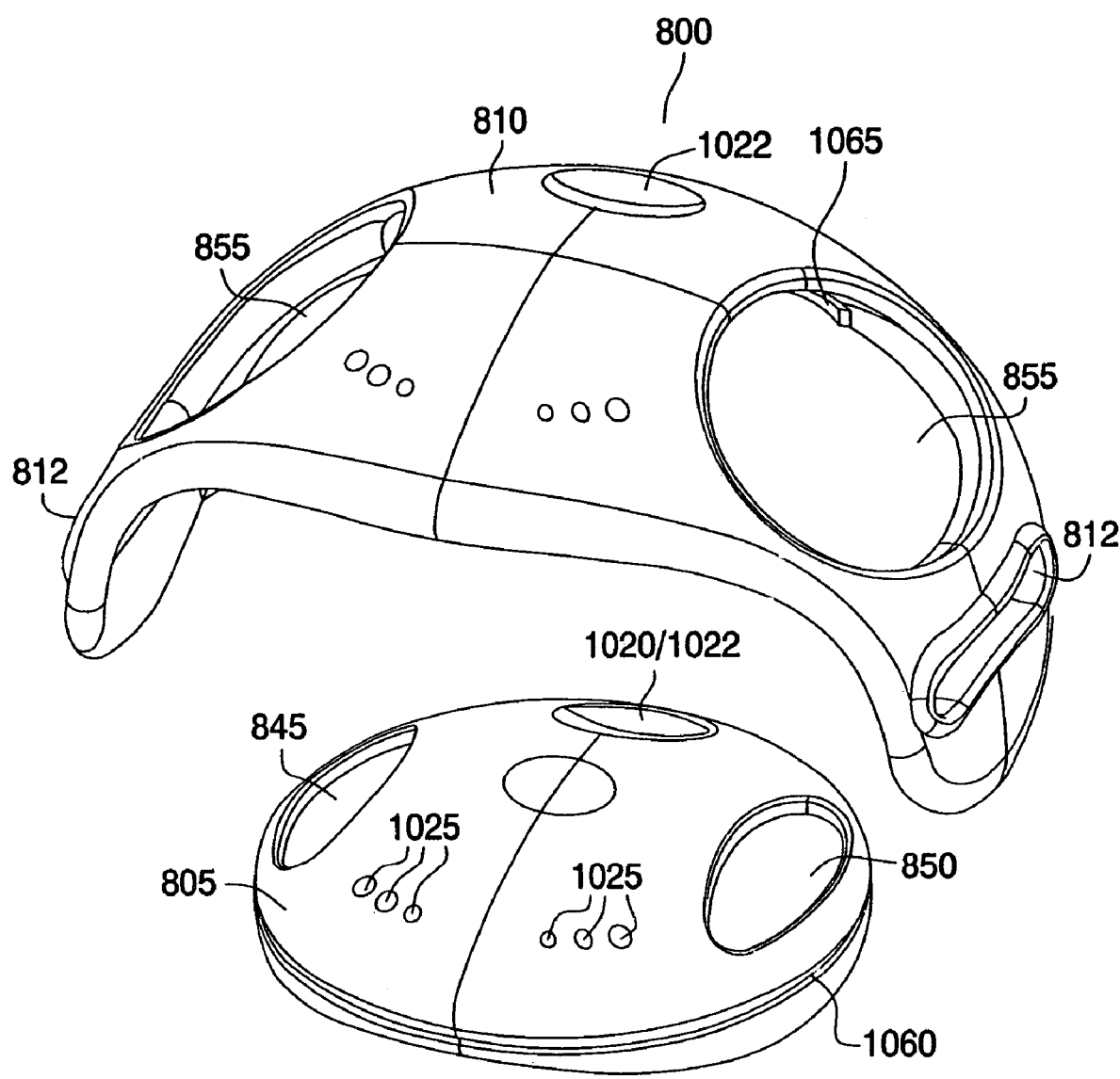
FIGS. 30 and 31 are isometric views of an alternate embodiment of a sensor device according to the present invention having a housing adapted to be removably attached to a flexible section.
Figure 31:
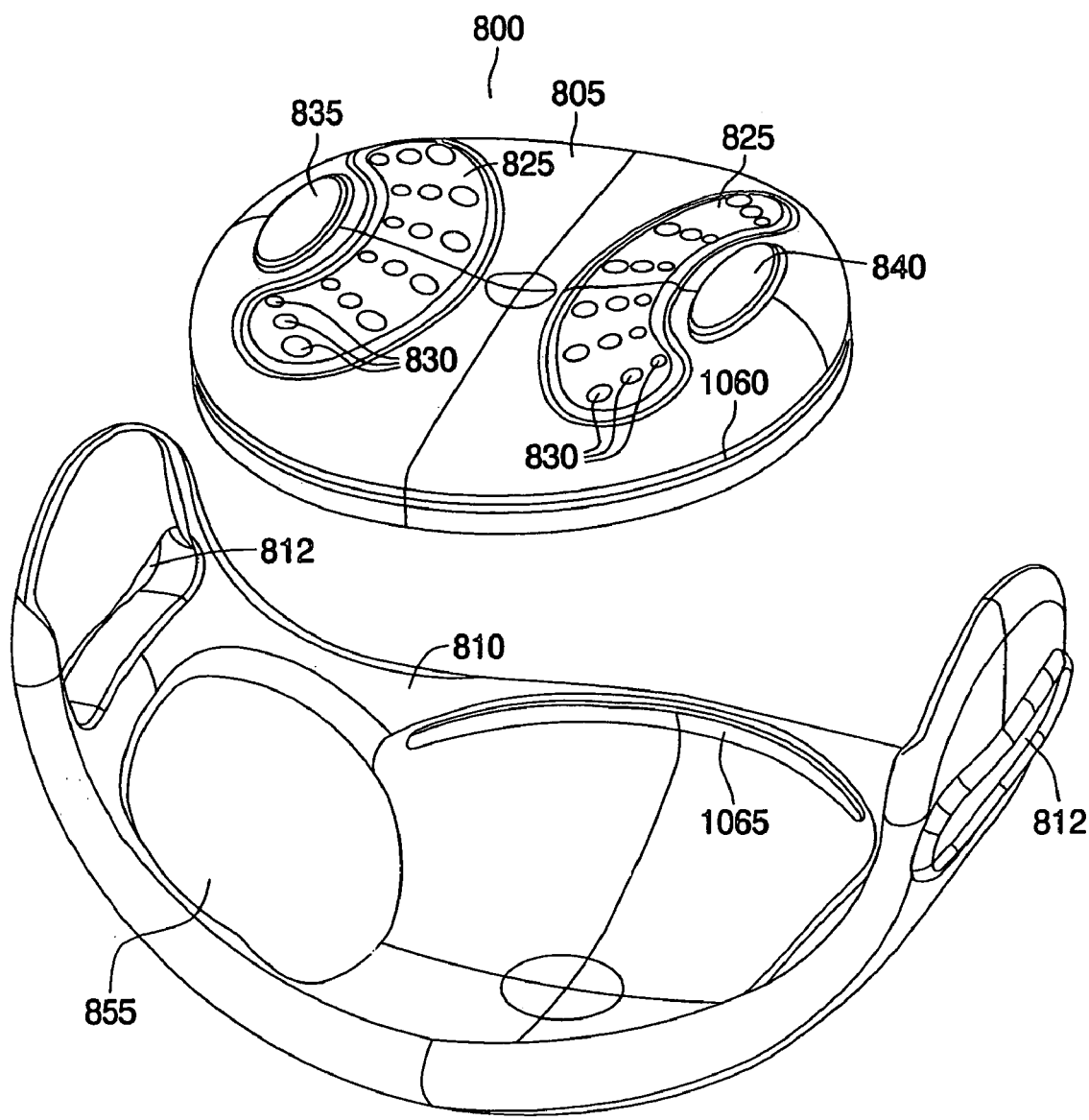
Figure 32:
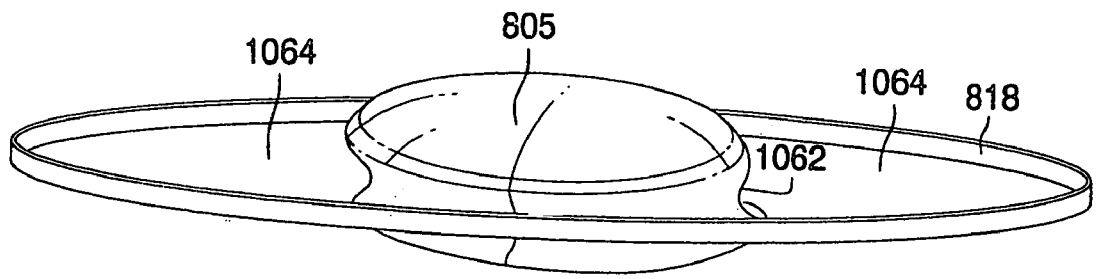
FIG. 32 is an isometric view of a further alternate embodiment of a sensor device according to the present invention having a housing adapted to be removably attached to a flexible section.

In the embodiments shown in FIGS. 30-32, a similar membrane 1022 may be provided on flexible section 810, and, preferably, also on housing 805 such that button 1020 is sealed when housing 805 is removed from flexible section 810. Alternatively, a hole may be provided in flexible section 810 exposing button 1020 and membrane 1022 when housing 805 is attached to flexible section 810. In addition, coupled to processing unit 900 on PCB 860 are LCDs and/or LEDs 1025 for outputting information to the wearer. FIG. 28 shows an alternate embodiment of sensor device 800 in which LCD 1025 is provided on a top face of housing 805. As an alternative to LCDs or LEDs 1025, sensor device 800 may include a prior art electrochemical display that retains its ability to display information even when power is no longer being provided thereto. Such a display is described in U.S. Pat. No. 6,368,287 B1, the disclosure of which is incorporated herein by reference, and includes a plurality of markers comprising a miniature heating element and a coating of heat sensitive material. When current is passed through one of the heating elements, it heats up, thereby inducing a change in the color of the coating material. The color change is permanent, even after the heating element cools down. Such displays are relatively inexpensive and thus are well adapted for use in embodiments of sensor device 800 that are designed to be disposable, possibly single use, items.

Oscillator 1030 is provided on PCB 860 and supplies the system clock to processing unit 900. Reset circuit 1035 is coupled to processing unit 900 and enables processing unit to be reset to a standard initial setting.

Finally, non-volatile data storage device 1040, such as a FLASH memory chip, is provided for storing information collected and/or generated by sensor device 800. Preferably, data storage device 1040 includes at least 128 K of memory. Non-volatile program storage device 1045, such as a FLASH ROM chip, is provided for storing the programs required to operate sensor device 800.

As an alternative, a microprocessor with integral A/D converters, data storage, and program storage may be substituted for processing unit 900, A/D converter 915, data storage device 1040 and non-volatile memory 1045. A suitable example of such a microprocessor is the Texas Instruments Model MSP430 processor.

Any component forming a part of sensor device 800 that comes in contact with the wearer's skin should not, in a preferred embodiment, degrade in durometer, elasticity, color or other physical or chemical properties when exposed to skin oils, perspiration, deodorant, suntan oils or lotions, skin moisturizers, perfume or isopropyl alcohol. In addition, such components preferably are hypoallergenic.

Figure 29:
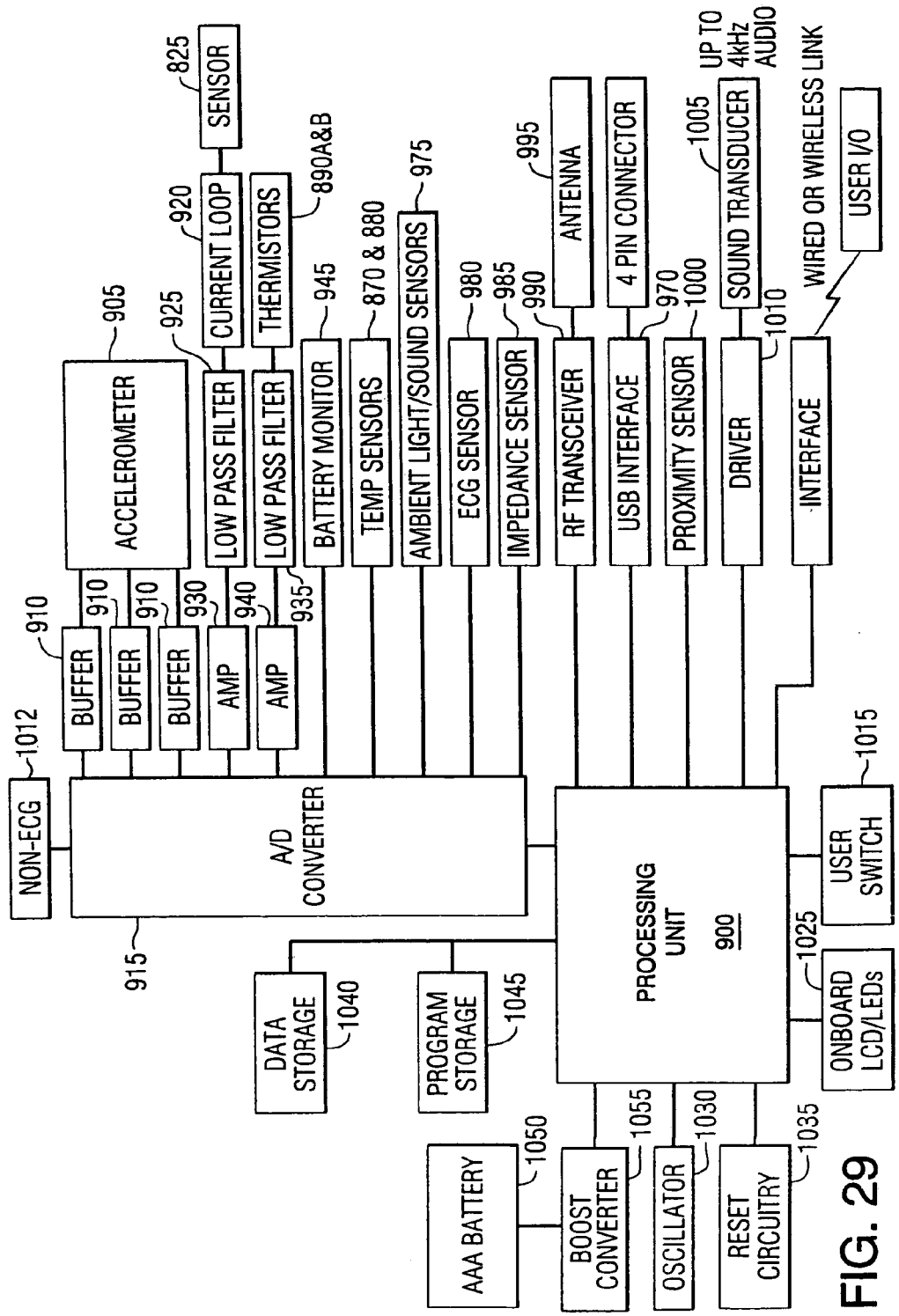
FIG. 29 is a block diagram illustrating the components mounted on or coupled to the printed circuit board forming a part of an alternate embodiment of the sensor device shown in FIGS. 22 through 26.

FIG. 29 shows an alternate embodiment of PCB 860 in which rechargeable battery 950, voltage regulator 955, recharger 960 and USB cable 965 have been replaced by disposable AAA battery 1050 and boost converter 1055. Boost converter 1055 uses an inductor to boost the voltage of AAA battery 1050 to the 3.0-3.3 V required to run the electronics on PCB 860. A suitable boost converter 1055 is the model MAX1724 sold by Maxim Integrated Products, Inc. of Sunnydale, Calif.

Referring to FIGS. 30 and 31, an alternate embodiment of sensor device 800 is shown in which housing 805 is removably attached to flexible section 810. As shown in FIGS. 30 and 31, housing 805 is provided with groove 1060 along with outer edge thereof which is adapted to receive therein tongue 1065 provided on the bottom side of flexible section 810 for securely but removably attaching housing 805 to flexible section 810. Through the interaction of groove 1060 and tongue 1065, housing 805 may thus be readily popped in and out of flexible section 810. Such a configuration enables housing 805 to be readily attached to multiple flexible sections having sizes and shapes that are different than flexible section 810 as long as the flexible section includes a tongue similar to tongue 1065. Such alternate flexible sections may be sized and shaped to fit on particular parts of the body, such as the calf or thigh, and may comprise a garment such as a shirt having the tongue or tongues located in places of interest, such as the upper arm or upper left chest, the latter enabling housing 805 to be positioned over the heart of the wearer. Co-pending U.S. application Ser. No. 09/419,600, owned by the assignee of the present application and incorporated herein by reference, identifies several locations on the body that are particularly well adapted to receive particularly sized and shaped sensor devices so as to avoid interference with the motion and flexibility of the body. As will be appreciated by those of skill in the art, groove 1060 and tongue 1065 may be swapped such that groove 1060 is provided in flexible section 810 and tongue 1065 is provided on housing 805. As will also be appreciated by those of skill in the art, multiple alternative structures exist for securely but removably attaching housing 805 to flexible section 810. These alternative structures include, without limitation, temporary adhesives, screws, a tight fit between having 805 and flexible section 810 that holds the two together by friction, magnets provided in each of housing 805 and flexible section 810, well-known snaps and snapping mechanisms, a threaded portion provided on housing 805 adapted to be received by threads in flexible section 810, an O-ring or similar elastic band adapted to fit around a portion of flexible section 810 and into a groove provided in housing 805 when flexible section 810 is placed over housing 805, or merely pressure when housing 805 is placed on the body and flexible section 810 is placed thereover and attached to the body such as by strap 811. Referring to FIG. 32, a still further alternative structure for removably securing flexible section 810 to housing 805 is shown in which flexible section 810 comprises and elastic or similar band that is adapted to fit into a groove 1062 provided in housing 805. Housing 805 and flexible section 810 may then be placed on the body and held in place by strap 811 or the like inserted through gaps 1064 between housing 805 and flexible section 810.

Figure 33:
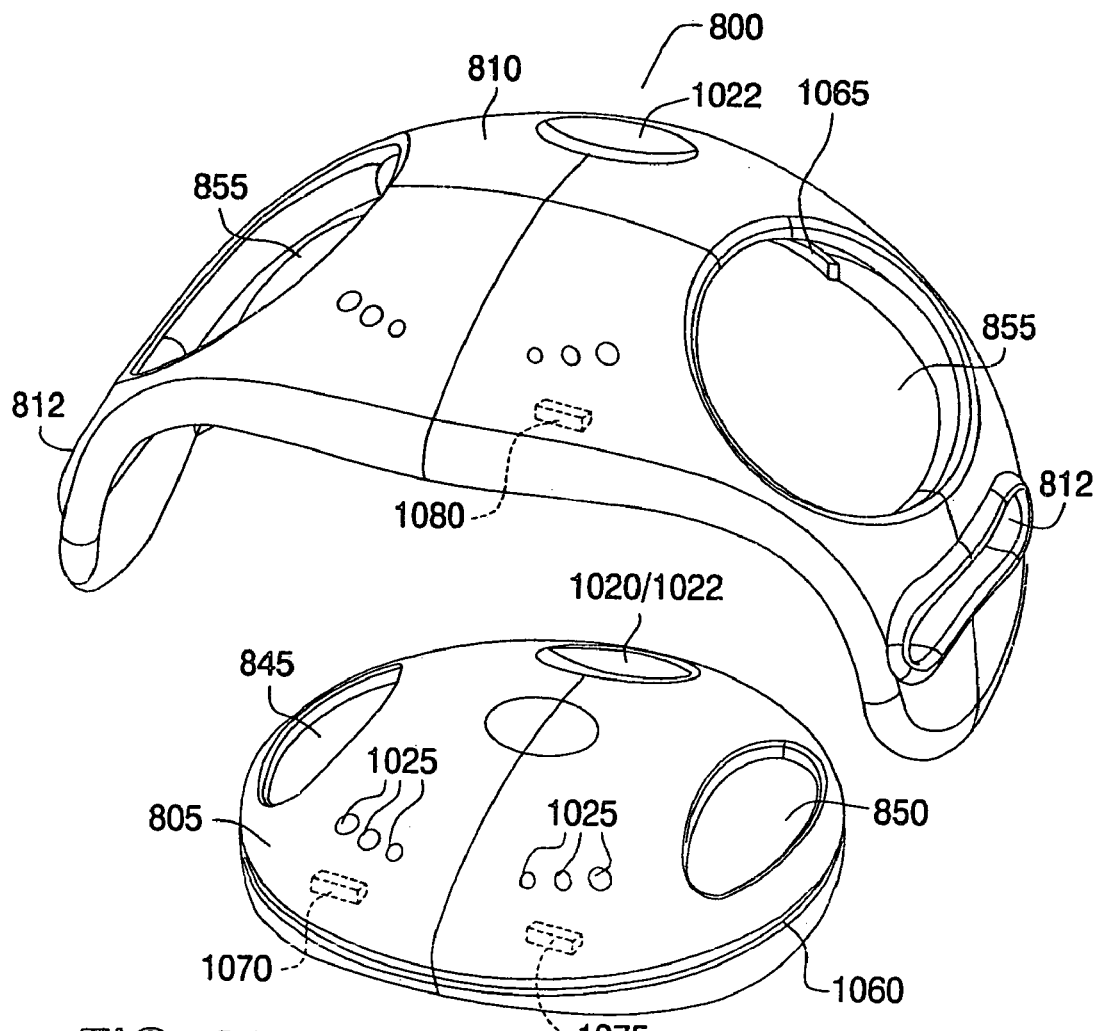
FIG. 33 is an isometric view of an embodiment of a sensor device having adjustable operating parameters according to an aspect of the present invention.

FIG. 33 shows an alternate embodiment of sensor device 800 as shown in FIGS. 30 and 31 that is adapted to automatically adjust or alter the operating parameters of sensor device 800, such as its functionality, settings or capabilities, depending on the particular flexible section to which housing 805 is attached. For example, the calculation of a parameter, such as energy expenditure, may depend on information that is particular each individual, such as age, height, weight, and sex. Rather than having each individual enter that information in sensor device 800 each time he or she wants to wear the device, each individual that is going to wear the device could enter the information once and have their own flexible section that causes sensor device to make measurements based on his or her particular information. Alternatively, the memory in sensor device 800 for storage of user data may be divided into several compartments, one for each user, so as to avoid co-mingling of user data. Sensor device 800 may be adapted to alter where collected data is stored depending on the particular flexible section that is being used. In addition, sensor device 800 may be calibrated and recalibrated differently over time depending on the particular flexible section to which housing 805 is attached as it learns about each particular wearer and his or her habits, demographics and/or activities.

According to a particular embodiment, housing 805 is provided with first magnetic switch 1070 and second magnetic switch 1075, each on PCB 860. Provided on or inside flexible section 810, such as by an insert molding technique, is magnet 1080. Magnet 1080 is positioned on or inside flexible section 810 such that it aligns with and thereby activates one of first magnetic switch 1080 and second magnetic switch 1075 when housing 805 is attached to flexible section 810. In the embodiment shown in FIG. 33, second magnetic switch 1075 will be activated. A second flexible section 810 similar to flexible section 810 shown in FIG. 33 will also be provided, the difference being that the magnet 1080 provided therewith will be positioned such that first magnetic switch 1070 is activated when housing 805, the same housing 805 shown in FIG. 33, is attached to the second flexible section 810. Housing 805, and in particular processing unit 900, may be programmed to alter its functionality, settings or capabilities depending on which one of first magnetic switch 1070 and second magnetic switch 1075 is activated, i.e., which particular flexible section 810 is being used. Thus, a husband and wife may share a single housing 805 but have different flexible wings 810 with magnets 1080 located in different places. In such a case, housing 805 may be programmed to operate with functionality, settings or capabilities particular to the husband when first magnetic switch 1070 is activated, and with functionality, settings or capabilities particular to the wife when second magnetic switch 1075 is activated. Although only two magnetic switches are shown in FIG. 33, it will be appreciated that multiple magnetic switches and multiple flexible sections may be used to allow sensor device 800 to be programmed for multiple wearers, such as an entire family, with each family member having his or her own flexible section. As still a further alternative, multiple flexible sections may be provided that are adapted to be worn on different parts of the body, each having a magnet placed in a different location. Housing 805 may then be programmed to have functionality, settings or capabilities particular to the type of sensing to be done on each different part of the body, with magnetic switches placed so as to be activated when housing 805 is attached to the appropriate flexible section. Sensor device 800 according to this embodiment is thus a "smart" device. As will be appreciated by one of skill in the art, many alternatives to first and second magnetic switches 1070 and 1075 and magnet 1080 may be used to provide the functionality described in connection with FIG. 33. Such alternatives include, without limitation, mechanical switches provided in housing 805 that are activated by a protruding portion, such as a pin, provided at a particular location on flexible section 810, optical switches comprising an array of light sensors provided in housing 805 that are activated when the surrounding light is blocked, reflected or filtered in a particular way with one or more translucent sections and a single opaque, reflective or filtering section being selectively provided on flexible section 810 at particular locations, the translucent sections not activating the corresponding optical switches and the opaque, reflective or filtering section activating the corresponding optical switch, electronic switches provided in housing 805 activated by a conductor provided in particular locations in flexible section 810. As still a further alternative, housing 805 may be provided with multiple switches and each flexible section 810 may be provided with one or more switch activators positioned to activate certain selected switches. The operating parameters of housing 805 would in this embodiment be adapted to change depending upon the particular set of one or more switches that are activated. This embodiment thus employs an encoding scheme to alter the operating parameters of housing 805 depending on which flexible section 810 is used. As still a further alternative, housing 805 may be provided with a single switch adapted to alter the operating parameters of housing 805 depending upon the way in which or state in which it is activated, such as by the properties of the switch activators. For example, the switch may be a magnetic switch that is activated a plurality of different ways depending upon the magnetic level or strength of the magnet provided in each flexible section 810. A plurality of flexible sections 810 could then be provided, each having a magnet of a different strength. In addition, any particular flexible section 810 may be provided with a plurality of magnets having different strengths with each magnet being able to activate the switch in housing 805 in a different manner. Such a flexible section 810 would be able to selectively trigger different operating parameters of housing 805, such as by rotating a portion of flexible wing 805 to align a particular magnet with the switch. As an alternative, the switch could be an electrical switch and the switch activators could be conductors having different resistances. The switch would, in this embodiment, be activated in different ways depending on the measured resistance of the switch activator that closes the circuit.

Figure 34:
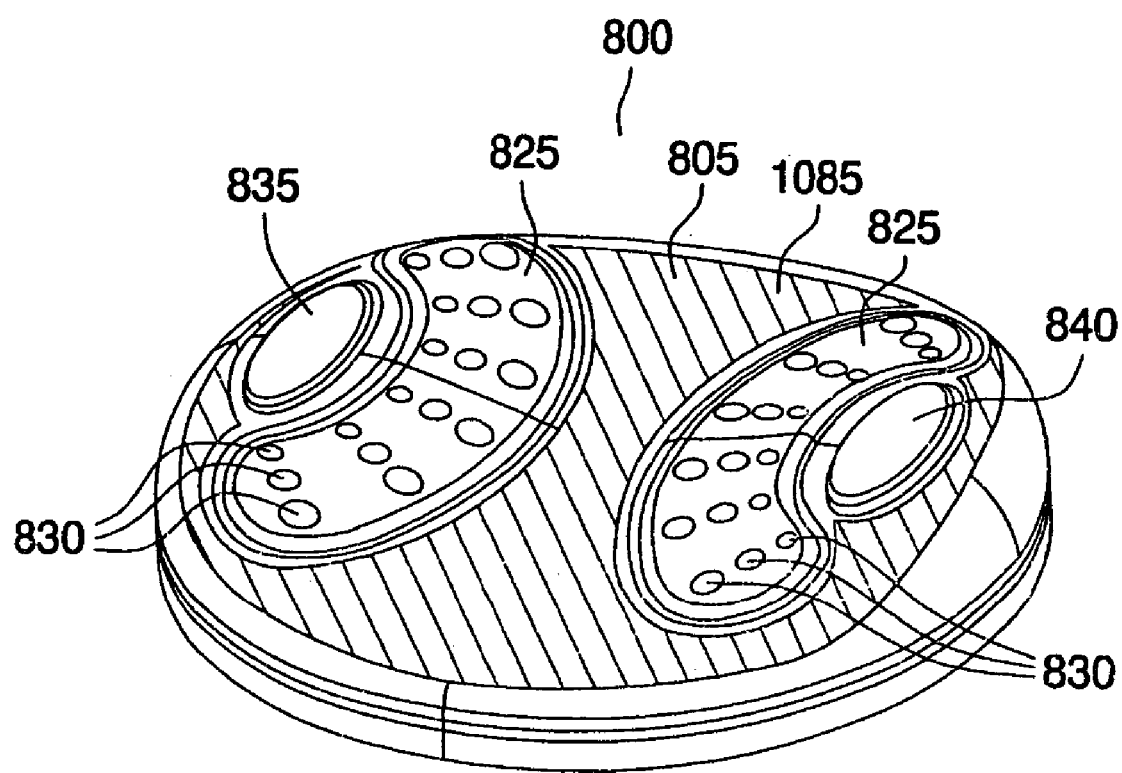
FIG. 34 is an isometric view of an alternate embodiment of a sensor device according to the present invention having a housing having an adhesive material on an external surface thereof for removably attaching the housing to the body.

Referring to FIG. 34, as still a further embodiment of sensor device 800, housing 805 may be provided with adhesive material 1085 on a back side thereof to enable housing 805 to be removably attached to selected portions of the body, such as the upper left chest over the heart, without flexible section 810. Adhesive material 1085 may be any well-known adhesive that would securely attach housing 805 to the body and enable it to be worn for a period of time, but that would also readily enable housing 805 to be removed from the body after use. Adhesive material 1085 may comprise, for example, a double sided adhesive foam backing that would allow for comfortable attachment of housing 805 to the body. Furthermore, housing 805 may be made of a well-known flexible plastic film or the like, such as that taught in U.S. Pat. No. 6,368,287 B1, the disclosure of which is incorporated herein by reference, that would, due to low cost, enable sensor device 800 to be disposable. Such a disposable sensor device may also include an electrochemical display described above to enhance its disposability. In an embodiment adapted for placement over the upper left chest or any other appropriate region for detecting heart related parameters, sensor device 800 would include one or more sensors described herein for sensing heart related parameters such as heart rate, beat-to-beat or interbeat variability, ECG or EKG, pulse oximetry, heart sounds, such as detected with a microphone, and mechanical action of the heart, such as detected with ultrasound or micro-pulse radar devices.

Figure 35A:
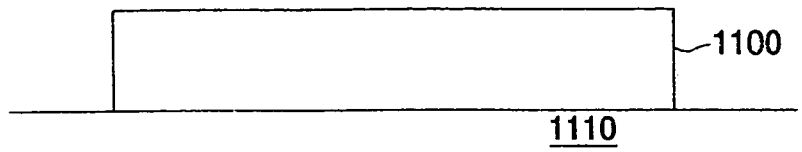
FIGS. 35A and B are cross-sectional views of a housing for a prior art sensor device.
Figure 35B:
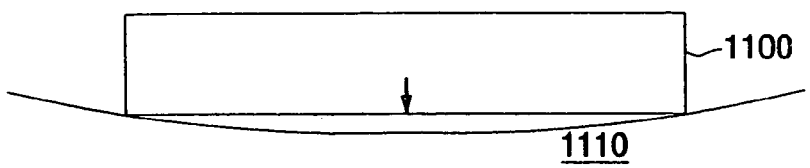
FIGS. 35C through H are cross-sectional views of various embodiments of a housing for a sensor device according to an aspect of the present invention taken along lines C-C in FIG. 23.

FIGS. 35A-H and 36A-H illustrate aspects of the present invention relating to the ergonomic design of sensor device 800. Referring to FIGS. 35A and 35B, a housing 1100 of a prior art sensor device having a rectangular cross-section is shown resting on the body 1110 of a wearer of the prior art sensor device. As seen in FIG. 35B, when body 1110 flexes and forms a concavity, as may happen many times each minute on various parts of the body or for extended periods of time depending on the position of various body parties during particular activities, a significant portion of housing 1100 is caused to be removed from body 1110. When housing 1100 is caused to be removed in this manner, the ability of the prior art sensor device to accurately make measurements and collect data will be jeopardized, especially for any readings to be taken near the center of the cross-section indicated by the arrows in FIG. 35B.

Figure 35C:
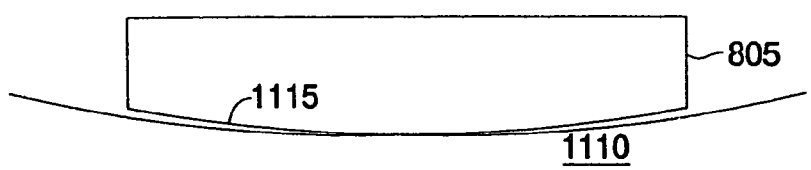
Figure 35D:
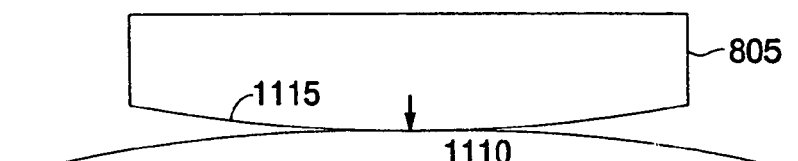
Figure 35E:
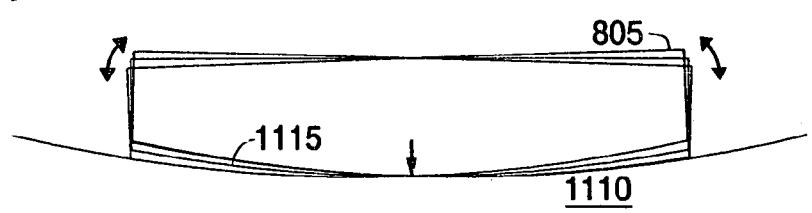
Figure 35F:
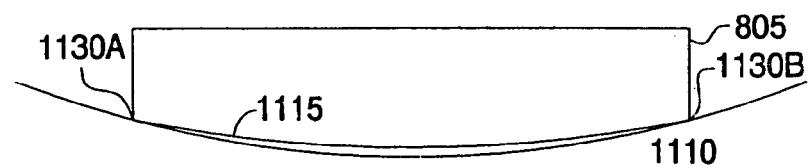
Figure 35G:
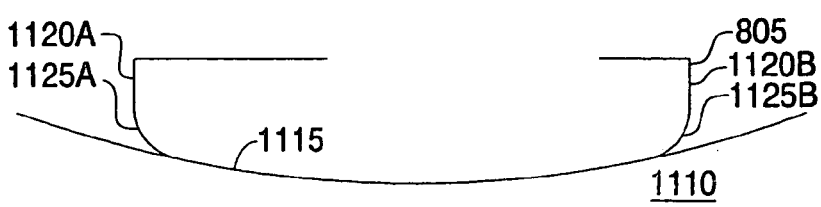
Figure 35H:
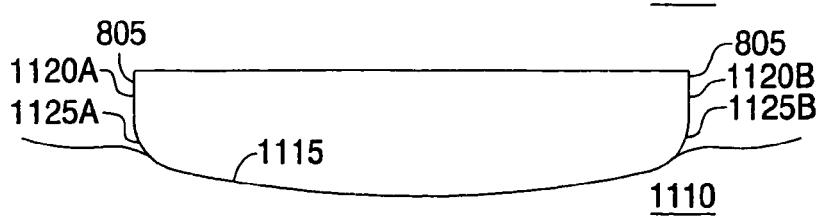

FIGS. 35C-H illustrate a cross-section of housing 805 of sensor device 800 taken along lines C-C shown in FIG. 23 according to various aspects of the present invention. The cross-section shown in FIGS. 35C-H is taken near the middle portion of housing 805 shown in FIG. 23 between GSR sensors 825. As seen in FIG. 35C, bottom surface 1115 of housing 805 is provided with a generally convex shape such that, when body 1110 flexes and forms a concavity, a substantial portion of bottom surface 1115 of housing 805 remains in contact with body 1110 by fitting into the concavity. As seen in FIG. 35D, when body 1110 flexes in the opposite direction so as to create a convexity, the center portion of housing 805, indicated by the arrow in FIG. 35D, remains in contact with body 1110. As shown in FIG. 35E, this is true even if housing 805 were to rock within the concavity formed in body 1110. Referring to FIG. 35F, body 1110 may, at times, flex to an extreme degree, i.e., more than the anticipated maximum that it was designed for, such that, even if bottom surface 1115 is provided with a convex shape, it may still cause bottom surface 1115 to be removed from body 1110. A solution to this problem is illustrated in FIG. 35G, wherein the lateral ends 1120A and 1120B of housing 805 are provided with radiused portions 1125A and 1125B, respectively adjacent to and including opposite lateral ends of bottom surface 1115. Radiused portions 1125A and 1125B enable housing 805 to sit lower and fit into the concavity created when body 1110 flexes to an extreme degree. In addition, radiused portions 1125A and 1125B provide for more comfortable wear as they eliminate sharp edges 1130A and 1130B shown in FIG. 35F that contact body 1110. FIG. 35H shows how body 1110 will tend to conform to the shape of housing 805 due at least in part to the viscosity of the skin when body 1110 is in a relaxed condition.

FIG. 36A shows a cross-section of housing 1100 of prior art sensor device taken along a line perpendicular to the line on which the cross-section shown in FIGS. 35A and 35B was taken. As seen in FIG. 36A, when housing 1100 is placed on a convex portion of body 1110, significant portions of housing 1100, specifically the lateral ends thereof indicated by the arrows in FIG. 36A, are not in contact body 1110. FIGS. 36B-H show a cross-section of housing 805 according to various aspects of the present invention taken along lines D-D shown in FIG. 23. As seen in FIG. 36B, bottom surface 1115 of housing 805 is provided with a generally concave shape adapted to receive the convex portion of body 1110. Referring to FIG. 36C, lateral ends 1130A and 11301 maybe provided with radiused portions 1135A and 1135B adjacent to and including opposite lateral ends of bottom surface 1115, which allow housing 805 to rest in closer contact with body 1110, even when body 1110 flexes to an extreme degree, i.e., more than the anticipated maximum that it was designed for, and remove sharp edges 1140A and 1140B shown in FIG. 36B, providing for more comfortable wear. As shown in FIG. 36D, body 1110 will tend to conform to the shape of housing 805 when body 1110 is in a relaxed condition. As shown in FIGS. 36E and 36F, good contact with body 1110 is maintained at the points illustrated by the arrows when body 1110 is flexed in a manner that decreases the convex shape thereof or that creates a convexity therein. Thus, it will be appreciated that it is advantageous to place sensors or sensing elements at the points indicated by the arrows because those points will tend to remain in contact with body 1110. FIGS. 36G and 36H, showing, for example, heat flux skin interface component 835 and skin temperature skin interface component 840 placed at the points indicated by the arrows, illustrate this point. As seen in FIGS. 36G and 36H, there is more than point contact between body 1110 and skin temperature skin interface component 840.

Figure 37:
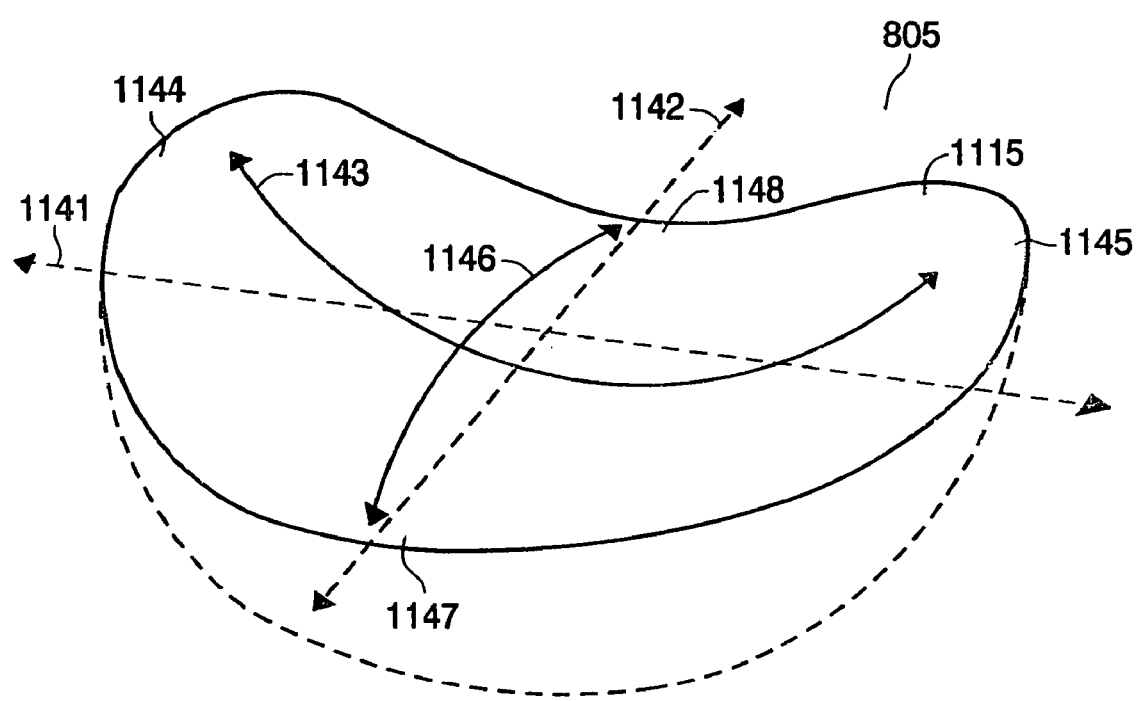
FIG. 37 is an isometric view of an embodiment of a housing for a sensor device according to the present invention having a bottom or inner surface having a concavity in one direction and a convexity in another direction.
Figure 38A:
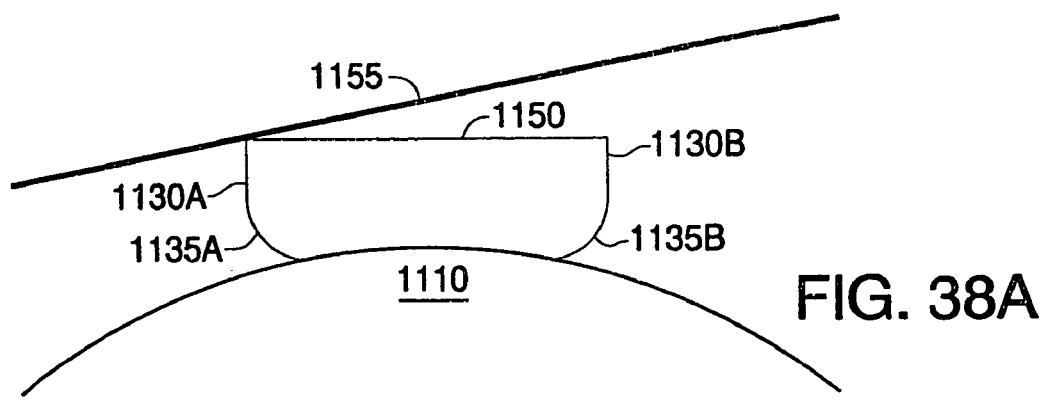
FIGS. 38A through D are cross-sectional views of a housing for a sensor device having a flat top surface and flat lateral ends.
Figure 38B:
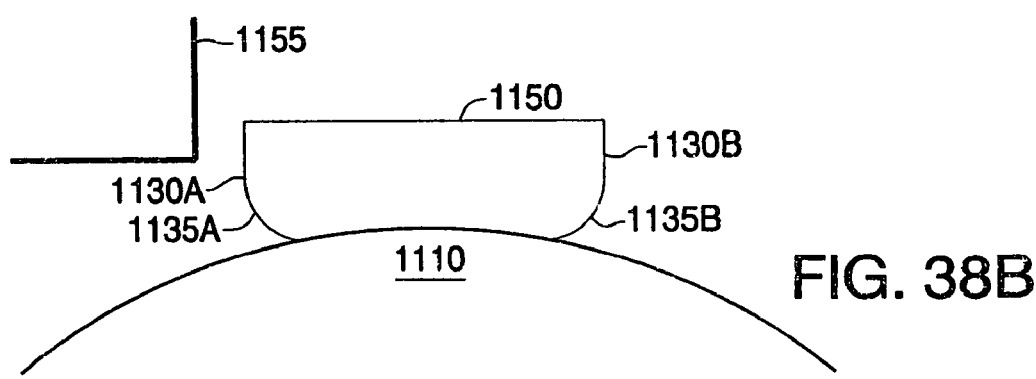
Figure 38C:
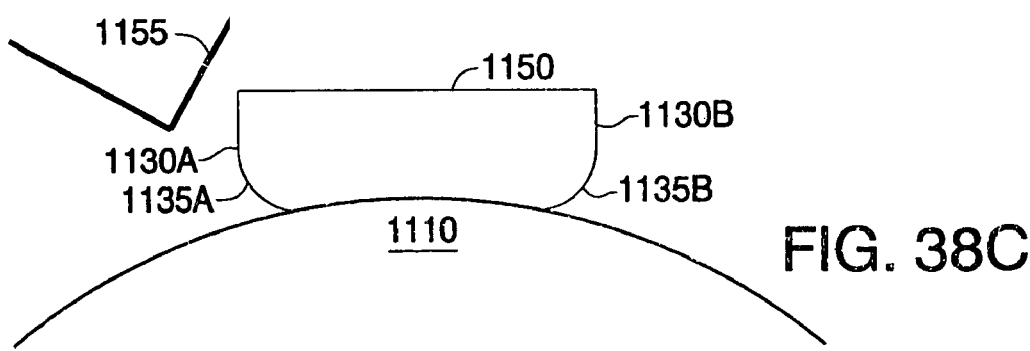
Figure 38D:
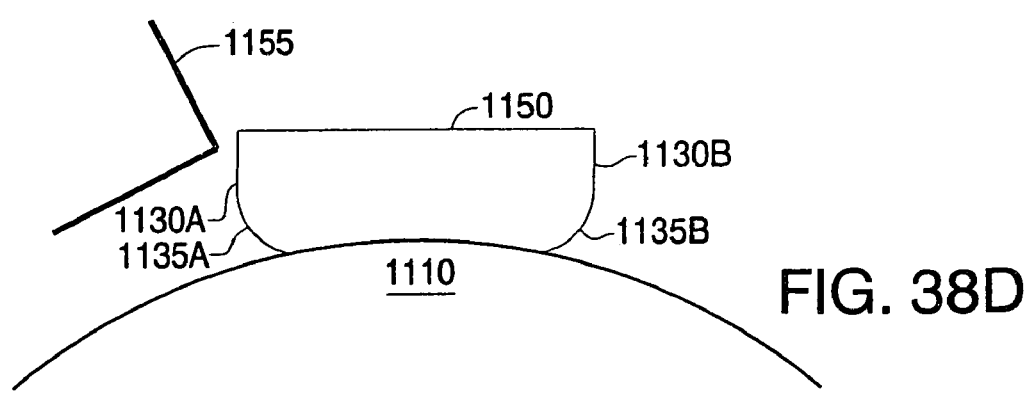

FIG. 37 is an isometric view of housing 805 according to an embodiment of the present invention in which bottom surface 1115 has both the generally convex shape shown in FIGS. 35C-H and the generally concave shape shown in FIGS. 36B-H. Specifically, bottom surface 1115, which is the inner surface of housing 805 for mounting adjacent to the body of the wearer, includes a longitudinal axis 1141 and a transverse axis 1142. Bottom surface 115 has a generally concave shape having an axis of concavity 1143 that is coincident with longitudinal axis 1141, meaning that it runs in a first direction from first lateral end 1144 of inner surface 1115 to second lateral end 1145 of inner surface 1115. Bottom surface 1115 has a generally convex shape having an axis of convexity 1146 that is coincident with transverse axis 1142, meaning that it runs in a second direction from third lateral end 1147 of inner surface 1115 to fourth lateral end 1148 of inner surface 1115. As seen if FIG. 37, the first and second directions, and longitudinal axis 1141 and transverse axis 1142, are generally perpendicular to one another.

Figure 39A:
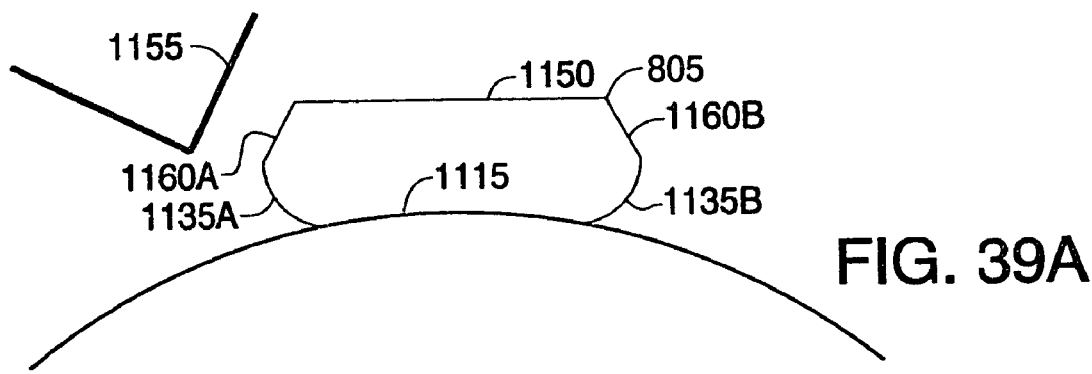
FIGS. 39A through F are cross-sectional views of various embodiments of a housing for a sensor device having surfaces designed to deflect objects and prevent movement of the housing.
Figure 39B:
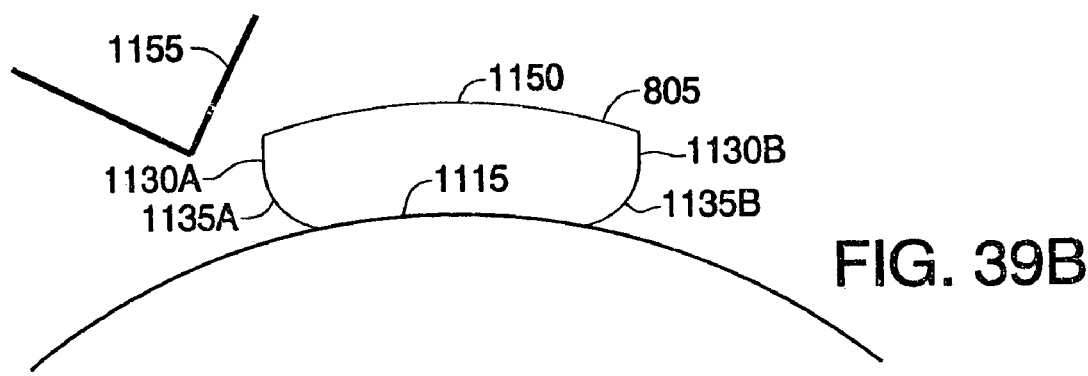
Figure 39C:
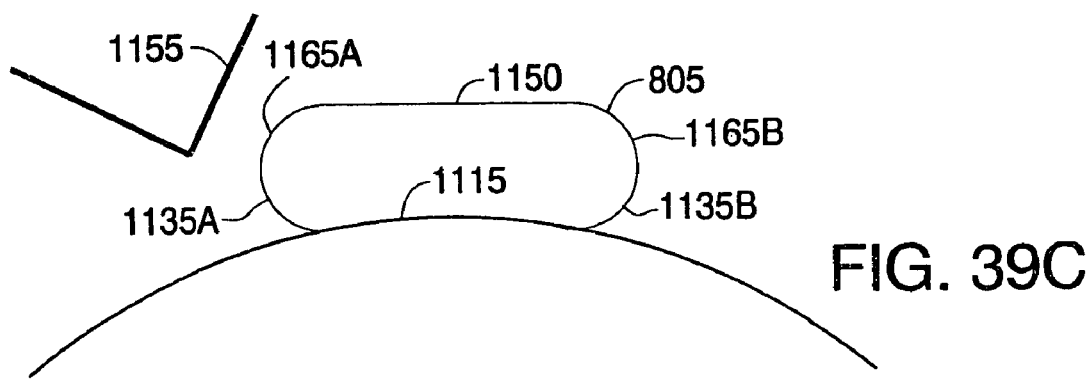
Figure 39D:
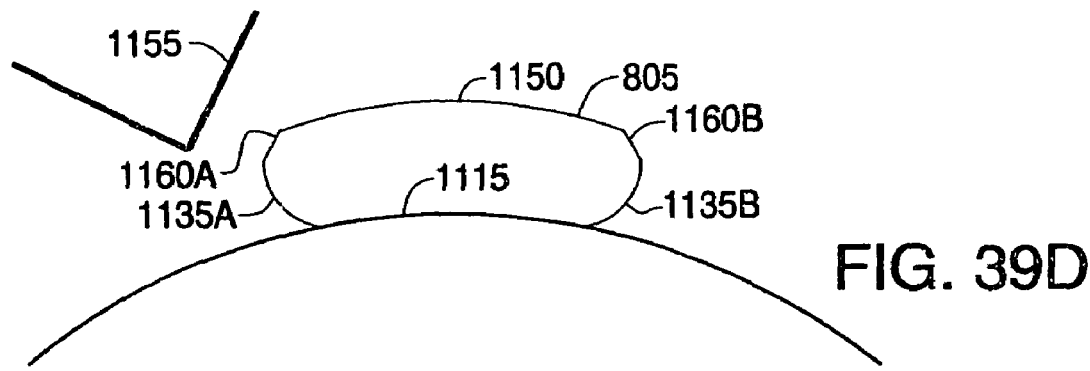
Figure 39E:
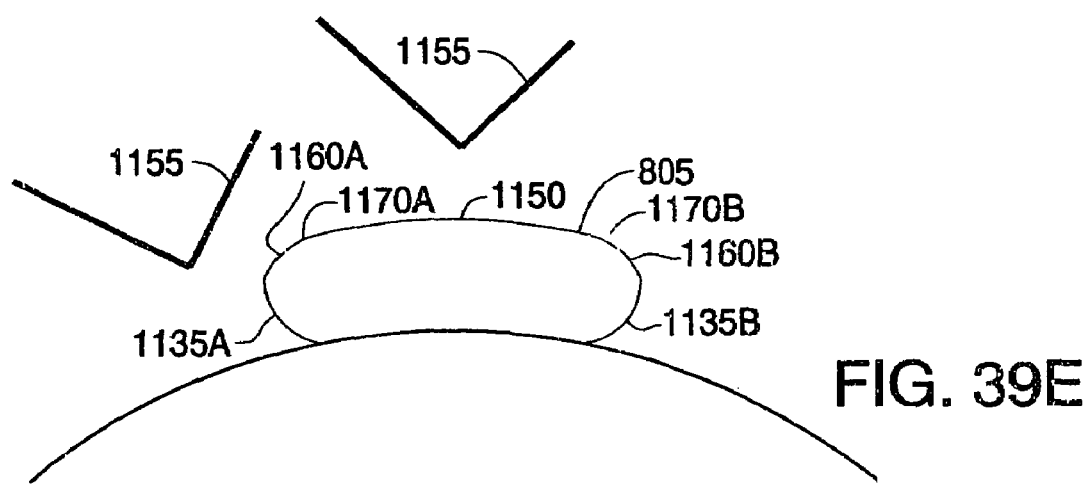
Figure 39F:
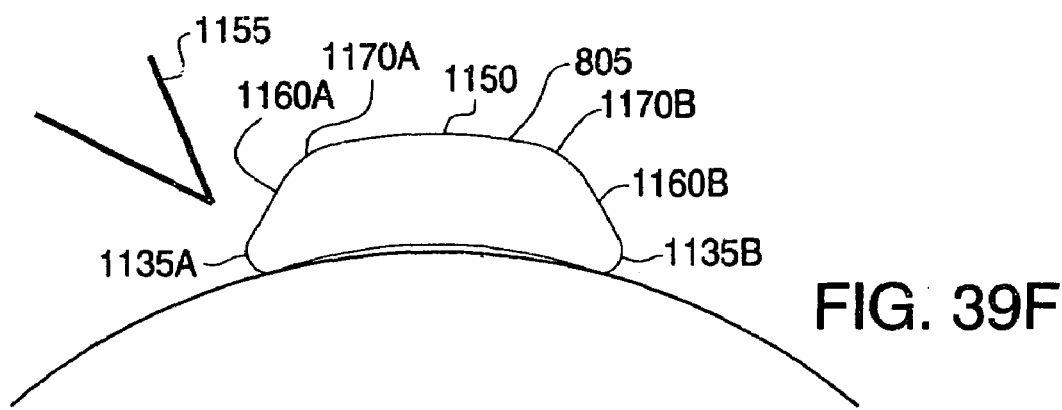
Figure 39G:
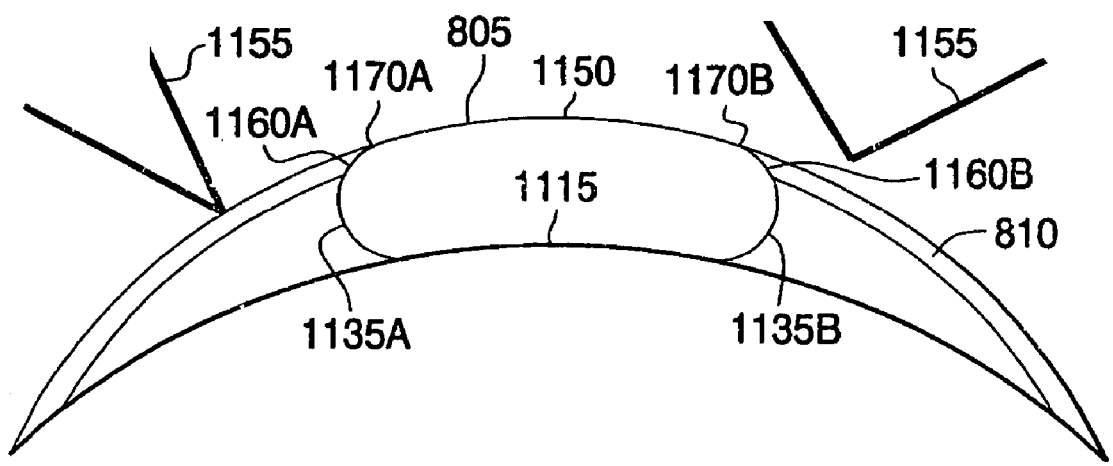
FIG. 39G is a cross-sectional view of the housing shown in FIG. 39E attached to a flexible section.

Referring to FIGS. 38A-D, it will be appreciated that housing 805 having a flat top surface 1150 and flat lateral ends 1130A and 1130B may tend to be jostled and bumped by object 1155, such as a wall or door or the corner or edge of a drawer, cabinet or desk, thereby moving housing 805 on body 1110 because such flat surfaces are not well adapted to deflect object 1155. Movement of housing 805 on body 1110 will detrimentally effect the ability of sensor device 800 to accurately make measurements and collect data. FIGS. 39A-G illustrate various aspects of the present invention that are adapted to deflect object 1155 and substantially prevent movement of housing 805 on body 1110. In addition, the forms shown in FIGS. 39A-G increase the durability of sensor device 800 and make it easier to put on and wear clothing and the like, such as a wetsuit, over sensor device 800. As seen in FIG. 39A, housing 805 may have tapered sides 1160A and 1160B such that the width of housing 805 decreases in the direction from bottom surface 1115 to top surface 1150. Alternatively, referring to FIG. 39B, top surface 1150 of housing 805 may have a convex shape. As a further alternative, as seen in FIG. 39C, housing 805 may be provided with radiused portions 1165A and 1165B that meet with radiused portions 1135A and 1135B such that the lateral ends of housing 805 have a substantially semicircular shape. As shown in FIG. 39D, housing 805 may have both tapered sides 1160A and 1160B and a top surface 1150 with a convex shape. FIG. 39E is a modification of housing 805 shown in FIG. 39E in which the points 1170A and 1170B where radiused portions 1135A and 11351B meet tapered sides 1160A and 1160B, respectively, are themselves radiused. FIG. 39F is a variation of housing 805 shown in FIG. 39E having elongated tapered sides 1160A and 1160B. FIG. 39G shows how the ability of housing 805, such as the embodiment shown in FIG. 39E, to deflect object 1155 may be enhanced by the addition of flexible section 810 having a substantially convex outer surface. In addition, an air channel is provided between flexible section 810 and body 1110 to allow for heat to flow away from body 1110.

Figure 40:
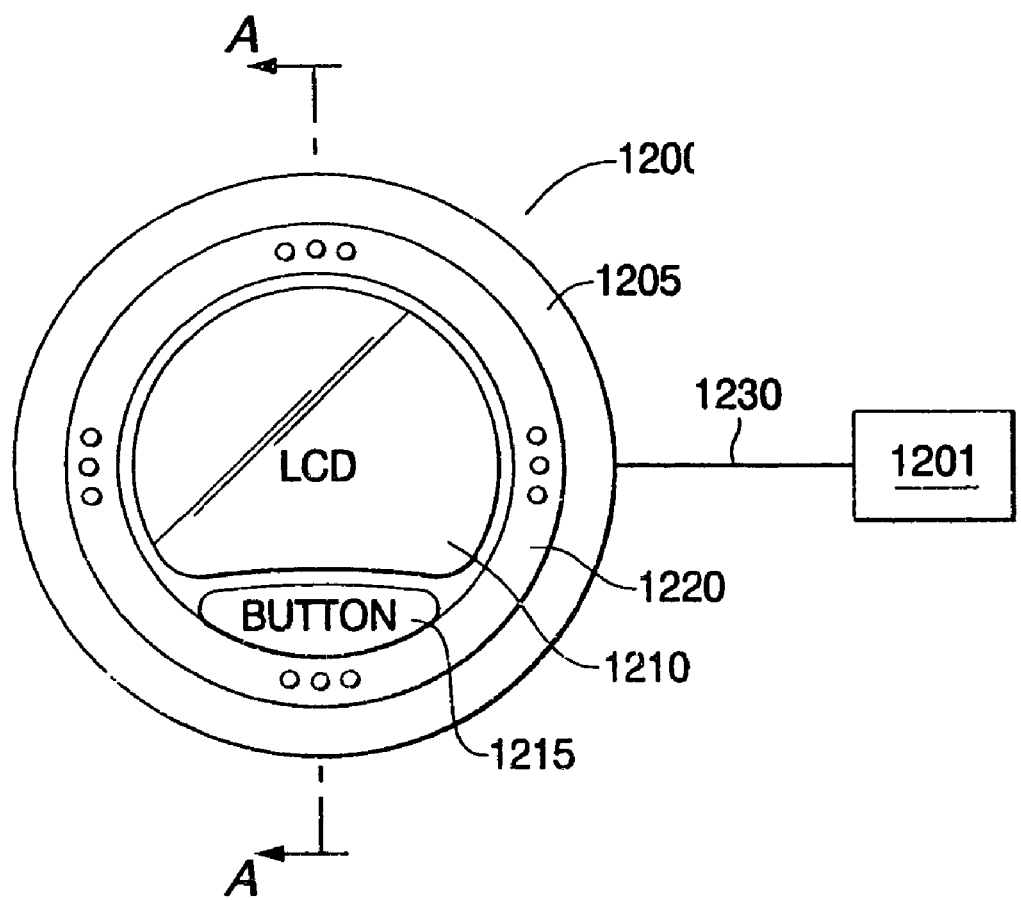
FIG. 40 is a top plan view of a data input and output device according to the present invention.
Figure 41:
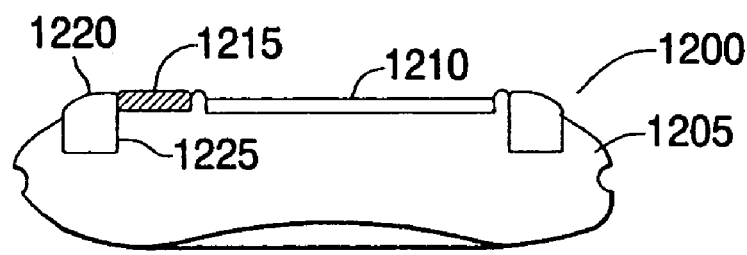
FIG. 41 is a partial cross-sectional view of the data input and output device shown in FIG. 40 taken along lines A-A in FIG. 40.

Referring to FIG. 40, a top plan view of a data input and output, abbreviated I/O, device 1200 is shown. FIG. 41 is a partial cross-sectional view of I/O device 1200 taken along lines A-A in FIG. 40. According to one embodiment of the present invention, I/O device 1200 is in electronic communication with sensor device 1201 shown in FIG. 40 through communications connection 1230, which may comprise a wired connection or a wireless connection as described elsewhere herein. Sensor device 1201 detects human physiological and/or contextual parameters, and may be any one of sensor device 400 shown in FIGS. 12-17, stand alone sensor device 700 shown in FIG. 21, or sensor device 800 shown in FIGS. 22-26. I/O device 1200 includes housing 1205 and LCD 1210 attached to housing 1205. Various alternative display devices may be used instead of an LCD for displaying information, and such displaying of information and display devices are not limited to visual display devices, but may include various tactile or audible displays as described elsewhere herein. LCD 1210 may display information relating to the human physiological and/or contextual parameters detected by sensor device 1201 that is transmitted to I/O device by sensor device 1201 over communications connection 1230. Thus, I/O device 1200 may display the same information and give the same feedback that any of the previously described sensor devices. I/O device 1200 also includes button 1215 and dial 1220. Dial 1220 is moveably mounted within groove 1225 provided in housing 1205 such that dial 1220 is free to rotate about the top surface of housing 1205 in both clockwise and counter-clockwise directions within groove 1225. Button 1215 and dial 1220 maybe used to enter or input information into I/O device 1200 for subsequent storage in and use by I/O device 1200 and/or transmission to sensor device 1201. Thus, LCD 1210 may also display information that is entered or input into I/O device 1200, or information generated from such entered or input information. I/O device 1200 may take on any number of forms, including, but not limited to, a watch-like form adapted to be worn on the wrist, a form that may be clipped to or integrated within a bag or clothing, or otherwise easily carried in a pocket or a bag, a form similar to well known commercially available pagers or PDAs, a form that may be removably, such as magnetically, attached to sensor device 1201 or another apparatus such as a car dashboard, or the form of a key fob. I/O device 1200 could also be a separate electronic device such as a weight scale, in which case the weight scale may comprise a sensor that communicates information to sensor device 1201.

It will be appreciated that, in the embodiment where sensor device 1201 is stand alone sensor device 700, I/O device 1200 may perform the manual data entry functions indicated by and described in connection with reference numeral 715 in FIG. 21. Furthermore, in this embodiment, I/O device 1200 may be the computing device 750 shown in FIG. 21. As described in connection with FIG. 21, this configuration provides several possibilities for data collection, generation and display. Specifically, sensor device 1201, as described in connection with stand alone sensor device 700 shown in FIG. 21 and the subject of co-pending application Ser. No. 09/923,181 owned by the assignee hereof, may collect and/or generate data indicative of various physiological and/or contextual parameters of the user, data manually input by the user, such as by using button 1215 and dial 1220, and/or data input as a result of device-to-device interaction shown at 720 and 725 in FIG. 21. Sensor device 1201 may then generate derived data and analytical status data which may be transmitted to I/O device 1200 for display. Alternatively, sensor device 1201 may be programmed to generate derived data, which, along with the data collected by sensor device 1201, may be transmitted to I/O device 1200, and I/O device 1200 may be programmed and/or otherwise adapted to include the utilities and algorithms necessary to create analytical status data based on the data indicative of one or more physiological and/or contextual parameters, the data derived therefrom, the data manually input by the user and/or the data input as a result of device-to-device interaction. The derived data and the analytical status data so created may be displayed to the user with LCD 1210. As still a further alternative, the data indicative of various physiological and/or contextual parameters, the manually input data, and/or the data input as a result of device-to-device interaction may be transmitted to I/O device 1200, and I/O device 1200 may be programmed and/or otherwise adapted to include the utilities and algorithms necessary to create derived data and/or analytical status data from the foregoing sources of data, all of which may then be displayed to the user with LCD 1210. I/O device 1200 may also use the information input into it, such as by using button 1215 and dial 1220, to create derived data and/or analytical status data, or may use data sensed by a sensor provided on I/O device 1200 as described elsewhere herein for the same purpose. In addition, the generation of such data may be shared with or offloaded to a separate computing device in electronic communication with I/O device 1200, such as a local PC or a remote server. In each of the foregoing embodiments, I/O device may be in electronic communication with and transmit data to still another device, such as a computing device or an earpiece or tactile communications device worn by a firefighter or other first responder or a runner. In this case, I/O device 1200 acts as a relay of information. In the case of the firefighter or other first responder, the data may indicate an important physiological state, such as level of hydration, as determined by sensor device 1201, and in the case of a runner, the data may indicate caloric expenditure or distance traveled.

As known in the art, a number of configurations exist for constructing I/O device 1200 so that button 1215 and dial 1220 may be used to input information into I/O device 1200. Such buttons and dials are commercially available from Duraswitch Industries, Inc. located in Mesa, Ariz. under the names PUSHGATE™ pushbutton and thiNcoder™ ROTOR, respectively. U.S. Pat. No. 5,666,096, the disclosure of which is incorporated herein by reference, is owned by Duraswitch Industries, Inc. and describes the rotary switch technology used in the thiNcoder™ ROTOR switch. The '096 patent describes a rotary switch including a bottom substrate layer and a top membrane layer separated by a non-conductive spacer. The internal surface of the membrane layer carries a set of electrodes which define the spaced contacts of at least one electrical switch. The membrane layer also carries an electrically conductive metallic armature, in the form of a flat circular disc, that is received in an annular opening provided in the spacer. The switch further includes a rotatable actuating knob that carries a coupler in its underside. The coupler is a magnet which may be molded or otherwise entrapped in the knob. The coupler forces the armature against the internal surface of the membrane by means of the magnetic field originating from the coupler. The coupler functions both to create the switch contact pressure as well as to drag the armature from one contact to another when a user rotates the knob. In operation, when the knob is rotated, the coupler rotates with the knob and, by virtue of the magnetic coupling between the coupler and the armature, the armature rotates with the knob as well. As the armature rotates, it moves into and out of shorting contact with the contact or contacts on the membrane. When the armature is in shorting contact with a contact, the corresponding switch is closed. As will be appreciated by those of skill in the art, various encoding schemes are known for converting the actuation of one or more switches into information that may be used by a processor or other device coupled to the switch.

Alternatively, U.S. Pat. No. 6,225,980 B1, the disclosure of which is incorporated herein by reference, describes a rotary dial input device for portable computers including an insulating member overlying a printed circuit board, a spine rigidly connected to the printed circuit board, a rotatable dial, a switch ring carried by the dial and a snap ring rigidly connected to the dial. The dial, the switch ring and the snap ring rotate together around the periphery of the spine. The switch ring carries at least two magnets located 180° apart, and a plurality of Hall effect sensors are mounted on the printed circuit board and lie just under the surface of the insulating material. The position of the magnets relative to any of the Hall effect sensors may be used to generate an output signal based on the position of the dial. The '980 patent also describes a spring-based mechanism for enabling the dial to be moved between first and second vertical positions, wherein the springs biases the dial toward the first vertical position and downward pressure is required to move the dial toward the second vertical position. An additional magnet is included on a flexible arm carried by the switch ring. Upon movement of the dial from the first vertical position to the second vertical position, the magnet is moved in a direction toward another Hall effect sensor mounted on the printed circuit board. This Hall effect sensor produces a signal whenever the dial is depressed, which signal may be used to control the associated portable computer. The '980 patent further states that a momentary switch may be provided, such as in the center of the dial, for producing another computer control signal.

According to the '980 patent, the multiple switch rotary dial input device described therein, that generates signals from the rotation of the dial and the depression of the dial and/or a momentary switch, may be used in place of conventional mouse input devices as a mechanism for controlling and entering information into a computer. For example, the '980 patent states that the dial may be rotated to scroll through a list of items appearing on a display device of the computer, and the dial or monetary switch may be depressed to select an identified item. In the preferred embodiment, the dial cannot be depressed while it is being rotated and vice versa.

As another example, U.S. Pat. No. 5,959,611, the disclosure of which is incorporated herein by reference, describes a portable computer system including a CPU, an input interface, a display and an input device, wherein the input device comprises a rotary switch or dial and three on/off switches. The rotary switch may be a 16 position, binary coded rotary switch which outputs a four-digit gray code representing the position of the switch. As is known in the art, a gray code is a special binary encoding scheme in which adjacent numbers or positions have codes that differ in only one bit position. The on/of switches may be momentary push button switches positioned so as to surround the rotary switch.

The input interface translates the rotational movement of the rotary switch and the depressions of the on/off switches into data appropriately formatted for the CPU. Specifically, four conductors carry a first input signal produced by the rotary switch indicative of its position, and each of three separate conductors carry second input signals generated by depression of each of the on/off switches. The '611 patent states that the first input signal may be used to sequentially identify, through rotation of the dial, information appearing on the display, and the second input signals may be used to select an identified piece of information. The input interface may be implemented using a PIC microcontroller that is programmed to encode the first and second input signals into, for example, an eight bit byte transmitted to the CPU consisting of one byte for each switch depression and every turn of the rotary switch. Such an eight bit byte, according to the '611 patent, consists of six significant bits. Bits 5 and 6 represent the rotary switch turning clockwise and counterclockwise, respectively. If one of those bits is set to one, thereby indicating either a clockwise or counter-clockwise rotation, then bits 1 through 4 represent the gray code input signal. If both of those bits are set to zero, then bits 1 through 4 represent the depression of one of four possible on/off switches, only three of which are actually in use in the device described in the '611 patent. In other words, if any of bits 1 through 4 is set to one, then the corresponding switch was just depressed.

As is known in the art, particular portions or zones of a computer display showing a particular character, word or image can be selected, using a mouse or other input device, to cause the computer to perform an action. The '611 patent refers to such zones as hot spots. According to the '611 patent, a user can sequentially identify or step through hot spots provided on the display by rotating the rotary switch in a clockwise direction. Rotation of the rotary switch in a counter-clockwise direction enables the user to step through the hot spots in the reverse order. When the desired hot spot is identified, such as by being made bold or otherwise highlighted, any one of the on/off switches may be depressed to select the identified hot spot, thereby causing the computer to perform an action. Thus, the input device described in the '611 patent may be used to input information into and control a computer much like a conventional mouse.

Figure 42:
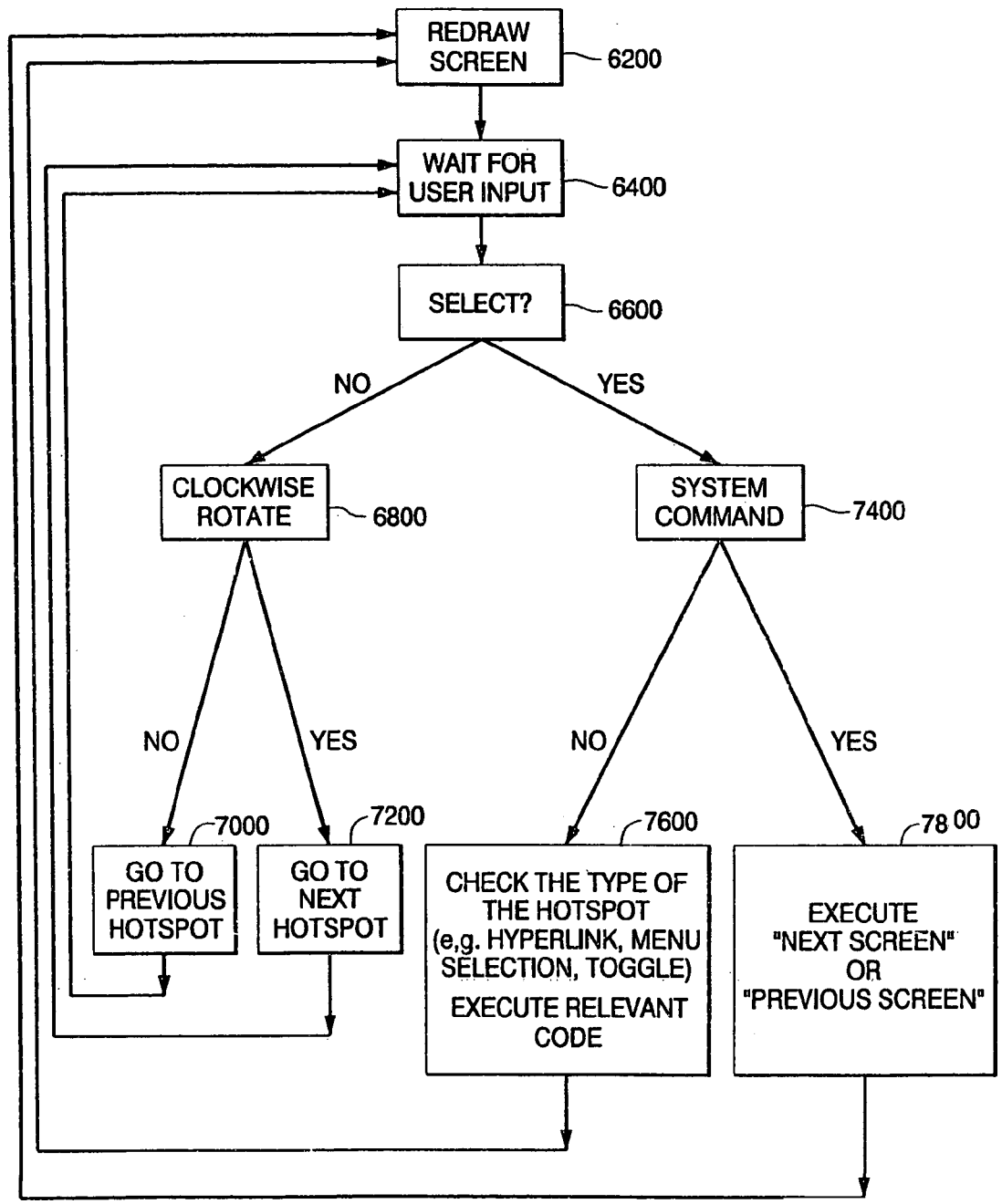
FIG. 42 is a block diagram illustrating the operation of prior art software that enables a prior art input device having a dial and a button to control the operation of a computer by identifying and selecting hot spots.

FIG. 42 is a reproduction of FIG. 5 of the '611 patent and is a block diagram illustrating the operation of the software that enables the input device to identify and select hot spots. In FIG. 42, a screen is drawn or redrawn at step 6200. Thereafter, process control proceeds to step 6200 in which the software awaits input from the user, i.e., the eight bit byte of information provided to the CPU from the input interface. When input is received from the user, step 6600 determines if a selection has been made, i.e., whether of the of on/off switches has been depressed. If none of the switches has been depressed, then the input must be rotation of the rotary switch and process control proceeds with step 6800. At step 6800, a determination is made as to whether the rotary switch has been rotated in a clockwise direction. If so, process control proceeds with step 7200 wherein the next hot spot becomes the active hot spot. If the rotary switch has been rotated in a counter-clockwise direction, process control proceeds with step 7000 in which the previous hot spot becomes the current hot spot. After either step 7000 or 7200, process control returns to step 6400 to await additional user input.

If at step 6600 a selection was made, process control proceeds with step 7400 to determine if a system command had been invoked. If not, the type of hot spot is checked at step 7600, the relevant code is executed, and the screen is redrawn at step 6200. If, on the other hand, a system command is invoked at step 7400, at step 7800 an execution of the next screen or previous screen, as appropriate, is performed and the appropriate screen is redrawn at step 6200. Thereafter, process control returns to step 6400 to await additional user input. In this manner, the rotation of the rotary switch coupled with operation of the push-button switches controls the hot spots and ultimately controls the information displayed on the display and the actions taken by the computer. Those of ordinary skill in the art will recognize that the process illustrated in FIG. 42 can be implemented in software in a variety of ways.

Thus, as is known in the art and as taught by, for example, the '980 and '611 patents, dial 1220 may be used to step through or toggle between or among various input or command or control possibilities presented on LCD 1210 by selectively rotating dial 1220 in either the clockwise or counter-clockwise direction. As dial 1220 is rotated, the various input or command or control possibilities are highlighted. Highlighted items may be selected and a corresponding action commenced by pressing button 1215, or alternatively dial 1220 itself, in which case dial 1220 acts as both a dial and a button as those terms are used herein such that the device in question would be considered to have both a dial and a button. One alternate example of dial 1220 is the knob on the side of a watch that rotates about the side external surface of the watch.

As an alternative to dial 1220, one or more buttons, such as an up button and a down button or left and right buttons, may be used to step through or toggle between or among various input or command or possibilities presented on LCD 1210. In this embodiment, button 1215 may still be used to select and commence a highlighted items. As a further alternative, I/O device 1200 may be provided with voice recognition software and voice commands may be used to step through or toggle between or among various input or command or possibilities presented on LCD 1210. Voice commands may also be used to select and commence a highlighted items. As still a further alternate embodiment, voice commands in combination with voice recognition software may be used to directly enter information, such as nutrition information described below, into I/O device 1200.

Figure 43A:
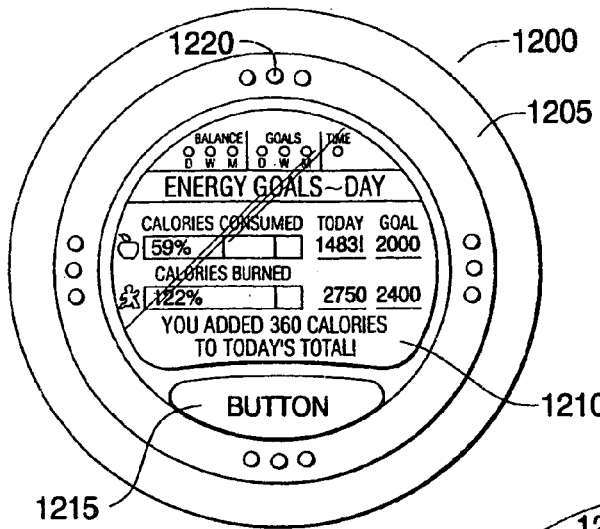
FIGS. 43A-F is a top plan view of a data input and output device according to an embodiment of the present invention in which energy related data for an individual is collected or generated by the data input and output device and a sensor device in electrical communication therewith and displayed by the data input and output device on an LCD provided thereon.
Figure 43B:
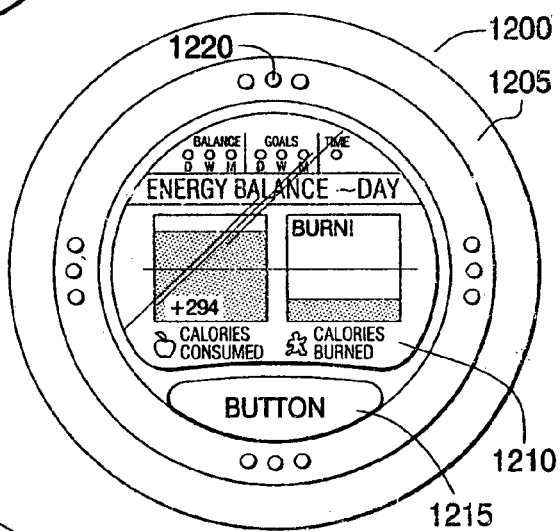
Figure 43C:
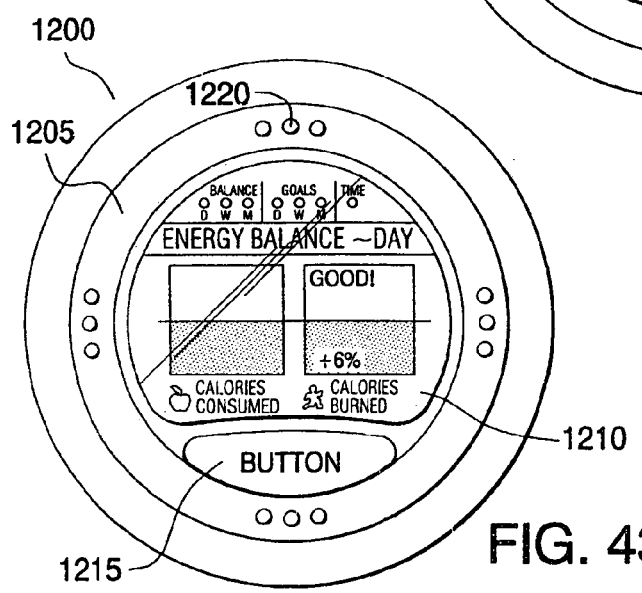

Referring to FIGS. 43A-F, an embodiment of the present invention including I/O device 1200 is shown in which energy related data for an individual is collected or generated by I/O device 1200 and sensor device 1201 and displayed by I/O device 1200 on LCD 1210. As seen in FIGS. 43A-C, the energy related data may include calories consumed and calories burned by the individual over specific time periods such as a day, a week or a month. In FIG. 43A, this data is presented in a format that provides a comparison to a predetermined goal for each value. The example shown in FIG. 43A shows that a daily goal of 2000 calories consumed was set by the individual and that the individual has consumed 1,483 calories on the day in question, and that a daily goal of 2,400 calories burned was set by the individual and that the individual has burned 2,750 calories on the day in question. Referring to FIGS. 43B and C, the data is presented in a format referred to as energy balance in which the amount of calories consumed by the individual is compared to the amount of calories expended or burned by the individual for daily, weekly or monthly periods. It will be appreciated that the individual may toggle between the goal based and energy balance formats just described, and among the various time periods within each, by rotating dial 1220 and, in one embodiment, also pressing button 1215. Depending upon the rotation of dial 1220 and, in one embodiment, upon pressing of button 1215, appropriate information is displayed sequentially on LCD 1210. For example, in FIG. 43A, LCD 1210 is shown displaying data in the goal based format for a daily time period. LCD 1210 may be caused to display the data in the goal based format for a weekly or monthly period by progressively rotating dial 1220 in the clockwise direction. Similarly, LCD 1210 may be caused to switch from displaying data in the goal based format shown in FIG. 43A to displaying data in the energy balance format for the various time periods by progressively rotating dial 1220 in the counter-clockwise direction.

Figure 43D:
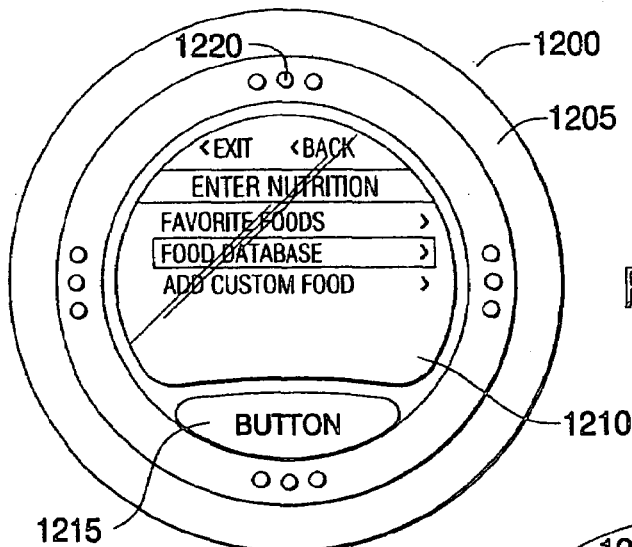

The calories burned data that is displayed by I/O device 1200 may, according to one embodiment of the present invention, be generated by sensor device 1201 from the physiological and/or contextual parameters it detects and thereafter transmitted to I/O device 1200 for storage, use in appropriate calculations and/or display. The calories burned data may also be generated using data that is input by the user in addition to the detected parameters. Furthermore, the caloric consumption data that is displayed by I/O device 1200 may, according to one embodiment of the present invention, be generated, preferably by I/O device 1200 but also by sensor device 1201, from data input into I/O device 1200 by the individual relating to foods consumed (as described elsewhere herein, caloric consumption data may also be generated using various detected parameters in addition to information that is input manually). Specifically, I/O device 1200 may be provided with access to a user accessible database of foods and corresponding caloric value. Such a database may be provided as part of I/O device 1200 itself, as in the case of the preferred embodiment of the present invention, or I/O device 1200 may be able to access a database stored and maintained on a computing device located separately from the I/O device such as through short or long distance wireless or wired communications. Referring to FIG. 43D, LCD 1210 is shown displaying an ENTER NUTRITION menu screen that may be accessible from, for example, a main menu screen presented on LCD 1210 using dial 1220 and button 1215. When the individual eats a particular food, he or she may enter it into I/O device 1200 for storage and/or use thereby by rotating dial 1220 until the FOOD DATABASE line of the ENTER NUTRITION menu screen shown on LCD 1210 is highlighted and thereafter pressing button 1215 to select same. Once the food database has been selected, the individual is, in this embodiment, presented with the search screen shown on LCD 1210 in FIG. 43E. The individual may sequentially spell out the name of the food consumed by rotating dial 1220 to each letter and selecting the letter by pressing button 1215. When the individual has finished spelling the food in question, he or she rotates dial 1220 until SEARCH is highlighted and then presses button 1215. In response, as shown in FIG. 43F, I/O device 1200 presents a list on LCD 1210 of foods that match the entered search information. The individual may then select the appropriate food by rotating dial 1220 and pressing button 1215. When this is done, the corresponding caloric information may be displayed to the user on LCD 1210 and will be stored by I/O device 1200 as part of the caloric consumption data for that day. The database may include several sub-entries for each food that correspond to particular serving sizes, such as a 3 oz. slice of pie or a 6 oz. piece of chicken, and the appropriate caloric value associated therewith. As will be appreciated by one of skill in the art, these sub-entries may be presented to the user and selected using dial 1220 and button 1215 in the manner described above. Referring again to FIG. 43D, I/O device may also be used to store a list of favorite foods that are consumed frequently. By selecting the FAVORITE FOODS line from the Enter Nutrition menu screen provided on LCD 1210 and subsequently selecting the appropriate favorite food, both done by using dial 1220 and button 1215, an individual eliminates the need to search through the database as described above. In addition, an individual may add a custom food and associated caloric value to the food database using dial 1220 and button 1215 by selecting the ADD CUSTOM FOOD line from this Enter Nutrition menu screen provided on LCD 1210 and using a subsequently provided alpha-numeric entry screen similar to that shown in FIG. 43E to enter the food name and caloric information. Once entered, this custom food will be accessible from the food database. As will be appreciated to those of skill in the art, the information displayed on LCD 1210 may be shown in list menu or serial menu format.

Figure 43E:
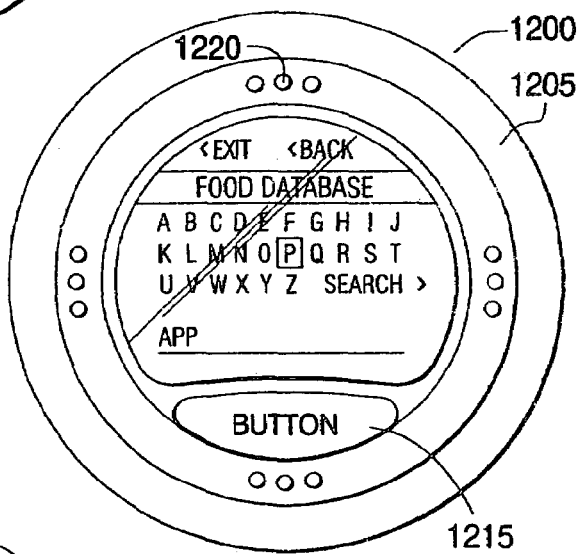
Figure 43F:
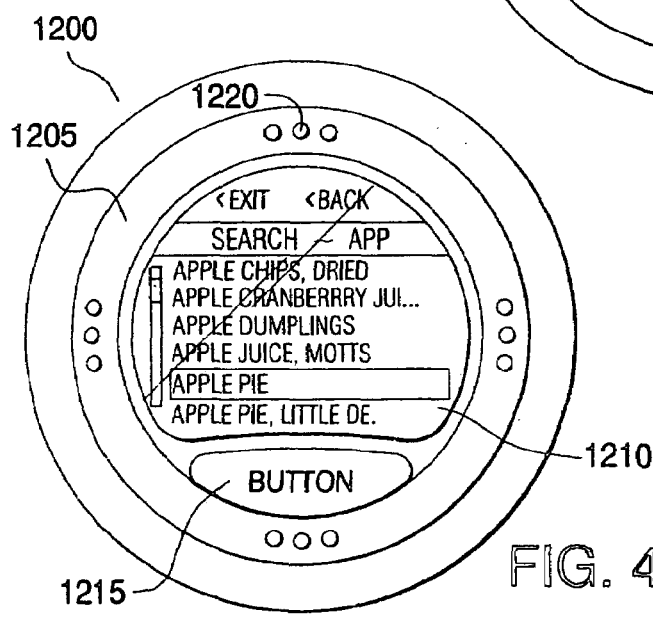

Although FIGS. 43D-F illustrate the use of a database of food information according to one embodiment of the present invention, it will be appreciated that any database of information maybe used with I/O device 1200 without departing from the scope of the present invention. For example, the database could store a number of activities, such as walking, running or biking for a particular time period, and the caloric expenditure associated with each. In such a configuration, I/O device 1200 would enable an individual to input and track his or her caloric expenditure over a period of time. Furthermore, it will be appreciated that I/O device 1200 is not limited to receiving and displaying information relating to caloric consumption and expenditure as shown in FIGS. 43A-F. Instead, I/O device may receive and display many different types of information from one or both of sensor device 1201 and the user, including, for example, information relating to sleep states and patterns.

It is also possible to enter nutrition information in a considerably simplified manner in any of several potential forms, including single dimensional point systems, single dimensional categorical rating systems, and multi-dimensional categorical rating systems. For a simple example of a single-dimensional point system, the user may select from a 7 point scale, where each point value corresponds to a rough approximation of the relative size of the meal in relation to the user's normal sized meal. For an example of a categorical system, the user may select from the set {tiny, small, medium, large, and super-size} when describing a meal. An example of a multi-dimensional categorical system is the grid system described below.

For each of these systems, the users are asked to score each meal (including snacks) according to the choice of scoring system. The user's classification of the meal, as identified by a classification identifier chosen by the user, is used as an input to an algorithm that estimates the caloric content of the meal. The algorithm that does this calculation may take other factors into consideration, including, but not limited to, the time of day, the day of the week, the season, whether the day is a holiday, the user's past meal habits, the raw or derived values from a body monitoring product such as sensor device 1201, demographic information, and trends in the user's reporting of data. The algorithm may be a simple look-up table where each classification identifier is associated with a caloric amount, but can be more complicated as well.

Figure 43G:
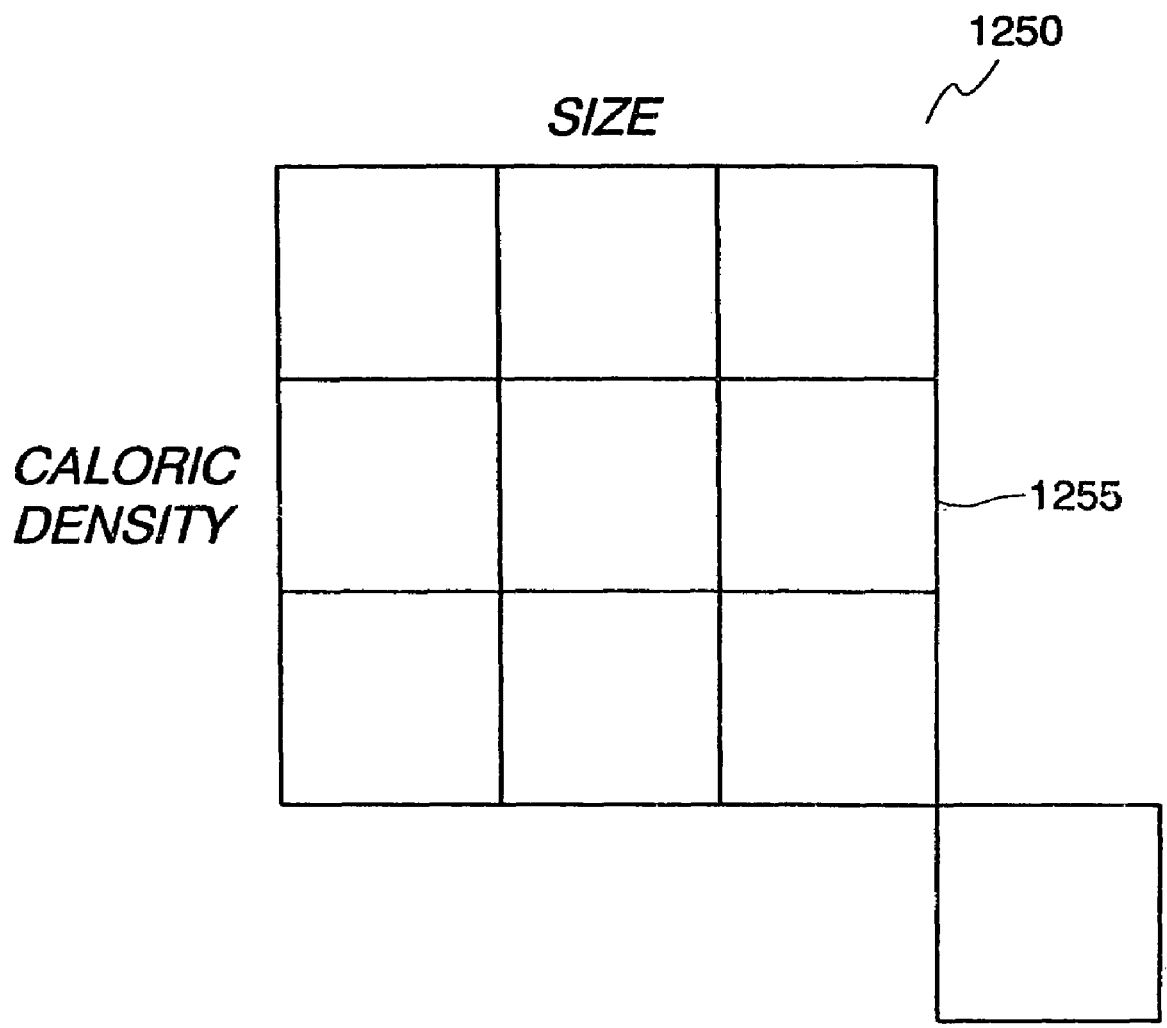
FIGS. 43G and H are a plan views of interfaces for entering nutrition information into a data input and output device according to an alternate embodiment of the present invention.

Referring to FIG. 43G, an alternate interface 1250 displayed on LCD 1210 for entering nutrition information into I/O device 1200 is shown which simplifies user interaction. In connection with interface 1250, users are provided with a two-dimensional grid-based system based on grid 1255 and are asked to rate each meal, including snacks, according to a grid system based on the size of the meal or snack, shown on the horizontal axis of grid 1255, and the estimated caloric density of the meal or snack (essentially the fat content), shown on the vertical axis of grid 1255. The grid squares are then translated into caloric estimates (or caloric estimate ranges) using any of a variety of algorithms. In one embodiment, the grid squares correspond directly to caloric estimates via a lookup table derived from aggregate population statistics. In another, the corresponding caloric estimates are based on a weighted combination of a user's own previous data and aggregate population statistics. The user may answer a pair of questions instead of directly choosing a grid square. The pair of questions first may ask about the size of the meal, and then may ask about the caloric density.

This system of quick caloric entry has been tested and verified in both an in-house pilot study with ten subjects over several months conducted by the assignee of the present application and a brief three-day study of 41 participants. In both studies, the following method was used. For each subject, the data from all of the other subjects was used to generate caloric estimates for each grid category for each meal type. The estimates from that aggregate information were then compared to the computed caloric totals calculated from full diet diary entries. FIG. 43I shows a scatter plot between the estimates of the caloric content based on the present invention and those computed from the full diet diary entries for one of the subjects in the in-house study, and FIG. 43J shows the relationship between the estimates of the caloric content based on the present invention and those computed from the full diet diary entries for the three-day. The correlation between the estimates of the in-house study and the diet diary caloric totals was 0.80, and the estimates of the three-day study and the diet diary caloric totals was 0.57, without any normalization by each subject's basal metabolic rate. This data, taken with the most simple of the embodiments of the system, strongly supports the premise that diet recording using a quick entry system can result in reasonably accurate estimates of a user's daily caloric intake.

Figure 43H:
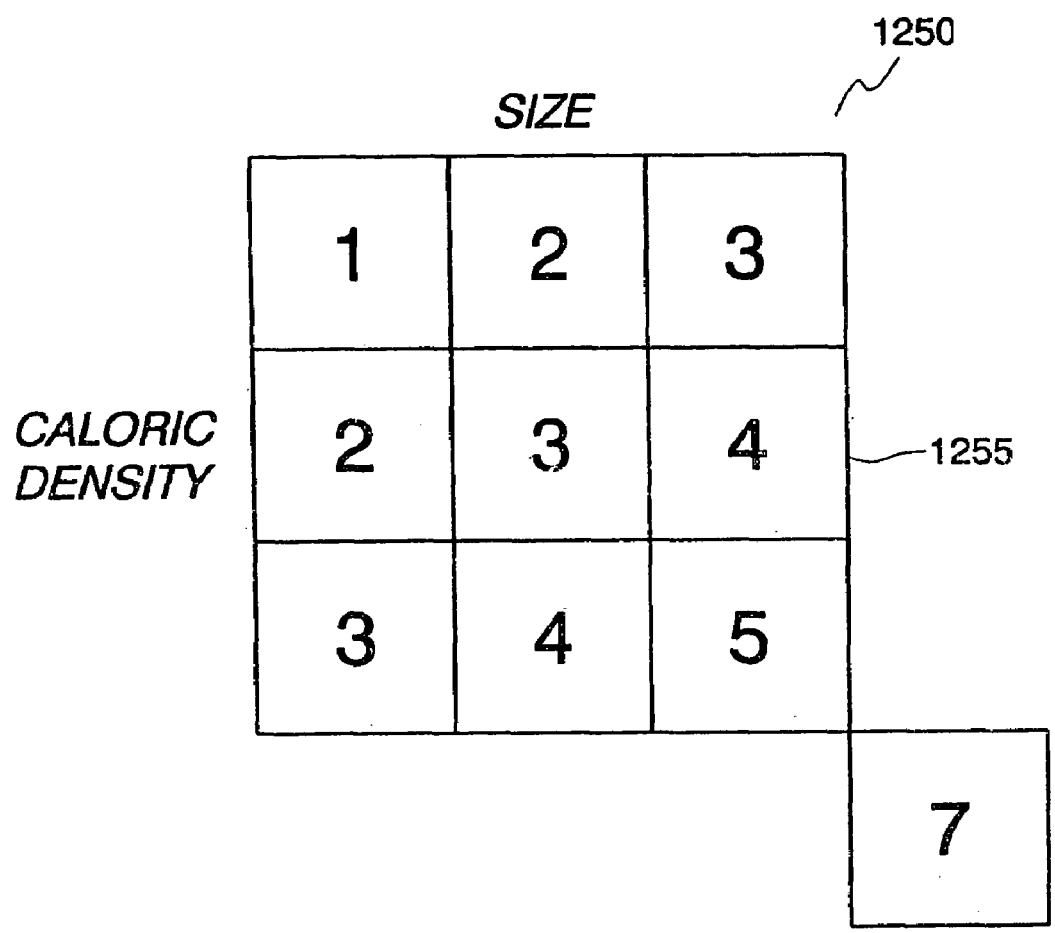
FIGS. 43I and J are scatter plots between estimates of the caloric content in meals consumed using an embodiment of the present invention and caloric content computed from full diet diary entries.
Figure 43I:
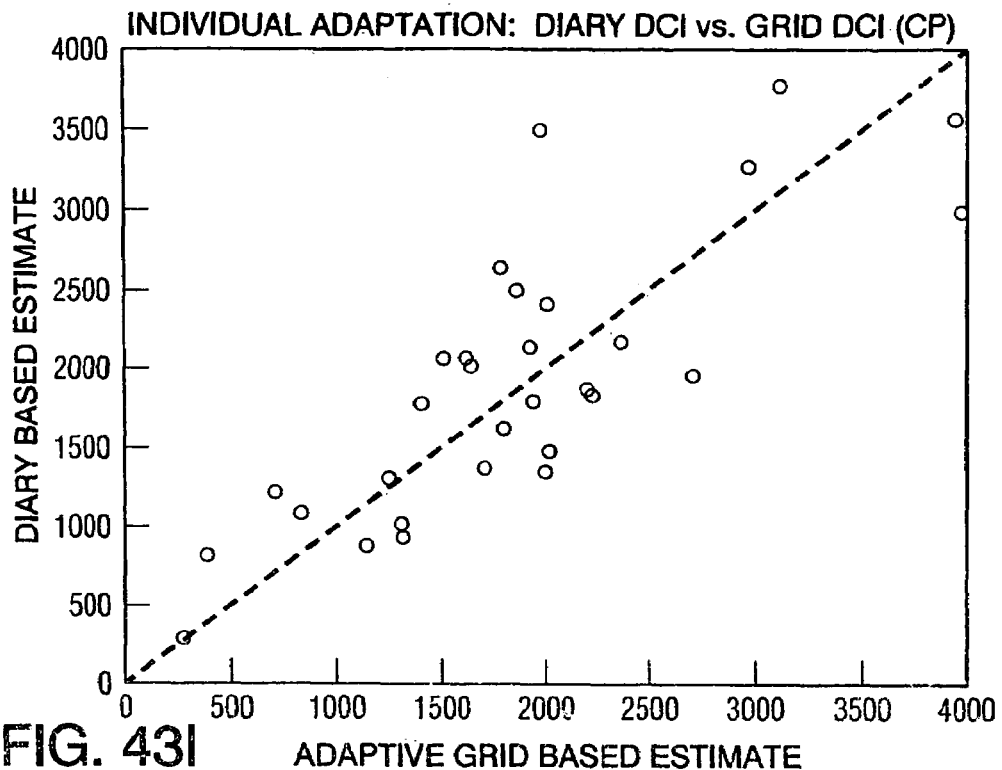
Figure 43J:
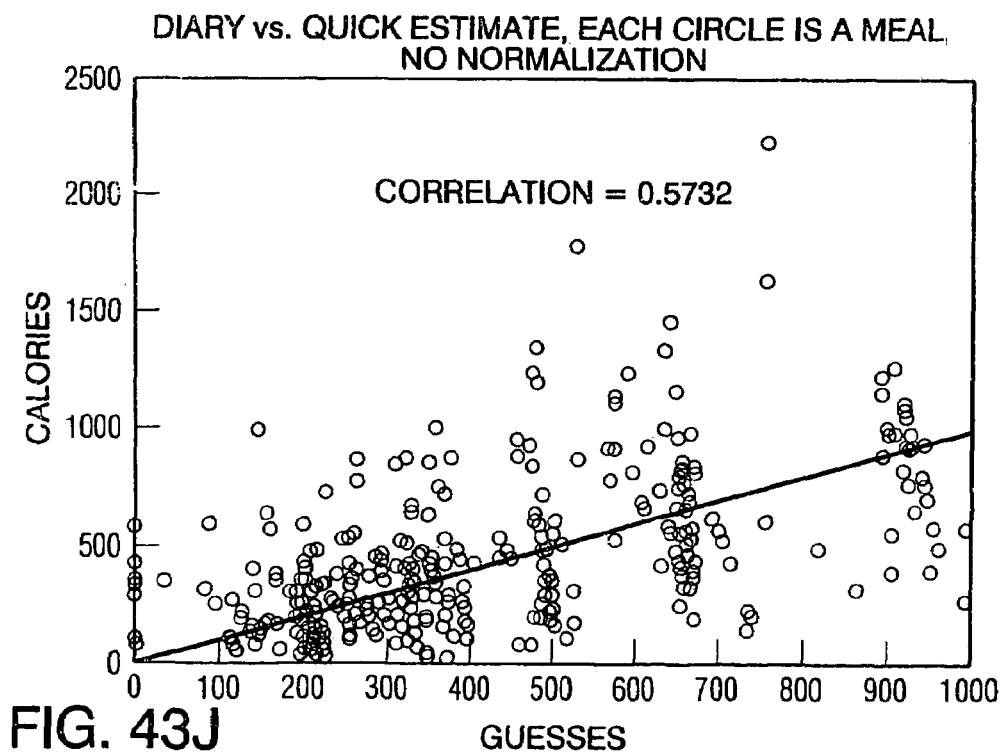

Referring to FIG. 43H, a further alternate interface 1250 displayed on LCD 1210 for entering nutrition information into I/O device 1200 is shown which simplifies user interaction. In connection with interface 1250, users are provided with a point system based on grid 1255 and are asked to score each meal, including snacks, according to a point system based on the size of the meal (including snacks), shown on the horizontal axis of grid 1255, and the estimated caloric density for the meal (including or snacks), shown on the vertical axis of grid 1255. The points act as categories enabling the user to classify each meal, including any snacks, and thereby associate a caloric amount with the meal. Users may also be given a baseline size and calorie value to be associated with each point level. For example, a 1 may be set to be a meal that is the size of a fist having an estimated calorie value of 300-500 calories, a 2 may be set to be a meal that is either the size of a fist having an estimated calorie value of 500-700 calories, or the size of a fist and a half with a calorie value of 300-500 calories, and so on, with a 7 being a super-size meal that exceeds any of the provided levels. In addition, the meal score may further be weighted, by multiplying the score by a weighting factor, depending on whether it is breakfast, lunch, dinner or a snack. The user can use dial 1220, or alternatively one or more buttons or voice commands, to toggle among the scores or points shown in grid 1255 and button 1215 to select a score or point level. Each point level has associated therewith a caloric value or amount, which may be a range of calories, that is saved for the meal in question. The associated caloric amounts may be a generic values designed to suit the public at large, or may be specific values tailored to particular individuals. It will be appreciated that, depending on the grid 1255, the user, in selecting a point level, may actually be making two selections, one based on the horizontal axis of the grid (size of meal) and the other based on the vertical axis of the grid (caloric density of the meal). In addition, according to a particular embodiment, the I/O device 1200 is programmed to adjust its settings over time based on information that is collected. For example, if a user begins a week weighing 200 pounds and at the end of the week should weigh 197 pounds based on the input nutrition and other information, but instead actually weighs 202 pounds, the problem could be that what the user thinks is a 1 point meal is actually a 2 point meal. To account for this problem, I/O device 1200 can, over time learn and adjust or calibrate its settings and how it does its calculations to personalize itself for the user by, for example, increasing the number of calories associated with a user's classification. This learning process thus increases the accuracy of I/O device 1200. One method for implementing this automatic calibration is to use Bayesian statistics and use an initial prior for the caloric value of the classifications based on aggregate user statistics and then to train it for the given user over time as data is entered into the system. As another embodiment, the system can allow the wearer to input both simplified dietary information (such as the grids shown in FIGS. 43G and H) and full dietary information about the meals that are eaten. The caloric amounts from the full dietary information can easily be calculated and used to train the caloric estimates for each category. In addition, as I/O device learns, adjusts or calibrates, it may also modify the goals of the user and the program he or she is following. As still a further alternative, I/O device 1200 can take the information it has accumulated over time and provide information automatically for a user. For example, if a user forgets to enter a lunch value, I/O device may be programmed to enter the average of a predetermined number of, such as the last ten or even all, lunch values for the missing lunch. This may be done automatically, or only after prompting the user for verification of the values and authorization to do so. Alternatively, I/O device may fill in such gaps by matching that days routine to a previous day's routine, and using the lunch or other missing value from that day, thereby taking advantage of the fact that people tend to be creatures of habit.

Another aspect of the invention is that of automatic adaptation of feedback given to the user by sensor device 1201 or I/O device 1200. The feedback given to the user in this invention (e.g. "you might want to run an extra 10 minutes today") can be given exactly when appropriate by taking advantage of the system's ability to detect contexts and to auto-journal as describe elsewhere herein. For example, feedback for eating might be best given just before a meal, and exercise feedback might be best given right when the user is most likely to exercise. Furthermore, if the system has detected that the user has already jogged that day, then an alternate suggestion can be given. Finally, the user's response to feedback can be utilized to further adapt the choice of the given feedback. If the user never takes exercise suggestions, advice can focus instead on nutrition. If the user tends to respond better to feedback given in the morning, more feedback can be given in the morning. The method of noticing their response would be measured by adherence to the suggestions and by successful maintenance of a healthy eating balance, as well as by noticing the absence of "violent" responses such as hitting a button that turns feed back off, turning the device off, or abruptly taking off the device.

There are three main ways in which sensor device 1201 can calibrate itself to the user. First, the device can use an initial training or calibration period where the user performs some additional tasks to train the system. For example, the user can enter in a full diet diary in addition to the quick estimates, allowing the system to learn the user's own definitions for each meal classification. The user might additionally perform a program of activities (such as walking around the block for at least 10 minutes or resting for 20 minutes) in order to calibrate a subsystem for obtaining energy expenditure that may be provided in sensor device 1201 and obtain personalized parameters for the individual that are then used in later use of the system. The subsystem for obtaining energy expenditure may also be calibrated against gold standard data from, for example, a VO2 machine. The second method involves repeating the training procedures (or a subset thereof) every so often. One example of this would be for a glucose level prediction algorithm where, each week (for example), the user performs a finger-prick glucose test to calibrate the prediction system. The third method involved doing continual training while the user is using the system including sensor device 1201. For example, the system described above that utilizes discrepancies in predicted weights between the system's prediction and that reported by a scale to adjust the estimated caloric amounts for each category is an example of this type of training.

According to a further aspect of the present invention, the user can be queried to answer questions that the sensor device 1201 or I/O device 1200 can not figure out for itself, or about which it has too much uncertainty. For example, the sensor device 1201 or I/O device 1200 may have enough information to ask the user only a single question about breakfast, but may require more information for a morning snack that the user doesn't have every day. The system can ask the questions specifically when the range of its uncertainty about a quantity is too large, and can thus minimize the input required from the user.

According to a further aspect of the present invention, I/O device 1200, sensor device 1201 and a computing device such as a PC or a PDA may be used together as a weight management system. Specifically, I/O device 1200, such as a watch like device, is used to input and track information relating to calories consumed by an individual and sensor device 1201 is used to measure calories burned or expended by the individual. The caloric expenditure information measured by sensor device 1201 is transmitted, by wire or wirelessly, to I/O device 1200. I/O device 1200 then, based on the caloric consumption and caloric expenditure information, displays to the individual a current rate of weight loss or gain and/or an energy balance value on LCD 1210. According to a specific embodiment, sensor device 1201 assumes that the individual is inactive if sensor device 1201 is not being worn, and uses the individual's resting metabolic rate to calculate caloric expenditure during such period.

In one embodiment, the individual, for each meal, including snacks, rather than inputting a specific food or foods selected from a database as described in connection with FIGS. 43D-43F, merely classifies each meal according to an indication of the estimated size of the meal (in terms of an estimated caloric value) using classifiers such as small (S), medium (M), large (L) or extra large (XL). Each classifier is assigned a corresponding caloric amount, and I/O device 1200 stores for the meal the caloric amount corresponding to the entered classifier. To enable the individual to enter this information, I/O device 1200 first displays on LCD 1210 a list of each meal possibility, i.e., breakfast, lunch, dinner or snack. The individual is able to toggle among these selections using dial 1220 or one or more buttons, and select one using button 1215. Once the meal classification is selected, I/O device 1200 displays on LCD 1210 a list of the classifiers such as S, M, L, and XL. Again, the individual is able to toggle among these items using dial 1220 or one or more buttons, and select one using button 1215. When one of these classifiers is selected, the corresponding caloric amount is saved for the meal in question and is used to generate the caloric consumption information used by I/O device 1200. I/O device 1200 may be programmed to prompt the individual to enter meal information if the individual has not done so by a certain time or times each day.

In a preferred embodiment, the computing device is provided with weight management software that enables the individual to input information relating to foods actually eaten during each meal using a database such as that shown in FIGS. 43D through F. Based on the information that is input, a specific caloric amount is assigned to each meal entry. The individual is also able to enter information relating to weight goals, such as how much weight the individual wants to lose and over what time period the individual wants to lose the weight. Based on this information, a target weight loss rate may be established for achieving the input goal. In this embodiment, the individual, while entering information into I/O device 1200 using the S, M, L, and XL classifier system, also enters information into the computing device using the weight management software for a predetermined time period. Sensor device 1201 is in electronic communication, by wire or wirelessly, with the computing device to enable information to be transmitted from the computing device to sensor device 1201. Specifically, the information that is transmitted from the computing device includes information relating to the weight goals, namely target weight loss amount, time frame and rate, and information relating to the caloric amount associated with each meal eaten by the individual based on the food items input into the computing device. Sensor device 1201 may then transmit the information to I/O device 1200. Alternatively, I/O device 1201 maybe in electronic communication, by wire or wirelessly, with the computing device so that the information may be transmitted directly to the I/O device 1200. According to an aspect of the present invention, I/O device 1200 compares the caloric amounts entered for each meal using the S, M, L, and XL classifiers with the caloric amounts entered for each meal using the computing device and database of food information over the predetermined time period, and make adjustments to the caloric amounts that are associated with each of the classifiers so that they more accurately reflect calories actually consumed. Thus, in this specific embodiment, the individual enters nutrition information both using I/O device 1200 and the computing and database for a specified period of time, for example two weeks, after which the entry system on I/O device 1200 is calibrated or adjusted to bring the individual's perception of what should be classified as S, M, L, or XL based on calories in line with more accurate caloric data. After this initial period, the individual only enters nutrition information using I/O device 1200 and the S, M, L, and XL classifiers, and caloric data is recorded for each meal depending on how the meal is classified.

In a preferred embodiment, I/O device 1200 is programmed to provide suggestions to the individual, in the form of information displayed on LCD 1210, on how to achieve the individual's weight goals. These suggestions are based on the caloric expenditure and caloric consumption data that is logged by I/O device 1200. For example, if the individual is currently below the target weight loss rate of, for example, 1 pound per week, I/O device 1200 may display a message that instructs the individual to walk for 55 minutes to bring the current weight loss rate up to 1 pound per week. The suggestions may be of many types, including, without limitation, actions for the individual to take, explanations for why the individual is experiencing certain things such as inability to lose weight, feedback regarding the individual progress toward goals, and/or relationships between or among the parameters being measured and/or reported by sensor device 1201 and/or I/O device 1200. The suggestions may self adjust or learn based on the individual's performance toward goals. The substance of the suggestions may come from a number of sources, such as sensor device 1201 and/or I/O device 1200 or a third party source, including a person such as a trainer or health care provider, a computing device such as a treadmill, or a remote computer, such as an Internet source.

As noted above, in one embodiment, I/O device 1200 displays a current weight loss or gain rate on display 1200. The current weight loss or gain rate that is displayed on I/O device 1200 may be a daily, weekly or monthly rate, or may be a rate calculated based on the total time remaining until the weight loss target date. I/O device 1200 may be programmed to selectively display each of these rates depending on the desires of the individual, such as by using dial 1220 or one or more buttons to toggle among these various options.

Figure 44:
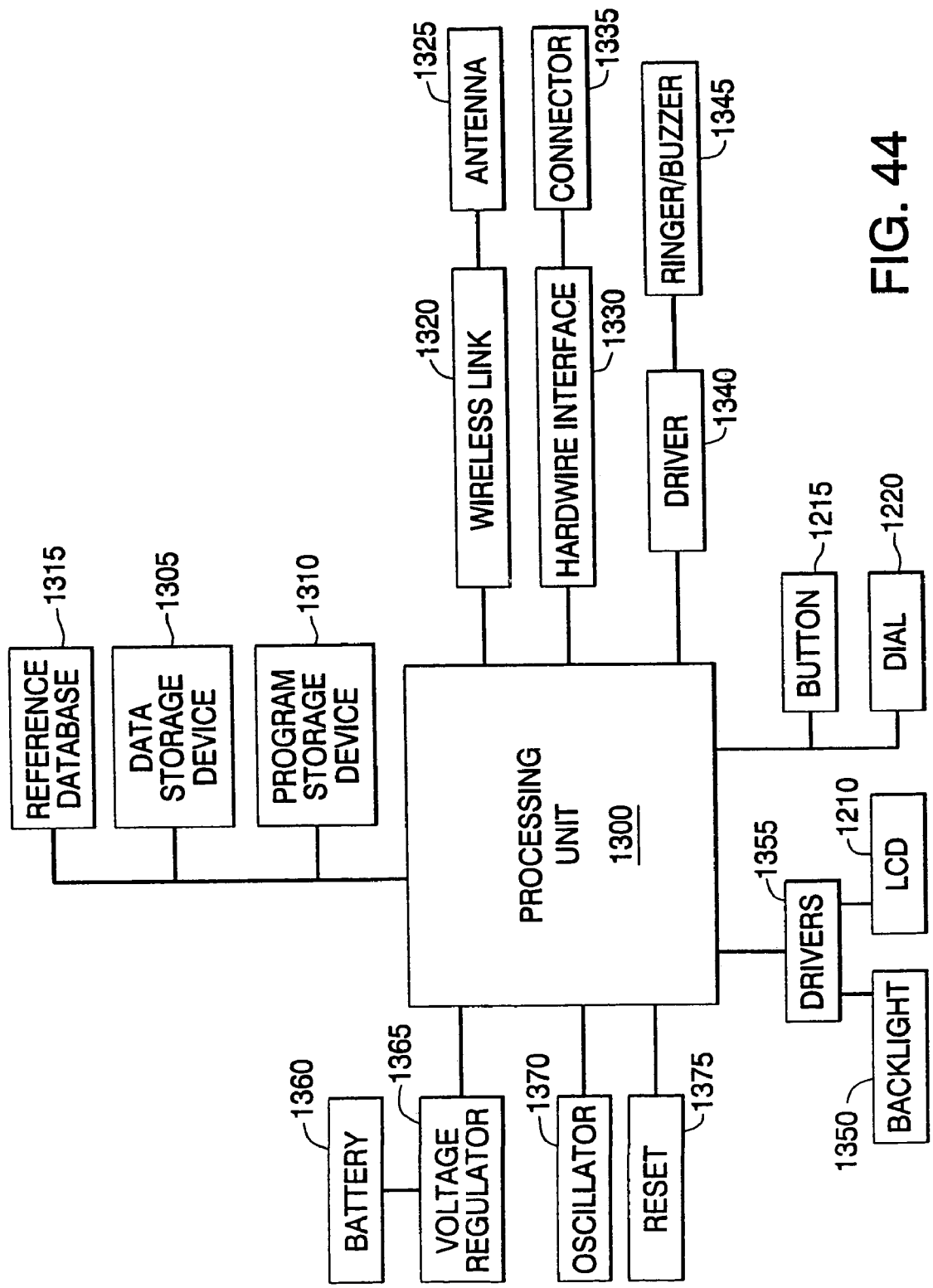
FIG. 44 is a block diagram showing the components attached or otherwise coupled to a printed circuit board housed within a data input and output device according to an embodiment of the present invention.

FIG. 44 is a block diagram showing the components attached or otherwise coupled to a printed circuit board (not shown) housed within housing 1205 of an embodiment of I/O device 1200. Included among these components is processing unit 1300, which may be a microprocessor, a microcontroller, or any other processing device that can be adapted to perform the functionality described herein. Connected to processing unit 1300 are non-volatile data storage device 1305, such as a flash memory, chip for storing information input and/or transmitted to I/O device 1200, and non-volatile program storage device 1310, such as a FLASH ROM chip, for storing the programs required for operation of I/O device 1200. Also provided is reference database 1315 which may, as described in connection with FIGS. 43D-F, be used to provide user accessible and selectable information for use by I/O device 1200 or sensor device 1201. As is known in the art, reference database 1315 includes a software component for organizing and accessing data, and a memory component for physically storing data. Also connected to processing unit 1300 are one or both of wireless link 1320, such as an RF transceiver, connected to antenna 1325, and hardware interface 1330, such as a USB port, connected to connector 1335. These components are used to implement communications connection 1230 shown in FIG. 40, and may also be used to communicate electronically with a wide variety of devices, such as a treadmill, a weight scale or a transceiving device adapted to act as a data collection and storage hub. Driver 1350 and ringer/buzzer 1345 may also be connected to processing unit 1300 to provide audible and/or tactile feedback to a user.

LCD 1210 and backlight 1350 for LCD 1210 are connected to processing unit 1300 through appropriate well known drivers 1355. Battery 1360, which may be disposable or rechargeable, provides power for I/O device 1200 and is connected to processing unit 1300 through voltage regulator 1365. Oscillator 1370 provides the system clock to processing unit 1300, and reset circuit 1375 enables processing unit 1300 to be reset to a standard initial setting. Finally, button 1215 and dial 1220 are electronically connected to processing unit 1300 according to any known means, such as those described in the '980 and '619 patents, which would enable button 1215 and dial 1220 to provide input or command or control signals to processing unit 1300.

Figure 45:
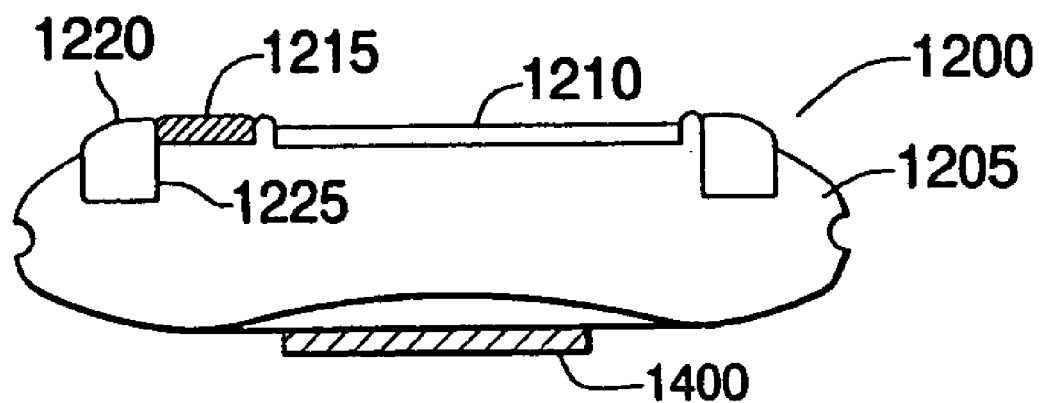
FIG. 45 is a partial cross-sectional view of a data input and output device according to an alternate embodiment of the present invention having one or more sensors that enable it to collect data indicative of physiological and/or contextual parameters.

According to an alternate embodiment of the present invention, I/O device 1200 may be adapted to operate on its own, without being in communication with sensor device 1201. In this embodiment, a user may enter information into I/O device 1200 as described herein and may use I/O device to store and track such information over time. For example, reference database 1315 may store food and activity related information and a user may enter caloric consumption and caloric expenditure or burn information as described in connection with FIGS. 43D-F. The entered information would in this embodiment be stored in data storage device 1305, and processing unit 1300 would be programmed to generate and display the information shown in FIGS. 43A-C. In such an embodiment, RF link 1320, antenna 1325, hardware interface 1330 and connector 1335 would not be required since communication with sensor device 1201 is not necessary, but may be included as optional enhancements. For further added functionality, one or more sensors 1400, such as those described in connection with sensor device 400, stand alone sensor device 700 and sensor device 800, may be, as shown in FIG. 45, attached to, supported by or otherwise coupled to I/O device 1200, enabling it to collect data indicative of physiological and/or contextual parameters. In one specific embodiment, sensor 1400 may be a heart rate sensor in the form of a chest strap. In another specific embodiment, sensor 1400 may be a non-ECG heart parameter sensor such as that described in the '005 patent. Sensor 1400 in this embodiment maybe used in connection with heart rate information collected by sensor device 1201, such as ECG information obtained from the upper arm, to make pulse transit time measurements, which, as is known in the art, are an indication of cardiovascular health and have a relationship to blood pressure. Such pulse transit time measurements may also be calibrated against measurement using a traditional blood pressure cuff for increased accuracy. This collected data, other data entered by the user, and/or one or both of derived data and analytical status data generated therefrom, may be displayed to the user using LCD 1210 or some other output/feedback device such as a screen on a treadmill, headphones worn by the user, or an earpiece such as those worn by first responders.

Figure 46:
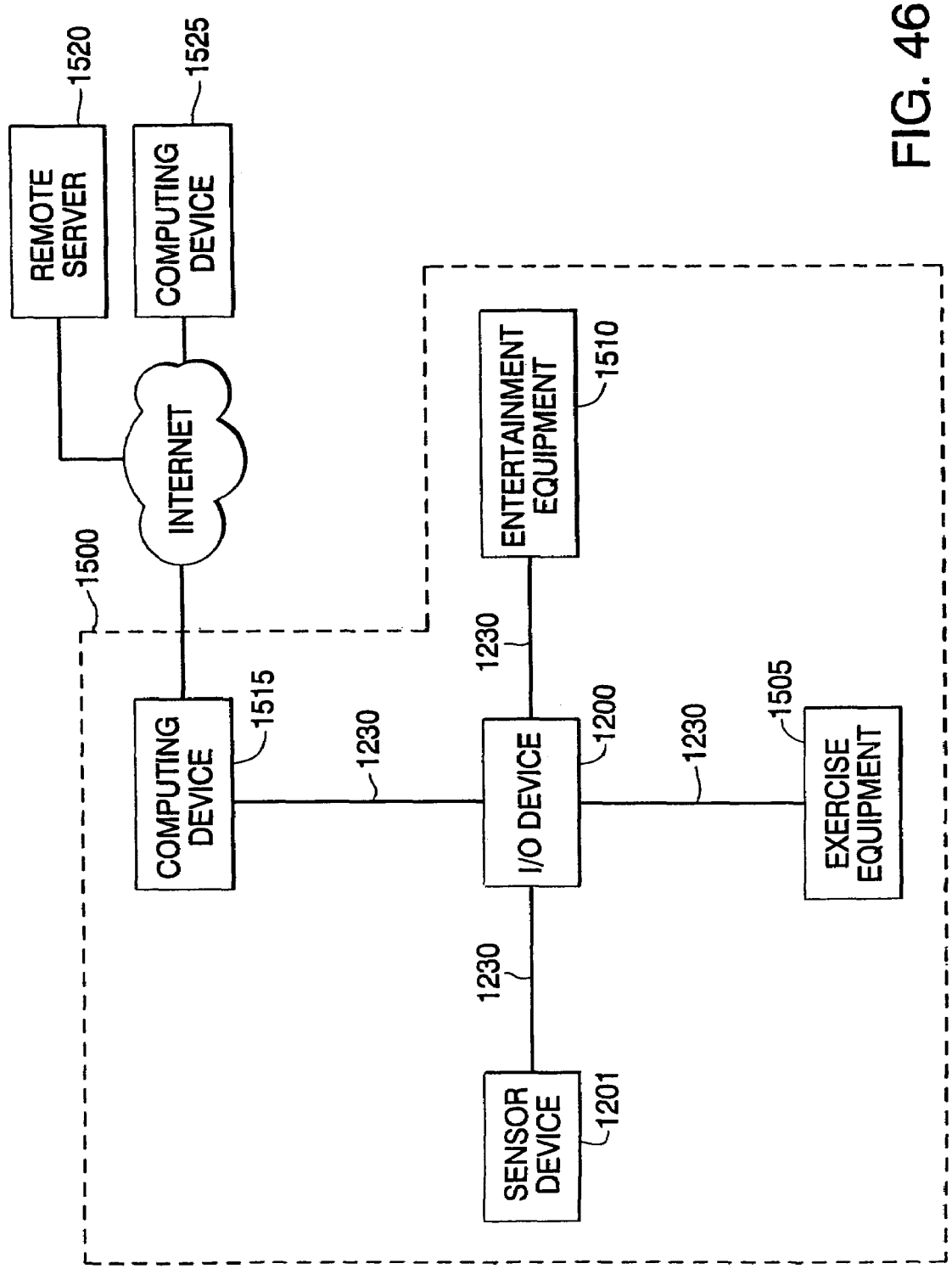
FIG. 46 is a block diagram of an alternate embodiment of the present invention in which a data input and output device acts as a hub or terminal for collection and, optionally, processing of data from a variety of sources.

According to a further alternate embodiment of the present invention, I/O device 1200 may act as a hub or terminal for collection and, in a specific embodiment, processing data received from a variety of sources. For example, referring to FIG. 46, I/O device 1200 may be used as a hub or terminal in health club 1500 to collect and, in a specific embodiment, process data relating to a user's activities in health club 1500 received from a variety of devices located in health club 1500. In this embodiment, I/O device 1200 may take the form of a watch-like device that is worn by the user on his or her wrist, clipped to the clothing of the user, or otherwise carried by the user. Referring to FIG. 46, I/O device 1200 is in electronic communication with exercise equipment 1505 through communications connection 1230, which may be a wired connection, but which preferably is a wireless connection. Exercise equipment 1505 may be any type of exercise equipment, such as a treadmill or exercise bike, that possesses the ability to generate data relating to the exercise being done and transmit the data to I/O device 1200 over communications connection 1230. I/O device 1200 is thus able to collect and store data relating to exercise activity such as the calories expended during a workout or the duration of the workout. In addition, I/O device 1200 may be programmed to store settings and/or exercise programs for each of the various types of exercise equipment 1505 such that the settings and/or exercise programs may be transmitted over communications connection 1230 to exercise equipment 1505 prior to commencement of a workout for controlling it during the workout. As a further alternative, I/O device 1200 may be provided with an artificial intelligence based program or algorithm that modifies, based on the information collected by I/O device 1200, the exercise program being followed by the user. As still a further alternative, the settings used by and/or exercise programs followed by a user can be set or modified remotely by a trainer or similar individual and be communicated to I/O device from computing device 1515 or through computing device 1515 from a remote source over the Internet, described in detail below. It will be appreciated that I/O device 1200, preferably being portable, is able to collect and store data from a number of different pieces of exercise equipment 1505 that are used by the user as he or she moves around health club 1500, or, as described elsewhere herein, while the user is outside of health club 1500, for example at home or while traveling.

As seen in FIG. 46, I/O device 1200 may also be in electronic communication with sensor device 1201 through communications connection 1230, which preferably is a wireless connection, but which may be a wired connection such as with a cradle. Thus, as described in greater detail in connection with FIGS. 41 through 45, I/O device 1200 is able to collect and store data relating to the physiological parameters of the user before, during and after any exercise activity. For low bandwidth applications, methods are known for transmitting electronic signals through the body. Thus, if both I/O device 1200 and sensor device 1201 are in contact with the user's skin, it may be possible to transmit data using the user's body. Similarly, data may also be transmitted in this manner to other devices by the user by touching them. According to an alternate embodiment of the present invention, sensor device 1201 acts as the hub or terminal for collection and, in a specific embodiment, processing data received from a variety of sources, and as such, would replace I/O device 1200 in FIG. 46.

According to one aspect of the present invention, I/O device 1200 stores a program or regimen preferably including a set of goals that may be established by set by the user or a third party such as a trainer or care giver. I/O device 1200 communicates with and is programmed to control an apparatus in the environment such as a treadmill or weight machine. Specifically, I/O device 1200 is able to communicate instructions to the apparatus for setting the apparatus up for the desired interaction/result, such as choosing treadmill programs or setting or weight machine weight amounts. While user interacts with the apparatus, I/O device 1200, being in communication with the apparatus, tracks the user's performance, preferably with respect to the program or regimen including goals. The tracking maybe based on information received from the apparatus, such as repetitions on a weight machine or distances run on or heart rate measured by a treadmill, and may also be based on parameters being measured by sensor device 1201 or I/O device 1200 such as energy expenditure. I/O device 1200 may also adjust/control the apparatus the user is interacting with to maximize the performance toward the goal, such as by adjusting the treadmill angle and/or resistance to decrease heart rate or energy expenditure rate of the individual. Such adjustment may be important if, for example, the individual is a CVD patient that needs to watch how much they exert themselves. In addition, after the use of the apparatus is complete, I/O device 1200 can adjust the program or regimen so that the next time the user uses the apparatus, the program or regimen will have been adjusted to comply with the progress or lack of progress the person has made. This adjustment could also include free-living exercise and other information that gets collected between periods of use of the apparatus. For example, if the person walked the rest of the week according to their program or regimen, the next time they come to use the apparatus, instead of using the same now outdated program/regimen, the program/regimen is adjusted to meet the user's new capabilities. The principle just described could also apply to interaction with other types of equipment other than exercise equipment, such as medication dispensers, CPAP machines used in sleep therapy, or even a thermostat in the house.

Most health clubs include various devices for providing entertainment to users while they are exercising. For example, a health club may include a number of television monitors, with each monitor providing a different channel of programming. Users are able to listen to the audio portions accompanying the programming while exercising by plugging headphones into an access device provided adjacent to each piece of exercise equipment, and may use the access device to select among the audio portions of the various programming channels. Referring to FIG. 46, I/O device 1200 may be in electronic communication through communications connection 1230 with entertainment equipment 1510, which comprises an access device or similar equipment as just described provided adjacent to exercise equipment 1505 that allows a user to select among various entertainment options. In addition, users may be able to choose to view and or listen to a prescribed program such as a health education program or a motivational program. I/O device 1200 and entertainment equipment 1510 may be adapted to enable I/O device 1200 to collect from entertainment equipment 1510 and store data relating to the various entertainment or other programming options selected by the user.

In addition, health club 1500 includes computing device 1515, which may be a PC or a server computer or the like. I/O device 1200 is adapted to be in electronic communication with computing device 1515 through communications connection 1230 to enable the data collected, stored and, in a specific embodiment, processed by I/O device 1200 to be transmitted to computing device 1515. For example, a wireless interface device in electronic communication with computing device 1515 could be placed near the front desk of health club 1500. As a user exits health club 1500, he or she could place I/O device 1200 in proximity with the wireless internet device and, either automatically or after a further step such as pressing a button, the data collected, stored and, in a specific embodiment, processed by I/O device 1200 while the user was in health club 1500 would be downloaded from I/O device 1200 and transmitted to computing device 1515. The data transmitted to computing device 1515 may also include data manually entered into I/O device 1200, such as caloric consumption data. As an alternative, the wireless interface device could be replaced by a docking station or a jack device that requires I/O device to be physically coupled thereto to establish an electronic communications path.

As seen in FIG. 46, computing device 1515 is in electronic communication with remote server 1520 through the Internet or a similar computer network. Remote server 1520 aggregates data transmitted from computing device 1515 for a number of users and, according to a specific embodiment, from similar devices located at other health clubs. In an alternate embodiment, data may be transmitted directly from I/O device 1200 to remote server 1520, rather than through computing device 1515, by, for example a long range wireless communications protocol such a those used with cell phones or 2-way pagers. Remote server 1520 may include a web server that makes the collected data, such as physiological, exercise activity, and/or caloric consumption data, available to users over the Internet through computing device 1525 under the control of the user, such as a PC, cell phone or PDA. The data may, in one embodiment, be presented to users in a form similar to that described in connection with FIGS. 5 through 11. In addition, remote server 1520 may be used to segregate the data collected from entertainment equipment 1510 and, in a specific embodiment, demographic information about the users associated with the data. The segregated data may be used to track the level of use of each programming channel and provide ratings, similar to Nielsen ratings, for each programming channel.

Furthermore, I/O device 1200 may also be used to collect data from devices located outside of health club 1500 that have capabilities and functionality that are similar to exercise equipment 1505 or entertainment equipment 1510. For example, a user that normally exercises at health club 1500 may be out of town for a period of time and, while out of town, may exercise at another facility. I/O device 1200 maybe used to collect data from exercise and/or entertainment equipment used at the other facility, provided such equipment has capabilities and functionality similar to that of exercise equipment 1505 and entertainment equipment 1510. I/O device 1200 may also be used to collect data when a user is exercising or watching or listening to some sort of programming, as described herein, at home using compatible equipment. In addition, I/O device 1200 can collect relevant information while the user is not at health club 1500 through ways other than from compatible equipment. For example, if a user takes a walk at home, I/O device 1200 could collect data relating to the walk from sensor device 1201 or from manual entry. When the user returns to health club 1500, he or she can transmit the data collected while he or she was away or while exercising or engaging in other activities at home to computing device 1515, thereby eliminating gaps in data collection that otherwise would have occurred while the user was away from health club 1500. By eliminating such gaps, a program being followed by the user or goals set by the user can be more accurately monitored and modified, for example by a personal trainer or though an artificial intelligence program or algorithm employed by I/O device 1200.

In one embodiment, I/O device 1200 would store information about the user including demographic information, identification information, musical preferences, and the type of program they are on, such as rehab, cardio, or fat burning. I/O device 1200 may also collect information about the specific room it was in while the person interacted in the club, when they entered and left the room and what machine they used. In one specific embodiment, a wireless system may be utilized in which I/O device 1200 could understand it's own location in the facility through means of triangulating off two other RF transceivers in the facility.

According to yet another aspect of the present invention, instead of a space or facility like a health club requiring all the infrastructure for all it's machines to be networked with one another, either wired or wirelessly, and with a central computer to collect information about and control the machines, people can take I/O device 1200 with them as they interact with the space and use it to communicate with the equipment using local (not long distance wireless, or wires), low power communication methods, so when they use equipment such as a treadmill, I/O device 1200 tracks the machine they were on, the use, how they performed, etc. I/O device 1200 may also select entertainment programs they want to watch and/or listen to. At the end of the session in the space or facility, the information can be downloaded to a specified site such as the central computer of the facility and/or a remote server. Thus, the space or facility avoided the need to establish a specific and costly infrastructure to connect up every piece of equipment in the facility. I/O device acts, instead, as an ad-hoc infrastructure as needed.

According to one embodiment of the present invention, sensor device 1201, which may be any one of sensor device 400 shown in FIGS. 12-17, stand alone sensor device 700 shown in FIG. 21, or sensor device 800 shown in FIGS. 22-26, includes a plurality of physiological and/or contextual sensors. For example, one particular embodiment of sensor device 400, stand alone sensor device 700, or sensor device 800 includes a 2-axis accelerometer, a heat flux sensor, a GSR sensor, a skin temperature sensor, a near-body ambient temperature sensor, and a receiver for receiving heart rate data from a heart rate sensor on, for example, a chest strap being worn by the user.

One aspect of the present invention relates to a sophisticated algorithm development process for creating a wide range of algorithms for generating information relating to a variety of variables from the data received from the plurality of physiological and/or contextual sensors on sensor device 1201. Such variables may include, without limitation, energy expenditure, including resting, active and total values, daily caloric intake, sleep states, including in bed, sleep onset, sleep interruptions, wake, and out of bed, and activity states, including exercising, sitting, traveling in a motor vehicle, and lying down, and the algorithms for generating values for such variables may be based on data from, for example, the 2-axis accelerometer, the heat flux sensor, the GSR sensor, the skin temperature sensor, the near-body ambient temperature sensor, and the heart rate sensor in the embodiment described above.

Note that there are several types of algorithms that can be computed. For example, and without limitation, these include algorithms for predicting user characteristics, continual measurements, durative contexts, instantaneous events, and cumulative conditions. User characteristics include permanent and semi-permanent parameters of the wearer, including aspects such as weight, height, and wearer identity. An example of a continual measurement is energy expenditure, which constantly measures, for example on a minute by minute basis, the number of calories of energy expended by the wearer. Durative contexts are behaviors that last some period of time, such as sleeping, driving a car, or jogging. Instantaneous events are those that occur at a fixed or over a very short time period, such as a heart attack or falling down. Cumulative conditions are those where the person's condition can be deduced from their behavior over some previous period of time. For example, if a person hasn't slept in 36 hours and hasn't eaten in 10 hours, it is likely that they are fatigued. Table 3 below shows numerous examples of specific personal characteristics, continual measurements, durative measurements, instantaneous events, and cumulative conditions.

TABLE 3

| | |
|---|---|
| personal characteristics | age, sex, weight, gender, athletic ability, conditioning, disease, height, susceptibility to disease, activity level, individual detection, handedness, metabolic rate, body composition |
| continual measurements | mood, beat-to-beat variability of heart beats, respiration, energy expenditure, blood glucose levels, level of ketosis, heart rate, stress levels, fatigue levels, alertness levels, blood pressure, readiness, strength, endurance, amenability to interaction, steps per time period, stillness level, body position and orientation, cleanliness, mood or affect, approachability, caloric intake, TEF, XEF, 'in the zone'-ness, active energy expenditure, carbohydrate intake, fat intake, protein intake, hydration levels, truthfulness, sleep quality, sleep state, consciousness level, effects of medication, dosage prediction, water intake, alcohol intake, dizziness, pain, comfort, remaining processing power for new stimuli, proper use of the armband, interest in a topic, relative exertion, location, blood-alcohol level |
| durative measurements | exercise, sleep, lying down, sitting, standing, ambulation, running, walking, biking, stationary biking, road biking, lifting weights, aerobic exercise, anaerobic exercise, strength-building exercise, mind-centering activity, periods of intense emotion, relaxing, watching TV, sedentary, REM detector, eating, in-the-zone, interruptible, general activity detection, sleep stage, heat stress, heat stroke, amenable to teaching/learning, bipolar decompensation, abnormal events (in heart signal, in activity level, measured by the user, etc), startle level, highway driving or riding in a car, airplane travel, helicopter travel, boredom events, sport detection (football, baseball, soccer, etc), studying, reading, intoxication, effect of a drug |
| instantaneous events | falling, heart attack, seizure, sleep arousal events, PVCs, blood sugar abnormality, acute stress or disorientation, emergency, heart arrhythmia, shock, vomiting, rapid blood loss, taking medication, swallowing |
| cumulative conditions | Alzheimer's, weakness or increased likelihood of falling, drowsiness, fatigue, existence of ketosis, ovulation, pregnancy, disease, illness, fever, edema, anemia, having the flu, hypertension, mental disorders, acute dehydration, hypothermia, being-in-the-zone |

It will be appreciated that the present invention may be utilized in a method for doing automatic journaling of a wearer's physiological and contextual states. The system can automatically produce a journal of what activities the user was engaged in, what events occurred, how the user's physiological state changed over time, and when the user experienced or was likely to experience certain conditions. For example, the system can produce a record of when the user exercised, drove a car, slept, was in danger of heat stress, or ate, in addition to recording the user's hydration level, energy expenditure level, sleep levels, and alertness levels throughout a day.

According to the algorithm development process, linear or non-linear mathematical models or algorithms are constructed that map the data from the plurality of sensors to a desired variable. The process consists of several steps. First, data is collected by subjects wearing sensor device 1201 who are put into situations as close to real world situations as possible (with respect to the parameters being measured), such that the subjects are not endangered and so that the variable that the proposed algorithm is to predict can, at the same time, be reliably measured using highly accurate medical grade lab equipment. This first step provides the following two sets of data that are then used as inputs to the algorithm development process: (i) the raw data from sensor device 1201, and (ii) the data consisting of the gold-standard labels measured with the more accurate lab equipment. For cases in which the variable that the proposed algorithm is to predict relates to context detection, such as traveling in a motor vehicle, the gold-standard data is provided by the subjects themselves, such as through information input manually into sensor device 1201, a PC, or otherwise manually recorded. The collected data, i.e., both the raw data and the corresponding gold standard label data, is then organized into a database and is split into training and test sets.

Next, using the data in the training set, a mathematical model is built that relates the raw data to the corresponding gold standard labeled data. Specifically, a variety of machine learning techniques are used to generate two types of algorithms: 1) algorithms known as feature detectors that produce a result that is highly correlated with the lab-measured level (e.g. VO2 level information from a metabolic cart, douglas bag, or doubly labeled water), and 2) algorithms known as context detectors that predict various contexts (e.g., running, exercising, lying down, sleeping, driving) useful for the overall algorithm. A number of well known machine learning techniques may be used in this step, including artificial neural nets, decision trees, memory-based methods, boosting, attribute selection through cross-validation, and stochastic search methods such as simulated annealing and evolutionary computation. After a suitable set of feature and context detectors are found, several well known machine learning methods are used to cross-validate the models using the training data and increase the quality of the models of the data. Techniques used in this phase include, but are not limited to, multilinear regression, locally weighted regression, decision trees, artificial neural networks, stochastic search methods, support vector machines, and model trees.

At this stage, the models make predictions on, for example, a minute by minute basis. Inter-minute effects are next taken into account by creating an overall model that integrates the minute by minute predictions. A well known or custom windowing and threshold optimization tool may be used in this step to take advantage of the temporal continuity of the data. Finally, the model's performance can be evaluated on the test set, which has not yet been used in the creation of the algorithm. Performance of the model on the test set is thus a good estimate of the algorithm's expected performance on other unseen data. Finally, the algorithm may undergo live testing on new data for further validation.

Further examples of the types of non-linear functions and/or machine learning method that may be used in the present invention include the following: conditionals, case statements, logical processing, probabilistic or logical inference, neural network processing, kernel based methods, memory-based lookup (kNN, SOMs), decision lists, decision-tree prediction, support vector machine prediction, clustering, boosted methods, cascade-correlation, Boltzmann classifier, regression trees, case-based reasoning, Gaussians, Bayes nets, dynamic Bayesian networks, HMMs, Kalman filters, Gaussian processes, algorithmic predictors (e.g. learned by evolutionary computation or other program synthesis tools).

Although one can view an algorithm as taking raw sensor values or signals as input, performing computation, and then producing a desired output, it is useful in one preferred embodiment to view the algorithm as a series of derivations that are applied to the raw sensor values. Each derivation produces a signal referred to as a derived channel. The raw sensor values or signals are also referred to as channels, specifically raw channels rather than derived channels. These derivations, also referred to as functions, can be simple or complex but are applied in a predetermined order on the raw values and, possibly, on already existing derived channels. The first derivation must, of course, only take as input raw sensor signals, but subsequent derivations can take as input previously derived channels. Note that one can easily determine, from the order of application of derivations, the particular channels utilized to derive a given derived channel. Also note that inputs that a user provides on an I/O device or in some fashion can also be included as raw signals which can be used by the algorithms. For example, the category chosen to describe a meal can be used by a derivation that computes the caloric estimate for the meal. In one embodiment, the raw signals are first summarized into channels that are sufficient for later derivations and can be efficiently stored. These channels include derivations such as summation, summation of differences, and averages. Note that although summarizing the high-rate data into compressed channels is useful both for compression and for storing useful features, it may be useful to store some or all segments of high rate data as well, depending on the exact details of the application. In one embodiment, these summary channels are then calibrated to take minor measurable differences in manufacturing into account and to result in values in the appropriate scale and in the correct units. For example, if, during the manufacturing process, a particular temperature sensor was determined to have a slight offset, this offset can be applied, resulting in a derived channel expressing temperature in degrees Celsius.

Figure 47:
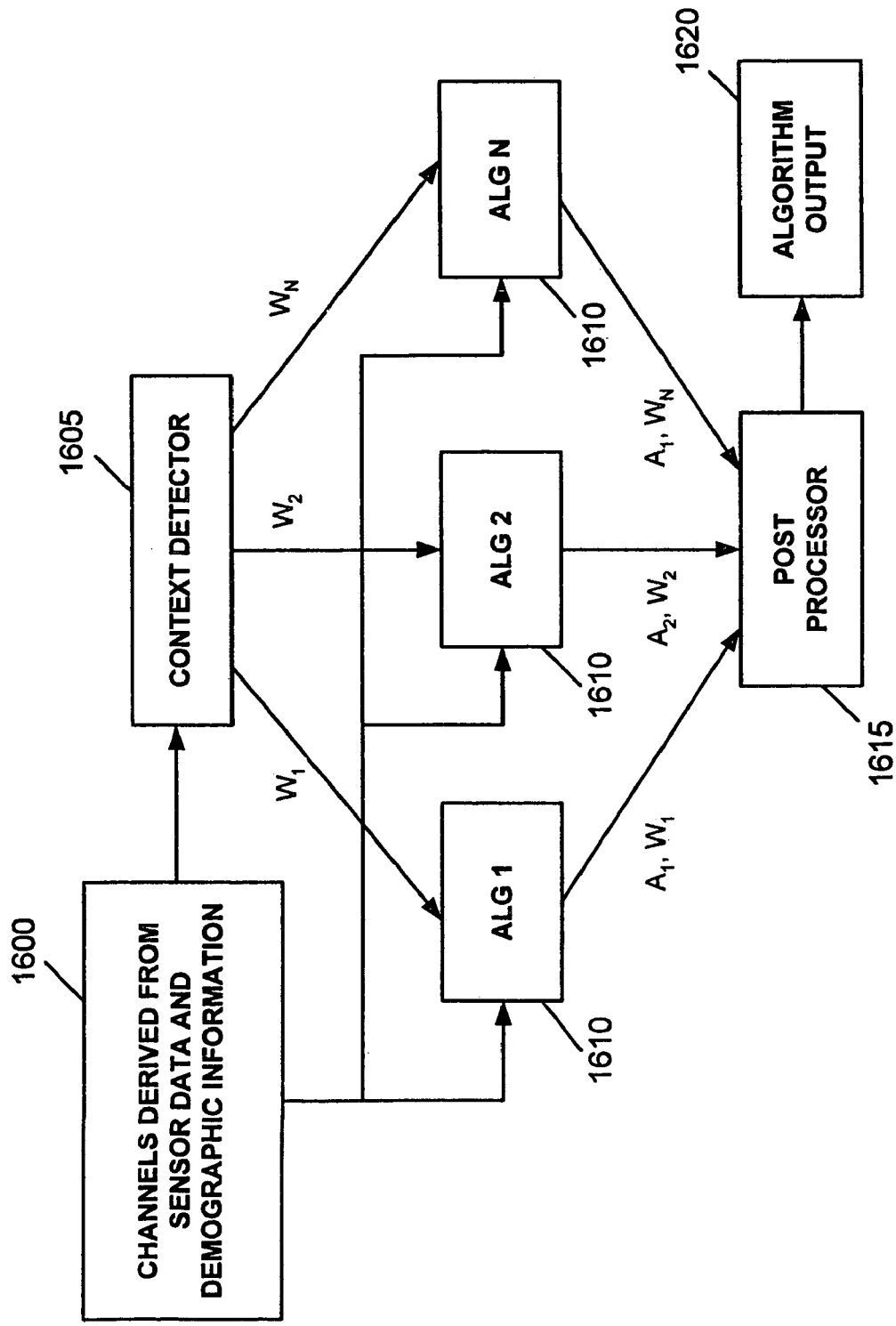
FIG. 47 is a block diagram showing the format of algorithms that are developed according to an aspect of the present invention.

For purposes of this description, a derivation or function is linear if it is expressed as a weighted combination of its inputs together with some offset. For example, if FOO and BAR are two raw or derived channels, then all derivations of the form A*FOO+B*BAR+C, where A, B, and C are constants, is a linear derivation. A derivation is non-linear with respect to its inputs if it is not expressed as a weighted sum of the inputs with a constant offset. An example of a nonlinear derivation is as follows: if (FOO>7) then return BAR*9, else return (BAR*3.5+912). A channel is linearly derived if all derivations involved in computing it are linear, and a channel is nonlinearly derived if any of the derivations used in creating it are nonlinear. A channel nonlinearly mediates a derivation if changes in the value of the channel change the computation performed in the derivation, keeping all other inputs constant. According to a preferred embodiment of the present invention, the algorithms that are developed using this process will have the format shown conceptually in FIG. 47. Specifically, the algorithm will take as inputs the channels derived from the sensor data collected by the sensor device from the various sensors and demographic information for the individual as shown in box 1600. The algorithm includes at least one context detector 1605 that produces a weight, shown as $W_1$ through $W_N$, expressing the probability that a given portion of collected data, such as is collected over a minute, was collected while the wearer was in each of several possible contexts. Such contexts may include whether the individual was at rest or active. In addition, for each context, a regression algorithm 1610 is provided where a continuous prediction is computed taking raw or derived channels as input. The individual regressions can be any of a variety of regression equations or methods, including, for example, multivariate linear or polynomial regression, memory based methods, support vector machine regression, neural networks, Gaussian processes, arbitrary procedural functions, etc. Each regression is an estimate of the output of the parameter of interest in the algorithm, for example energy expenditure. Finally, the outputs of each regression algorithm 1610 for each context, shown as $A_1$ through $A_N$, and the weights $W_1$ through $W_N$ are combined in a post-processor 1615 which outputs the parameter of interest being measured or predicted by the algorithm, shown in box 1620. In general, the post-processor 1615 can consist of any of many methods for combining the separate contextual predictions, including committee methods, boosting, voting methods, consistency checking, or context based recombination.

Figure 48:
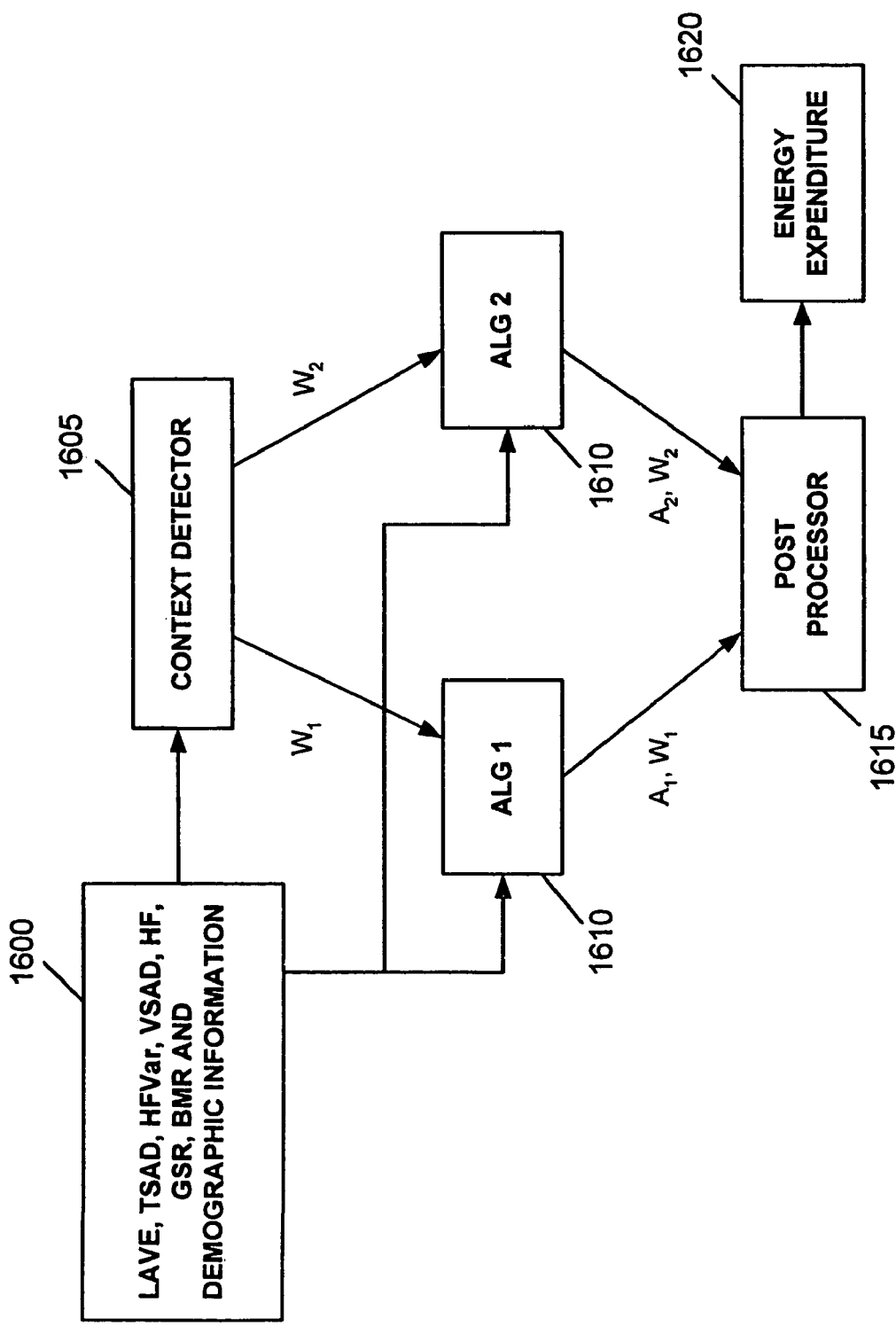
FIG. 48 is a block diagram illustrating an example algorithm for predicting energy expenditure according to the present invention.

Referring to FIG. 48, an example algorithm for measuring energy expenditure of an individual is shown conceptually. This example algorithm may be run on sensor device 1201 having at least an accelerometer, a heat flux sensor and a GSR sensor, or I/O 1200 that receives data from such a sensor device. In this example algorithm, the raw data from the sensors is calibrated and numerous values based thereon, i.e., derived channels, are created. In particular, the following derived channels, shown at 1600 in FIG. 48, are computed from the raw signals and the demographic information: (1) longitudinal accelerometer average (LAVE), based on the accelerometer data; (2) transverse accelerometer sum of average differences (TSAD), based on the accelerometer data; (3) heat flux high gain average variance (HFvar), based on heat flux sensor data; (4) vector sum of transverse and longitudinal accelerometer sum of absolute differences or SADs (VSAD), based on the accelerometer data; (5) galvanic skin response low gain (GSR), based on the GSR data; and (6) Basal Metabolic Rate (BMR), based on demographic information. Context detector 1605 consists of a naïve Bayesian classifier that predicts whether the wearer is active or resting using the LAVE, TSAD, and HFvar derived channels. The output is a probabilistic weight ($W_1$ and $W_2$ for the two contexts rest and active). For the rest context, the regression algorithm 1610 is a linear regression combining channels derived from the accelerometer, the heat flux sensor, the user's demographic data, and the galvanic skin response sensor. The equation, obtained through the algorithm design process, is A*VSAD+B*HFvar+C*GSR+D*BMR+E, where A, B, C, D and E are constants. The regression algorithm 1610 for the active context is the same, except that the constants are different. The post-processor 1615 for this example is to add together the weighted results of each contextual regression. If $A_1$ is the result of the rest regression and $A_2$ is the result of the active regression, then the combination is just $W_1*A_1+W_2*A_2$, which is energy expenditure shown at 1620. In another example, a derived channel that calculates whether the wearer is motoring (driving in a car) at the time period in question might also be input into the post-processor 1615. The process by which this derived motoring channel is computed is algorithm 3. The post-processor 1615 in this case might then enforce a constraint that when the wearer is predicted to be driving by algorithm 3, the energy expenditure is limited for that time period to a value equal to some factor (e.g. 1.3) times their minute by minute basal metabolic rate.

This algorithm development process may be used to create algorithms to enable sensor device 1201 to detect and measure various parameters, including, without limitation, the following: (i) when an individual is suffering from duress, including states of unconsciousness, fatigue, shock, drowsiness, heat stress and dehydration; and (ii) an individual's state of readiness, health and/or metabolic status, such as in a military environment, including states of dehydration, under-nourishment and lack of sleep. In addition, algorithms maybe developed for other purposes, such as filtering, signal clean-up and noise cancellation for signals measured by a sensor device as described herein. As will be appreciated, the actual algorithm or function that is developed using this method will be highly dependent on the specifics of the sensor device used, such as the specific sensors and placement thereof and the overall structure and geometry of the senor device. Thus, an algorithm developed with one sensor device will not work as well, if at all, on sensor devices that are not substantially structurally identical to the sensor device used to create the algorithm.

Another aspect of the present invention relates to the ability of the developed algorithms to handle various kinds of uncertainty. Data uncertainty refers to sensor noise and possible sensor failures. Data uncertainty is when one cannot fully trust the data. Under such conditions, for example, if a sensor, for example an accelerometer, fails, the system might conclude that the wearer is sleeping or resting or that no motion is taking place. Under such conditions it is very hard to conclude if the data is bad or if the model that is predicting and making the conclusion is wrong. When an application involves both model and data uncertainties, it is very important to identify the relative magnitudes of the uncertainties associated with data and the model. An intelligent system would notice that the sensor seems to be producing erroneous data and would either switch to alternate algorithms or would, in some cases, be able to fill the gaps intelligently before making any predictions. Determining when sensors have failed and when data channels are no longer reliable is a non-trivial task because a failed sensor can sometimes result in readings that may seem consistent with some of the other sensors and the data can also fall within the normal operating range of the sensor.

Clinical uncertainty refers to the fact that different sensors might indicate seemingly contradictory conclusions. Clinical uncertainty is when one cannot be sure of the conclusion that is drawn from the data. For example, the accelerometers might indicate that the wearer is motionless (leading toward a conclusion of "resting"), the galvanic skin response sensor might provide a very high response (leading toward "active"), and the heat flow sensor might indicate that the wearer is still dispersing substantial heat (leading toward "active"). How should these differing factors be assessed? An inferior system would simply try to vote among the sensors or use similarly unfounded methods to integrate the various readings. The present invention instead weights the important joint probabilities and determines the appropriate most likely conclusion (which might be, for this example, that the wearer is currently performing or has recently performed a low motion activity such as stationary biking).

The terms and expressions which have been employed herein are used as terms of description and not as limitation, and there is no intention in the use of such terms and expressions of excluding equivalents of the features shown and described or portions thereof, it being recognized that various modifications are possible within the scope of the invention claimed. Although particular embodiments of the present invention have been illustrated in the foregoing detailed description, it is to be further understood that the present invention is not to be limited to just the embodiments disclosed, but that they are capable of numerous rearrangements, modifications and substitutions.

What is claimed is:

1. An apparatus for monitoring human status parameters of an individual, comprising:
a sensor device, said sensor device being in electronic communication with at least two sensors continually generating data at least one of a first and second parameter of an individual during non-sedentary activities, wherein said first and second parameters are produced by at least one of said individual's body and the environment adjacent to said individual's body; and
an I/O device in electronic communication with said sensor device, said I/O device receiving data of said first parameter and data of said second parameter from said sensor device, at least one of said first parameter and said second parameter being physiological, said I/O device in electronic communication with a processor, said processor generating derived data using said data of said first parameter and said data of said second parameter, said derived data comprising a third parameter of said individual, said third parameter comprising caloric expenditure data and being an individual status parameter that cannot be directly detected by any one of said at least two sensors, said I/O device comprising a displaying means displaying information related to said third parameter.

2. An apparatus according to claim 1, said I/O device tbrther including means for enabling said individual to enter information relating to said individual into said I/O device.

3. An apparatus according to claim 1, said derived data of said individual being selected from the group consisting of: physical activity, sleep activity, nutrition activity, mind centering activity, stress level, metabolic rate, and oxygen consumption rate.

4. An apparatus according to claim 1, at least one of said at least two sensors being a physiological sensor selected from the group consisting of: respiration sensors, temperature sensors, heat flux sensors, body conductance sensors, body resistance sensors, body potential sensors, brain activity sensors, blood pressure sensors, body impedance sensors, body motion sensors, body volume sensors, oxygen consumption sensors, body chenistry sensors, body position sensors, body pressure sensors, light absorption sensors, body sound sensors, electrochemical sensors, and optical sensors.

5. An apparatus according to claim 1, said derived data being a physiological parameter of said individual.

6. An apparatus according to claim 1, said I/O device including means for enabling said individual to enter information relating to calories consumed by said individual, said processor generating caloric consumption data using said information relating to calories consumed, said displaying means displaying information based on said caloric expenditure data and said caloric consumption data.

7. An apparatus according to claim 6, wherein said information relating to calories consumed by said individual comprises information relating to foods consumed by said individual.

8. An apparatus according to claim 7, wherein said I/O device further comprises a database of food data comprising food items and associated caloric values, said database being used to generate said caloric consumption data using said information relating to foods consumed by said individual.

9. An apparatus according to claim 1, wherein said displaying means displays energy balance data.

10. An apparatus according to claim 1, wherein said displaying means displays a rate of weight loss or gain of said individual.

11. An apparatus according to claim 1, wherein said displaying means displays information relating to one or more goals of said individual, said goals relating to one or more of caloric consumption, caloric expenditure, energy balance and rate of weight loss or gain.

12. An apparatus according to claim 1, said derived data comprising data relating to caloric consumption of said individual.

13. An apparatus according to claim 2, wherein information entered by said individual is also used to generate said derived data.

14. An apparatus according to claim 13, said derived data comprising data relating to caloric consumption of said individual.

15. An apparatus according to claim 1, at least one of said at least two sensors being chosen from the group consisting of body motion sensors generating data of motion, skin conductance sensors generating data of the resistance of said individual's skin to electric current, heat flux sensors generating data of heat flow, body potential sensors generating data of heart beats of said individual, and temperature sensors generating data of a temperature of said individual's skin, said data of at least a first parameter and a second parameter comprising at least two of said data of motion, said data of resistance of said individual's skin to electric cuirent, said data of heat flow, said data of heart beats and said data of a temperature of said individual's skin.

16. An apparatus according to claim 1, at least one of said at least sensors being a contextual sensor.

17. An apparatus according to claim 1, wherein said processor is within said I/O device.

18. An apparatus according to claim 1, wherein said processor is in a computing device, said computing device being in electronic communication with said I/O device.

19. An apparatus according to claim 1, said apparatus further comprising a computing device in electronic communication with said apparatus, said apparatus communicating at least one of said data of at least a first parameter and said data of a second parameter and said derived data to said computing device.

20. An apparatus according to claim 1, said processor being adapted to cause said displaying means to display one or more suggestions for achieving one or more goals of said individual.

21. An apparatus for tracking caloric consumption and caloric expenditure of an individual, comprising:
at least two sensors adapted to be worn on an individual's body during a plurality of activities including non-resting activities, said sensors in electronic communication with a processor, at least one of said sensors being a physiological sensor, said sensors adapted to generate data of at least one of a first parameter of said individual and a second parameter of said individual during said plurality of non-resting activities, said first and second parameters being produced by at least one of said individual's body and the environment adjacent to said individual's body, said first parameter being physiological, said processor being programmed to generate caloric expenditure data of said individual using said data of a first parameter and a second parameter, said caloric expenditure data including active caloric expenditure data;
an I/O device in electronic communication with said processor, said I/O device receiving said caloric expenditure data from said processor, said I/O device including means for enabling said individual to enter information relating to calories consumed by said individual, said information relating to calories consumed being used to generate caloric consumption data, and said I/O device comprising a displaying means for displaying information based on said caloric expenditure data and said caloric consumption data.

22. An apparatus according to claim 21, wherein said information relating to calories consumed by said individual comprises information relating to foods consumed by said individual.

23. An apparatus according to claim 22, wherein said I/O device has access to a database of food data comprising food items and associated caloric values, said database being used to generate said caloric consumption data using said information relating to foods consumed by said individual.

24. An apparatus according to claim 23, said I/O device further comprising said database.

25. An apparatus according to claim 21, wherein said information displayed by said displaying means includes energy balance data.

26. An apparatus according to claim 21, wherein said information displayed by said displaying means includes a rate of weight loss or gain of said individual.

27. An apparatus according to claim 21, wherein said information displayed by said displaying means includes information relating to one or more goals of said individual, said goals relating to one or more of caloric consumption, caloric expenditure, energy balance and rate of weight loss or gain.

28. An apparatus according to claim 21, wherein one of said at least two sensors and said processor are included within a single device.

29. An apparatus according to claim 21, wherein at least one of said at least two sensors is part of said I/O device.

30. An apparatus according to claim 1, said I/O device being a weight scale.

31. An apparatus according to claim 1, further comprising a weight scale, wherein said weight scale generates data indicative of weight, said data indicative of weight used by said processor to generate at least one of said caloric expenditure data and said caloric consumption data.

32. An apparatus according to claim 21, wherein at least two of said least two sensors are physiological and wherein said second parameter is physiological.

33. An apparatus according to claim 32, said at least two sensors being chosen from the group consisting of body motion sensors adapted to generate data of motion, skin conductance sensors adapted to generate data of the resistance of said individual's skin to electric current, heat flux sensors adapted to generate data of heat flow, body potential sensors adapted to generate data of heart beats of said individual, and temperature sensors adapted to generate data of a temperature of said individual's skin, said data of at least a first parameter and a second parameter comprising at least two of said data of motion, said data of resistance of said individual's skin to electric current, said data of heat flow, said data of heart beats and said data of a temperature of said individual's skin.

34. An apparatus according to claim 21, at least one of said at least two sensors being a contextual sensor.

35. An apparatus according to claim 34, said contextual sensor being selected from the group consisting of an ambient temperature sensor and a global positioning sensor.

36. An apparatus according to claim 21, said I/O device being adapted to cause said displaying means to display one or more suggestions for achieving one or more goals of said individual.

37. An apparatus according to claim 1 wherein at least two of said sensor device, said processor and said I/O device are housed in a single unit.

38. An apparatus according to claim 1 wherein said sensor device is adapted to be worn on the upper arm of said individual.

39. An apparatus according to claim 37 wherein said single unit is adapted to be worn on the upper arm of said individual.

* * * * *

UNITED STATES PATENT AND TRADEMARK OFFICE
CERTIFICATE OF CORRECTION

PATENT NO. : 7,285,090 B2  
APPLICATION NO. : 10/682759  
DATED : October 23, 2007  
INVENTOR(S) : John Stivoric et al.

Page 1 of 1

It is certified that error appears in the above-identified patent and that said Letters Patent is hereby corrected as shown below:

In the CLAIMS:

column 69, line 6, claim 1, after "generating data" insert --of--;

column 69, line 27, claim 2, delete "tbrther" and insert --further--;

column 69, line 41, claim 4, delete "chenistry" and insert --chemistry--;

column 70, line 29, claim 16, after "at least" insert --two--;

column 70, line 38, claim 19, after "at least one of said data of at least" insert --one of--;

column 71, line 40, claim 31, after "expenditure data and" delete "said";

column 72, line 15, claim 33, after "least" insert --one of--.

Signed and Sealed this  
Twelfth Day of June, 2012

David J. Kappos  
*Director of the United States Patent and Trademark Office*